US010655163B2

(12) United States Patent
Weissleder et al.

(10) Patent No.: US 10,655,163 B2
(45) Date of Patent: *May 19, 2020

(54) METHODS, KITS, AND SYSTEMS FOR MULTIPLEXED DETECTION OF TARGET MOLECULES AND USES THEREOF

(71) Applicant: THE GENERAL HOSPITAL CORPORATION, Boston, MA (US)

(72) Inventors: Ralph Weissleder, West Peabody, MA (US); Sarit S. Agasti, Brighton, MA (US); Vanessa M. Peterson, Somerville, MA (US); Adeeti Ullal, Saratoga, CA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,643

(22) Filed: Mar. 4, 2019

(65) Prior Publication Data

US 2019/0256888 A1   Aug. 22, 2019

Related U.S. Application Data

(63) Continuation of application No. 14/897,025, filed as application No. PCT/US2014/040731 on Jun. 3, 2014, now Pat. No. 10,266,874.

(60) Provisional application No. 61/912,054, filed on Dec. 5, 2013, provisional application No. 61/834,111, filed on Jun. 12, 2013, provisional application No. 61/972,940, filed on Mar. 31, 2014.

(51) Int. Cl.
*C12Q 1/6804* (2018.01)
*C12Q 1/6816* (2018.01)
*C12Q 1/6823* (2018.01)
*G01N 33/53* (2006.01)

(52) U.S. Cl.
CPC ........ *C12Q 1/6804* (2013.01); *C12Q 1/6816* (2013.01); *C12Q 1/6823* (2013.01); *G01N 33/53* (2013.01); *G01N 2458/10* (2013.01)

(58) Field of Classification Search
CPC .................................................. C12Q 1/6804
USPC .......................................................... 506/9
See application file for complete search history.

(56) References Cited

U.S. PATENT DOCUMENTS

| 7,941,279 B2 | 5/2011 | Hwang et al. |
| 8,415,102 B2 | 4/2013 | Geiss et al. |
| 2005/0079520 A1 | 4/2005 | Wu |
| 2007/0009931 A1 | 1/2007 | Kirsch |
| 2010/0022761 A1 | 1/2010 | Chen |
| 2010/0323913 A1 | 12/2010 | Young et al. |
| 2011/0086774 A1 | 4/2011 | Dunaway |
| 2011/0201515 A1 | 8/2011 | Webster et al. |
| 2012/0077693 A1 | 3/2012 | Cazalis et al. |
| 2013/0017971 A1 | 1/2013 | Geiss et al. |
| 2015/0377881 A1* | 12/2015 | Super ................. G01N 33/5306 435/7.92 |

FOREIGN PATENT DOCUMENTS

| JP | 2010523159 A | 7/2010 | |
| JP | 201327387 | 2/2013 | |
| WO | 2006049289 A1 | 11/2006 | |
| WO | 2008124847 A2 | 4/2008 | |
| WO | 2010083252 A2 | 1/2010 | |
| WO | 2011097644 A2 | 2/2011 | |
| WO | 2011143583 A1 | 11/2011 | |
| WO | WO-2011143583 A1 * | 11/2011 | ........... C12Q 1/6804 |
| WO | 2013059105 A2 | 10/2012 | |

OTHER PUBLICATIONS

Agasti et al., "Photocleavable DNA Barcode-Antibody Conjugates Allow Sensitive and Multiplexed Protein Analysis in Single Cells", J. Am. Chem. Soc. 134:18499-18502 (2012).
Nam et al., "Nanoparticle-Based Bio-Bar Codes for the Ultrasensitive Detection of Proteins", Science 301:1884-1886 (2003).
Ullal et al., "Cancer cell profiling by barcoding allows multiplexed protein analysis in fine needle aspirates", Sci. Tranl. Med. 6(219):219ra9 (2014).
Basik et al., "Biopsies: next-generation biospecimens for tailoring therapy." Nature Reviews Clinical Oncology 10 (8):437-450 (2013).
Bendall et al., "Single-Cell Mass Cytometry of Differential Immune and Drug Responses Across a Human-Hematopoietic Continuum", Science 332(6030):687-696 (2011).
Benoist et al., "Flow Cytometry, Amped Up", Science 332:677-678 (2011).
Devaraj et al., "Fast and Sensitive Pretargeted Labeling of Cancer Cells through a Tetrazine/trans-Cyclooctene Cycloaddition", Angewandte Chemie International Edition 48:7013-7016 (2009).
Ellerbee et al., "Quantifying Colorimetric Assays in Paper-Based Microfluidic Devices by Measuring the Transmission of Light Through Paper", Analytical Chemistry 81(20):8447-8452 (2009).
Fortina et al., "Digital mRNA profiling", Nature Biotechnology 26(3):293-294 (2008).
Fredriksson et al., "Multiplexed protein detection by proximity ligation for cancer biomarker validation", Nature Methods 4(4):327-329 (2007).

(Continued)

*Primary Examiner* — Karla A Dines
(74) *Attorney, Agent, or Firm* — Nixon Peabody LLP

(57) ABSTRACT

Described herein are methods, compositions, kits and systems for multiplexed detection of target molecules from a sample. In some embodiments, the methods, compositions, kits and systems can be used to perform multiplexed protein analysis of a sample (e.g., a sample comprising a small number of cells or a single-cell sample). In some embodiments, the same sample subjected to a multiplexed protein analysis using the methods, compositions, kits and systems described herein can also be subjected to a nucleic acid (e.g., RNAs, microRNAs, and/or DNA) analysis, thereby creating an integrated expression profiling from a limited amount of sample.

14 Claims, 33 Drawing Sheets

Specification includes a Sequence Listing.

(56) References Cited

OTHER PUBLICATIONS

Geiss et al., "Direct multiplexed measurement of gene expression with color-coded probe pairs", Nature Biotechnology 26(3):317-325 (2008).
Gerdes et al., "Highly multiplexed single-cell analysis of formalin-fixed, paraffin-embedded cancer tissue", Proceedings of the National Academy of Sciences 110(29):11982-11987 (2013).
Haun et al., "Micro-NMR for Rapid Molecular Analysis of Human Tumor Samples", Science Translational Medicine 3(71):71ra16(2011). (27 pages).
Hendrickson et al., "High sensitivity multianalyte immunoassay using covalent DNA-labeled antibodies and polymerase chain reaction", Nucleic Acids Research 23(3):522-529 (1995).
Homola J., "Surface Plasmon Resonance Sensors for Detection of Chemical and Biological Species", Chemical Reviews 108(2):462-493 (2008).
Hsi E., "A Practical Approach for Evaluating New Antibodies in the Clinical Immunohistochemistry Laboratory", Archives of Pathology & Laboratory Medicine 125:289-294 (2001).
Kazane et al., "Site-specific DNA-antibody conjugates for specific and sensitive immuno-PCR", Proceedings of the National Academy of Sciences 109(10):3731-3736 (2012).
Konry et al., "Ultrasensitive Detection of Low-Abundance Surface-Marker Protein Using Isothermal Rolling Circle Amplification in a Microfluidic Nanoliter Platform", Small 7(3): (2011). (10 pages).
Koob et al., "Protein analysis through Western blot of cells excised individually from human brain and muscle tissue", Analytical Biochemistry 425(2):120-124 (2012).
Lanni et al., "Mass spectrometry imaging and profiling of single cells", Journal of Proteomics 75(16):5036-5051 (2012).
Paez et al., "EGFR Mutations in Lung Cancer: Correlation with Clinical Response to Gefitinib Therapy", Science 304:1497-1500 (2004).
Rosi et al., "Nanostructures in Biodiagnostics", Chemical Reviews 105(4):1547-1562 (2005).
Rotem et al., "Protein Detection by Nanopores Equipped with Aptamers", Journal of the American Chemical Society 134:2781-2787 (2012).
Sano et al., "Immuno-PCR: very sensitive antigen detection by means of specific antibody-DNA conjugates", Science 258:120-122 (1992).
Shi et al., "Single-cell proteomic chip for profiling intracellular signaling pathways in single tumor cells", Proceedings of the National Academy of Sciences 109(2):419-424 (2012).
Soda et al., "Identification of the transforming EML4-ALK fusion gene in non-small-cell lung cancer", Nature 448:561-566 (2007).
Thurer et al., "Potentiometric Immunoassay with Quantum Dot Labels", Analytical Chemistry 79(13):5107-5110 (2007).
Venkatesan et al., "Nanopore sensors for nucleic acid analysis", Nature Nanotechnology 6:615-624 (2011).
Vogelstein et al., "Cancer Genome Landscapes", Science 339(6127):1546-1558 (2013).
Wacker et al., "Magneto Immuno-PCR: A novel immunoassay based on biogenic magnetosome nanoparticles", Biochemical and Biophysical Research Communications 357:391-396 (2007).
Yaffe M., "The Scientific Drunk and the Lamppost: Massive Sequencing Efforts in Cancer Discovery and Treatment", Science Signaling 6(269):pe13 (2013). (4 pages).
Coleman et al., "S-Pixyl Analogues as Photocleavable Protecting Groups for Nucleosides", Journal of Organic Chemistry 67:7641-7648 (2002).

\* cited by examiner

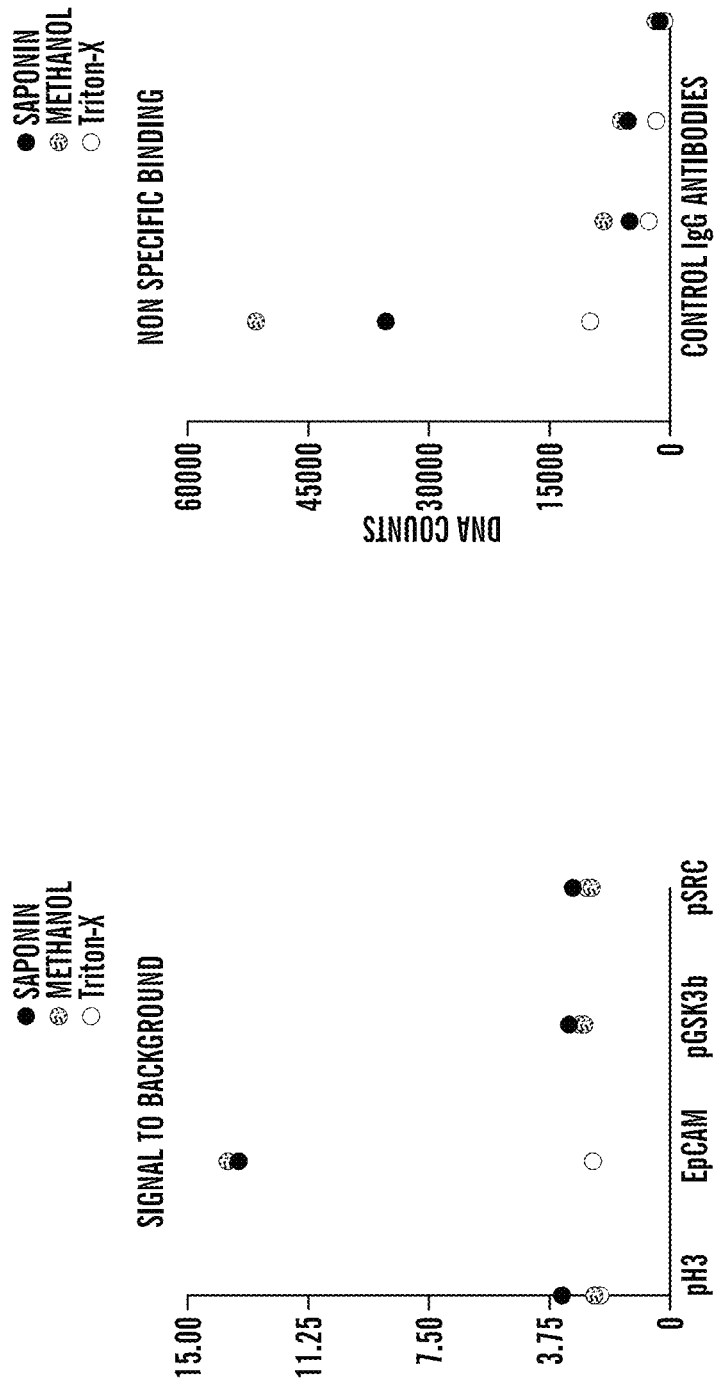

| CORRELATION TO BULK | SPEARMAN r | CONFIDENCE INTERVAL |
|---|---|---|
| SINGLE CELL 1 | 0.938 | 0.897-0.963 |
| SINGLE CELL 2 | 0.963 | 0.939-0.978 |
| SINGLE CELL 3 | 0.53 | 0.317-0.686 |
| SINGLE CELL 4 | 0.61 | 0.426-0.746 |

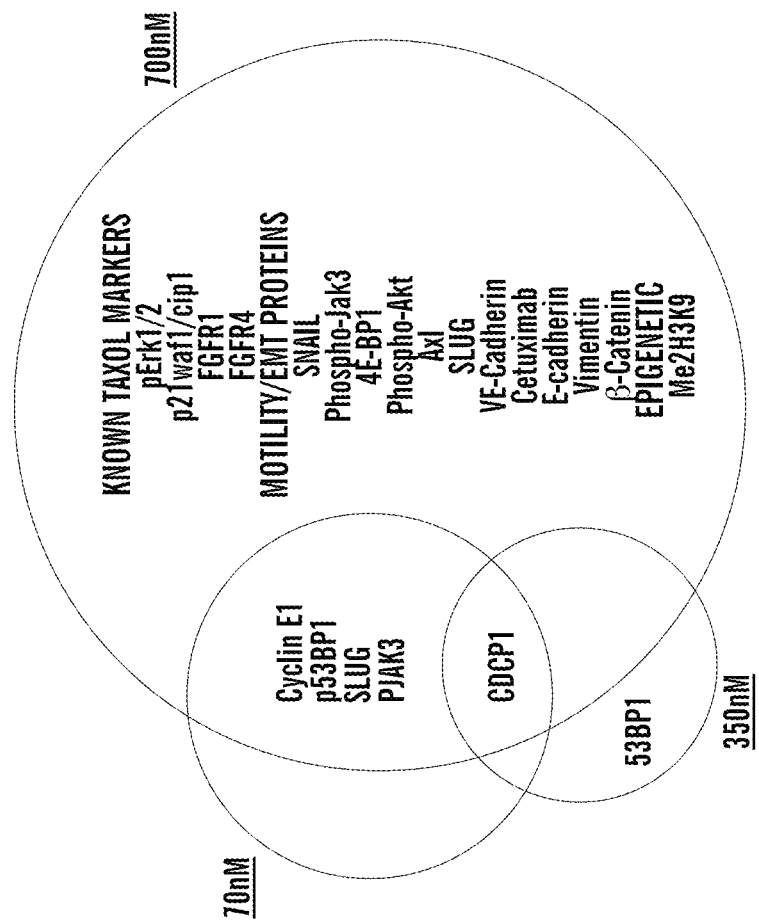
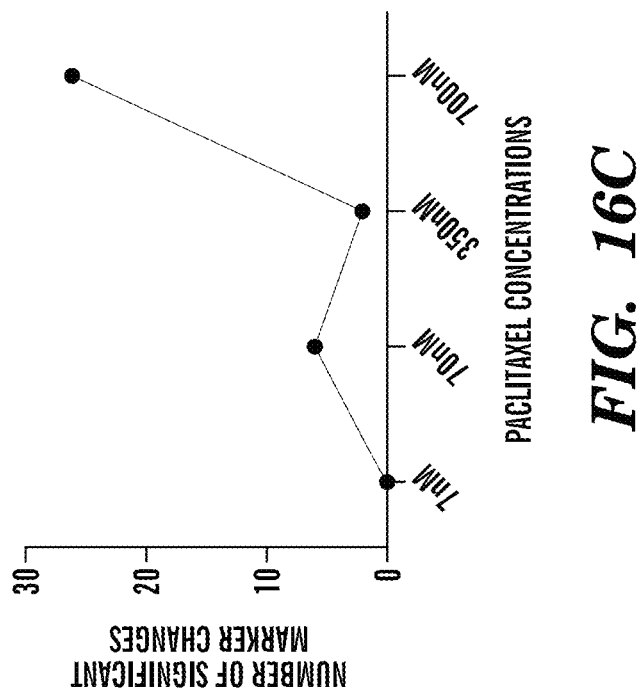
FIG. 16C
FIG. 16D

METHODS, KITS, AND SYSTEMS FOR MULTIPLEXED DETECTION OF TARGET MOLECULES AND USES THEREOF

CROSS-REFERENCE TO RELATED APPLICATIONS

This application is a continuation of U.S. application Ser. No. 14/897,025 filed Dec. 9, 2015, which application is a 35 U.S.C. § 371 National Phase Entry Application of International Application No. PCT/US2014/040731 filed Jun. 3, 2014, which designates the U.S., and claims the benefit under 35 U.S.C. § 119(e) of U.S. Provisional Application No. 61/834,111 filed Jun. 12, 2013, U.S. Provisional Application No. 61/912,054 filed Dec. 5, 2013, U.S. Provisional Application No. 61/972,940 filed Mar. 31, 2014, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 4, 2019, is named 030258-078413-PCT_SL, and is 34,864 bytes in size.

TECHNICAL FIELD

The present invention relates to methods, kits, and systems for detection of a plurality of target molecules in a sample. The methods, kits, and systems described herein can be used in diagnostic, prognostic, quality control and screening applications.

BACKGROUND

An increasing number of clinical trials, e.g., cancer trials, require patient samples, e.g., tissue biopsies, to measure individual drug response markers [1]. For example, surgically harvested tissues are often used to collect data at two ends of the cellular spectrum: (i) genomic analyses that reveal driver oncogenes and specific mutations [2] and (ii) protein analyses of selected biomarkers intended to monitor cellular responses [3, 4]. Ideally, clinical samples are collected serially to monitor change in expression levels of key proteins. This raises many challenges, notably risk of morbidity with repeat core biopsies, increased cost, and logistical limitations. Alternative sample collection methods include fine-needle aspirates (FNAs), "liquid biopsies" of circulating tumor cells, or analysis of scant cells present in other easily harvested fluids. However, these samples have much lower cell numbers than biopsies, thereby limiting the number of proteins that can be analyzed.

After tissues have been sampled, selecting ubiquitous biomarkers can be difficult because of heterogeneity and dynamic network changes. Typically, small-molecule drugs influence more than one target proteins, whereas numerous proteins modulate downstream specific drug actions, trigger alternative molecular pathways, and induce tumor cell death or resistance [5]. The current tools to profile these key proteins in scant clinical samples are limited; standard practice encompasses immunocytology, which often precludes broad protein analysis because of insufficient sample within FNAs or liquid biopsies [6]. Thus, the number of markers is often limited (<10) and requires time-consuming analyses of tissue sections. Proteomic analyses by mass spectrometry remain technically challenging for single cells and phosphoproteomic detection and are costly for routine clinical purposes [7]. In research settings, multiplexed flow cytometry and mass cytometry have been used to examine an expanded set of markers (10 to 45) using single-cell populations. However, multiplexed flow cytometry often encounters limits in the amount of markers it can measure because of spectral overlap. Mass cytometry vaporizes cells during sample preparation, resulting in sample loss [8]. Accordingly, both of these existing methods do not enable isolating a rare cell of interest or performing concurrent genetic analyses once samples are used for proteomic analyses.

Hence, there remains a need for compositions and methods for simultaneous detection of a large number of target molecules from a sample.

SUMMARY

Embodiments of various aspects described herein are, in part, based on the development of a method that not only allows analysis of hundreds of proteins from a limited amount of sample, e.g., minimally invasive fine-needle aspirates (FNAs), which contain much smaller numbers of cells than core biopsies, but also preserves genetic material from the same sample to enable simultaneous measurements of proteins and genetic materials (e.g., DNA, RNA, and microRNAs). In particular, the method relies on DNA-barcoded antibody sensing, where barcodes-single strands of DNA- can be photocleaved and detected using fluorescent complementary probes without any amplification steps, and is referred to as an antibody barcoding with photocleavable DNA (ABCD) platform herein. To demonstrate the capability of the ABCD platform, inventors isolated cancer cells within the FNAs of patients and exposed these cells to a mixture of about 90 DNA-barcoded antibodies, covering the hallmark processes in cancer (for example, apoptosis and DNA damage). The inventors discovered that the single-cell protein analysis of the patients' FNAs showed high intra-tumor heterogeneity, indicating the ability of the ABCD platform to perform protein profiling on rare single cells, including, but not limited to circulating tumor cells. Further, the inventors discovered that patients who showed identical histopathology yet showed patient heterogeneity in proteomic profiling, indicating the ability of the ABCD platform to identify personalized targets for treatment. By profiling and clustering protein expression in patients' samples, the inventors also showed use of the ABCD platform to monitor and predict treatment response in patients receiving chemotherapy, e.g., kinase inhibitors. The protein analysis determined by the ABCD platform is scalable and can be extended to detect other target molecules, e.g., metabolites and lipids. Accordingly, various aspects described herein provide for methods, systems and kits for detecting and/or quantifying a plurality of target molecules from a sample, as well as their uses thereof in various applications, e.g., diagnosis, prognosis, personalized treatment, and/or treatment monitoring.

In one aspect, provided herein is a method for detecting a plurality of target molecules in a sample. The method comprises (a) contacting a sample with a composition comprising a plurality of target probes, wherein each target probe in the plurality comprises: (i) a target-binding molecule that specifically binds to a target molecule in the sample; (ii) an identification nucleotide sequence that identifies the target-binding molecule; and (iii) a cleavable linker between the target-binding molecule and the identification nucleotide sequence; (b) releasing the identification nucleotide sequences from the bound target probes; and (c) detecting signals from the released identification nucleotide sequences, wherein the signals are distinguishable for the identification nucleotide sequences, thereby identifying the corresponding target-binding molecules and detecting a plurality of target molecules in the sample.

Stated another way, the method comprises: (a) forming a plurality of complexes in a sample, each complex comprising a target molecule and a target probe bound thereto, wherein the target probe comprises (i) a target-binding molecule that specifically binds to the target molecule present in the sample; (ii) an identification nucleotide sequence that identifies the target-binding molecule; and (iii) a cleavable linker between the target-binding molecule and the identification nucleotide sequence; (b) releasing the identification nucleotide sequences from the complex; and (c) detecting signals from the released identification nucleotide sequences, wherein the signals are distinguishable for the identification nucleotide sequences, thereby identifying the corresponding target-binding molecules and detecting a plurality of target molecules in the sample. In some embodiments, the cleavable linker is not pre-hybridized (e.g., by basepairing) to any portion of the identified nucleotide sequences.

In some embodiments, e.g., cell assay, each complex comprising a target molecule and a target probe bound thereto does not require two or more target probes of different kinds bound to the same target molecule, where each of the target probes binds to a different region of the same target molecule. For example, each complex does not require both a first target probe binding to a first region of a target molecule, and a second target probe binding to a second region of the same target molecule. Stated another way, in some embodiments, a single target probe as described herein binding to a target molecule is sufficient for enablement of the methods described herein. In these embodiments, the method described herein does not require another target probe binding to the same target molecule for attachment to a solid substrate (e.g., a bead).

In some embodiments, the method can further comprise separating unbound target probes from target probes that are bound to the target molecules in the sample.

The signals from the released identification nucleotide sequences can be detected by various methods known in the art, including, but not limited to sequencing, quantitative polymerase chain reaction (PCR), multiplexed (PCR), mass cytometry, fluorophore-inactivated multiplexed immunofluorescence, hybridization-based methods, fluorescence hybridization-based methods, imaging, and any combinations thereof. In some embodiments, the signals from the released identification nucleotide sequences can be determined by electrophoresis-based methods. In some embodiments, the signals from the released identification nucleotide sequences are not determined by electrophoresis-based methods.

In some embodiments, the signals from the released identification nucleotide sequences can be detected by hybridization-based methods. For example, in some embodiments, the method can further comprise, prior to the detecting in (c), coupling the released identification nucleotide sequences from (b) to a detection composition comprising a plurality of reporter probes. Each reporter probe in the plurality can comprise (i) a first target probe-specific region that is capable of binding a first portion of the identification nucleotide sequence; and (ii) a detectable label that identifies the reporter probe. In these embodiments, signals from the respective detectable labels of the reporter probes that are coupled to the released identification nucleotide sequences can be detected accordingly. Since the signals are distinguishable for each respective reporter probes that are bound to the identification nucleotide sequences, target-binding molecules can be correspondingly identified, thereby detecting a plurality of target molecules in the sample.

In some embodiments where reporter probes are used in the methods described herein, the detectable label of the reporter probes can comprise one or more labeling molecules that create a unique signal for each reporter probe. For example, a unique signal can be an optical signal. The optical signal can be a light-emitting signal or a series or sequence of light-emitting signals. In some embodiments, labeling molecules for generation of an optical signal can comprise one or a plurality of a fluorochrome moiety, a fluorescent moiety, a dye moiety, a chemiluminescent moiety, or any combinations thereof.

In some embodiments, the detection composition used in the methods described herein can additionally or alternatively comprise a plurality of capture probes. Each capture probe can comprise (i) a second target probe-specific region that is capable of binding to a second portion of the identification nucleotide sequence; and (ii) an affinity tag. The affinity tag of the capture probe is generally used to permit immobilization of the released identification nucleotide sequences, upon coupling to the detection composition, onto a solid substrate surface. In some embodiments, immobilization of the released identification nucleotide sequences can provide distinguishable spatial signals that identify the capture probes coupled to the released identification nucleotide sequences. Examples of a solid substrate include, but are not limited to, a microfluidic device, a cartridge, a microtiter plate, a tube, and an array.

In some embodiments, the detection method in (d) does not require amplification of the released identification nucleotide sequences, first target probe-specific region, or the second target probe-specific region. Amplification-free detection methods can minimize any bias or errors introduced during amplification, e.g., due to varying amplification efficiencies among the nucleotide sequences.

In some embodiments, identification nucleotide sequences of the target probes described herein can be selected or designed such that they do not cross-react with any nucleic acid sequence in a genome of a subject, whose sample is being evaluated. Thus, the identification nucleotide sequences used to detect target molecules from a subject's sample can be selected or designed based on nucleotide sequences of a species or genus that is different from the subject. By way of example only, in some embodiments, the identification nucleotide sequences for use in an animal's sample (e.g., a mammal such as a human) can be derived from a plant genome. In one embodiment, the identification nucleotide sequences for use in a human's sample can be derived from a potato genome. In some embodiments, the identification nucleotide sequences can have sequences selected from Table 2 (SEQ ID NO: 1 to SEQ ID NO: 110), or a fragment thereof.

Generally, identification nucleotide sequences of the target probes can have any sequence length and can vary depending on a number of factors, including, but not limited to detection methods, and/or the number of target molecules to be detected. For example, in some embodiments, the length of the identification nucleotide sequences can increase to provide sufficient identification of a large number of target molecules in a sample. In some embodiments where a hybridization-based method is used to detect identification nucleotide sequences, the identification nucleotide sequences can have a length sufficient to provide reliable binding to complementary reporter probes and to generate detectable signals. In some embodiments, the identification nucleotide sequences can have a length of about 30-100 nucleotides. In some embodiments, the identification nucleotide sequences can have a length of about 70 nucleotides.

The cleavable linker coupling a target-binding molecule to an identification nucleotide sequence in a target probe can permit release of the identification nucleotide sequence from the target probe upon binding to a target molecule such that the released identification nucleotide sequence can then be detected. Cleavable linkers are known in the art, of which examples include, but are not limited to the ones that are sensitive to an enzyme, pH, temperature, light, shear stress, sonication, a chemical agent (e.g., dithiothreitol), or any combination thereof. In some embodiments, the cleavable linker can be sensitive to light and enzyme degradation.

In some embodiments, the cleavable linker does not comprise a polynucleotide sequence (e.g., a single-stranded polynucleotide sequence) that is complementary (for base-pairing) to at least a portion of the identification nucleotide sequence. That is, in these embodiments, the identification nucleotide sequence is not released from the complex by detaching from the complementary polynucleotide sequence coupled to a target-binding molecule. Accordingly, in some embodiments, a target probe comprises (i) a target-binding molecule that specifically binds to the target molecule present in the sample; (ii) an identification nucleotide sequence that identifies the target-binding molecule; and (iii) a cleavable, non-hybridizable linker between the target-binding molecule and the identification nucleotide sequence.

In some embodiments, the cleavable, non-hybridizable linkers can be selected from the group consisting of hydrolyzable linkers, redox cleavable linkers, phosphate-based cleavable linkers, acid cleavable linkers, ester-based cleavable linkers, peptide-based cleavable linkers, photocleavable linkers, and any combinations thereof. In some embodiments, the cleavable linker can comprise a disulfide bond, a tetrazine-trans-cyclooctene group, a sulfhydryl group, a nitrobenzyl group, a nitoindoline group, a bromo hydroxycoumarin group, a bromo hydroxyquinoline group, a hydroxyphenacyl group, a dimethozybenzoin group, or any combinations thereof.

In some embodiments, the cleavable, non-hybridizable linker can comprise a photocleavable linker. Any art-recognized photocleavable linker can be used for the target probes described herein. Exemplary photocleavable linker is selected from the group consisting of molecules (i)-(xiv) and any combinations thereof, wherein the chemical structures of the molecules (i)-(xiv) are shown as follows:

(i)

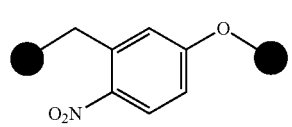

(ii)

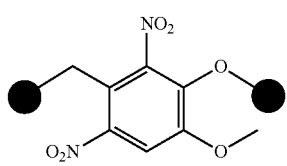

-continued (iii)

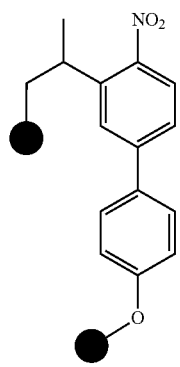

(iv)

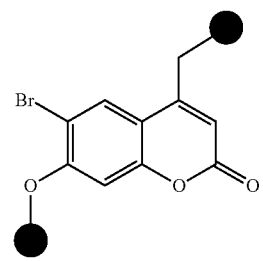

(v)

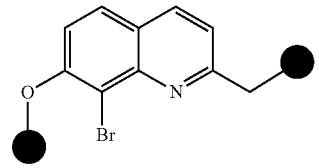

(vi)

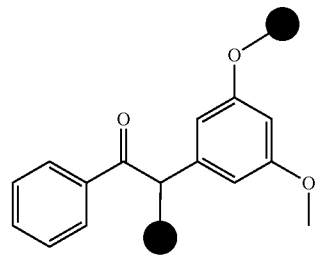

(vii)

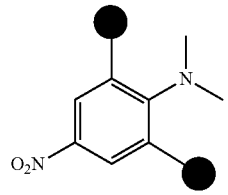

(viii)

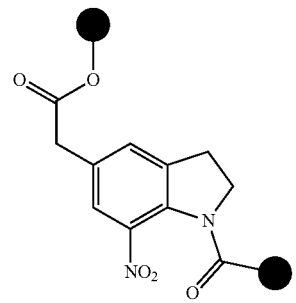

-continued

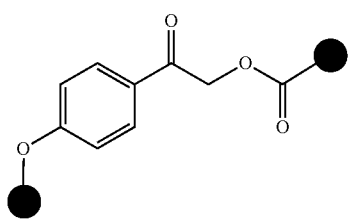
(xi)

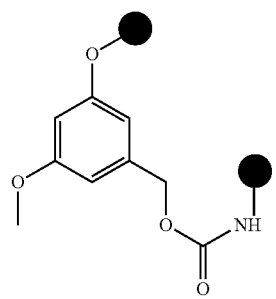
(x)

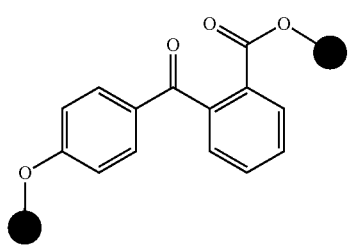
(xi)

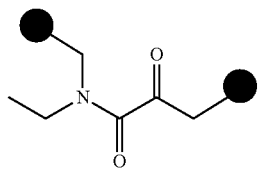
(xii)

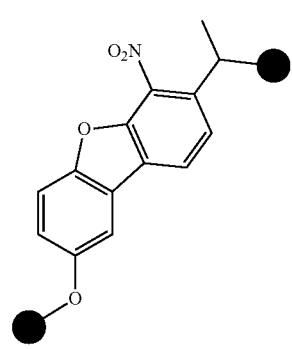
(xiii)

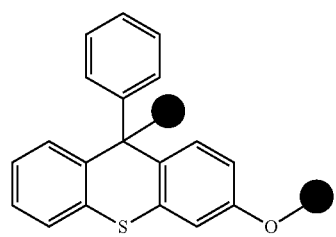
(xiv)

-continued

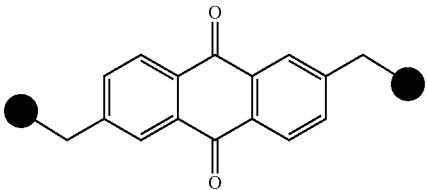
(xv)

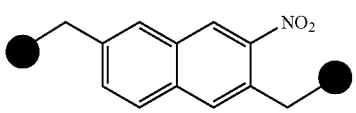
(xvi)

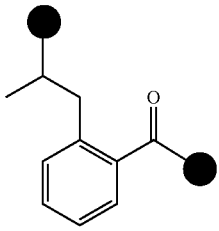
(xvii)

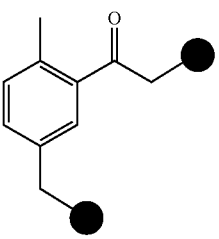
(xviii)

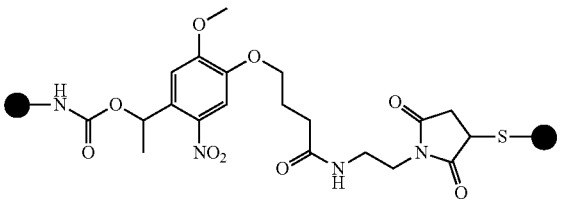
(xiv)

where each of the black dots in each molecule represents a connecting or coupling point that connects, directly or indirectly, to a target-binding molecule described herein or an identification nucleotide sequence described herein. The connecting point can be a bond, or comprise an atom, a molecule, and/or a linker described herein. In some embodiments, the connecting point is a bond.

In some embodiments, the photocleavable linker can comprise the molecule (xiv).

In some embodiments where a photocleavable linker is used, the identification nucleotide sequences can be released from the bound target probes by exposing the bound target probes to a light of a specified wavelength. In some embodiments, ultraviolet light can be used to release identification nucleotide sequences from bound target probes.

In some embodiments, the method can further comprise, prior to contacting the sample with target probes, separating target cells from interfering cells in the sample. Methods to separate target cells from interfering cells are known in the sample, e.g., based on cell surface proteins that distinguish target cells from interfering cells. By way of example only, target cells or interfering cells can be labeled with ligands that target specific cells of interests (e.g., cell-specific antibodies). In some embodiments where the cell-specific ligands are fluorescently labeled, the labeled cells can then be sorted, e.g., by flow cytometry. Alternatively, if the cell-specific ligands are attached to magnetic particles, the labeled cells with bound magnetic particles can be isolated from the sample by magnetic separation.

Target cells can be prokaryotic or eukaryotic, including microbes (e.g., bacteria, fungus, virus, and/or pathogens. In some embodiments, the target cells can comprise normal cells, diseased cells, mutant cells, germ cells, somatic cells, and/or rare cells. Example of rare cells include, without limitations, circulating tumor cells, fetal cells, stem cells, immune cells, clonal cells, and any combination thereof. In some embodiments, the target cells can comprise tumor cells. In some embodiments, the tumor cells can be derived from a tissue biopsy, a fine aspirate or a liquid biopsy (e.g., peritoneal, pleural, cerebrospinal fluid, and/or blood), a mucosal swab, a skin biopsy, a stool sample, or any combinations thereof. In some embodiments, whole cells and/or cell lysates can be used in the methods and/or systems described herein to detect a plurality of target molecules in a sample. In some embodiments, the whole cells can be obtained from a fixed cell or tissue sample.

Typically, signals detected from the identification nucleotide sequences of the target probes corresponding to target molecules can be compared to a control reference to account for any non-specific binding. Accordingly, in some embodiments, the composition added to the sample can further comprise a plurality of control probes. Each control probe in the plurality can comprise: (i) a control-binding molecule that specifically binds to one control molecule in the sample; (ii) an identification control sequence that identifies the control-binding molecule; and (iii) a cleavable linker between the control-binding molecule and the identification control sequence. The control-binding molecule can bind to a control protein present in a sample. Non-limiting examples of control proteins include housekeeping proteins, control IgG isotypes, mutant non-functional or non-binding proteins, and any combinations thereof.

Signals from the control probes can then be used to threshold the signals from the target probes. Accordingly, in some embodiments, the method can further comprise thresholding the target signals. In some embodiments, the target signals can be thresholded on the basis of nonspecific binding. In one embodiment, the threshold is generally set to be greater than that of the signals from the non-specific binding. In some embodiments, the threshold can be determined by using standard deviation and measurement error from at least one or more control proteins.

In some embodiments, the method can further comprise quantifying the signals (e.g., signals that are above the pre-determined threshold) by normalizing the signals associated with the target probes by the signals associated with the control probes. In one embodiment, the signals is quantified and expressed as number of identification nucleotide sequences detected per target-binding agent In some embodiments, the method can further comprising extracting a nucleic acid molecule for the same sample for a nucleic acid analysis. Examples of a nucleic acid detection and analysis can include, but are not limited to sequencing, quantitative polymerase chain reaction (PCR), multiplexed PCR, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing, nanopore DNA sequencing, sequencing by hybridization, sequencing with mass spectrometry, microfluidic Sanger sequencing, microscopy-based sequencing techniques, RNA polymerase (RNAP) sequencing, or any combinations thereof.

While the methods described herein are described in the context where the identification nucleotide sequences are released from bound target probes before detection, in some embodiments, the identification nucleotide sequences do not need to be released from the bound target probes. Accordingly, in some embodiments, the methods described herein can also apply when the identification nucleotide sequences remain bound to target probes during detection.

Various embodiments of the methods described herein can be carried out in one or more functional modules in a system or a computer system as described herein. Accordingly, another provided herein relates to a system for multiplexed detection of a plurality of target molecules in a sample. For example, the system comprises:

(a) at least one sample processing module comprising instructions for receiving said at least one test sample comprising a sample and a plurality of target probes, wherein each target probe in the plurality comprises:
  i. a target-binding molecule that specifically binds to one target molecule in the sample;
  ii. an identification nucleotide sequence that identifies the target-binding molecule; and
  iii. a cleavable linker between the target-binding molecule and the identification nucleotide sequence; and
wherein the at least one sample processing module further comprises instructions for releasing the identification nucleotide sequences from the target probes that are bound to target molecules in the sample;

(b) a signal detection module comprising instructions for detecting signals from the released identification nucleotide sequences;

(c) at least one data storage module comprising instructions for storing the detected signals from (b) and information associated with identification nucleotide sequences of the target probes;

(d) at least one analysis module comprising instructions for determining the presence of one or more target molecules in the sample based on the detected signals; and (e) at least one display module for displaying a content based in part on the analysis output from said analysis module, wherein the content comprises a signal indicative of the following: (i) the presence of one or more target molecules in the sample, (ii) the absence of one or more target molecules in the sample, and/or (iii) expression levels of one or more target molecules in the sample.

In some embodiments, the analysis module can further comprise instructions for (i) identifying the detectable probes of the reporter probes that correspond to the detected signals; (ii) identifying the identification nucleotide sequences of the target probes that correspond to the detectable probes based on the first target probe-specific regions of the reporter probes; and (iii) identifying the target-binding molecules that correspond to the identification nucleotide sequences, thereby determining the presence of one or more target molecules in the sample.

In some embodiments, the content can be displayed on a computer display, a screen, a monitor, an email, a text message, a website, a physical printout (e.g., paper), or provided as stored information in a data storage device.

Kits, e.g., for multiplexed detection of a plurality of different target molecules from a sample, are also provided herein. In some embodiments, the kit comprises:

(a) a plurality of target probes, wherein each target probe in the plurality comprises:
  i. a target-binding molecule that specifically binds to one target molecule in the sample;
  ii. an identification nucleotide sequence that identifies the target-binding molecule; and
  iii. a cleavable linker between the target-binding molecule and the identification nucleotide sequence; and
(b) a plurality of reporter probes, wherein each reporter probe comprises:
  i. a first target probe-specific region that is capable of binding a first portion of the identification nucleotide sequence; and
  ii. a detectable label that identifies the reporter probe.

In some embodiments, the detectable label of the reporter probes can comprise one or more labeling molecules that create a unique signal for each reporter probe. An exemplary unique signal can be an optical signal. The optical signal can comprise one or a series or a sequence of light-emitting signals. In these embodiments, non-limiting examples of the labeling molecules include fluorochrome moieties, fluorescent moieties, dye moieties, chemiluminescent moieties, and any combinations thereof.

In some embodiments, the kit can further comprise a plurality of capture probes, wherein each capture probe comprises (i) a second target probe-specific region that is capable of binding a second portion of the identification nucleotide sequence; and (ii) an affinity tag.

In some embodiments, the kit can further comprise a plurality of control probes, wherein each control probe in the plurality comprises:
  (i) a control-binding molecule that specifically binds to one control molecule in the sample;
  (ii) an identification control sequence that identifies the control-binding molecule; and
  (iii) a cleavable linker between the control-binding molecule and the identification control sequence.

In some embodiments, the kit can further comprise at least one reagent for use in one or more embodiments of the methods or systems described herein. Reagents that can be provided in the kit can include at least one or more of the following: a hybridization reagent, a purification reagent, an immobilization reagent, an imaging agent, a cell permeabilization agent, a blocking agent, a cleaving agent for the cleavable linker, primers for nucleic acid detection, nucleic acid polymerase, and any combinations thereof.

In some embodiments, the kit can further include a device for use in one or more embodiments of the methods and/or systems described herein. In some embodiments, the device can comprise a surface for immobilization of the capture probes upon coupling to the identification nucleotide sequences. In some embodiments, the device can comprise a microfluidic device for separating target cells from interfering cells as described herein.

The methods, systems and kits described herein can be used to detect any target molecules present in a sample provided that appropriate target-binding agents are used in the target probes employed in the methods described herein. Exemplary target molecules which can be detected by the methods, systems and kits described herein include, but are not limited to proteins, peptides, metabolites, lipids, carbohydrates, toxins, growth factors, hormones, cytokines, cells (e.g., eukaryotic cells, prokaryotic cells, and microbes), and any combinations thereof. In some embodiments, the target molecules to be detected can be extracellular or secreted molecules. In some embodiments, the target molecules to be detected can be intracellular, e.g., cytoplasmic molecules or nuclear molecules.

To detect intracellular molecules (e.g., intracellular proteins), the target cells in the sample can be permeabilized or lysed such that target probes can contact the target intracellular molecules for further processing and analysis.

In some embodiments, the methods, systems and kits described herein can enable measurements of at least two target molecules of different types. For example, the methods, systems, and kits described herein can be used to measure, for example, nucleic acid molecules and proteins, or proteins and metabolites, or proteins and lipids. The measurements of at least two target molecules of different types can be performed simultaneously or sequentially. In another embodiment, by releasing identification nucleotide sequences from bound target molecules (e.g., proteins), genetic material and the identification nucleotide sequences can be concurrently extracted from a single sample, enabling analyses of protein-DNA-RNA interrelationships.

By way of example only, the methods, systems and kits described herein applied to a sample can preserve genetic materials in a sample while detecting other non-genetic target materials in the same sample. Accordingly, in some embodiments, the methods, systems and/or kits described herein for detection of non-genetic target molecules (e.g., but not limited to proteins) can be used in combination with a nuclei acid analysis for genetic materials, for example, to study the non-genetic target molecules (e.g., but not limited to proteins) that interact with genetic materials or genetic regulatory elements. In these embodiments, the methods and systems described herein for detecting a plurality of target molecules in a sample as described herein can further comprise extracting a nucleic acid molecule from the same sample in which target molecules are to be detected. In some embodiments, the methods and systems described herein can further comprise subjecting the extracted nucleic acid molecule to a nucleic acid analysis. Various methods can be used for nucleic acid analysis, including, but not limited to sequencing, next generation sequencing, quantitative polymerase chain reaction (PCR), multiplexed PCR, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing, nanopore DNA sequencing, sequencing by hybridization, sequencing with mass spectrometry, microfluidic Sanger sequencing, microscopy-based sequencing techniques, RNA polymerase (RNAP) sequencing, fluorescence hybridization-based technology (e.g., but not limited to nanoString nCounter® hybridization technology), any art-recognized nucleic acid detection methods, or any combinations thereof.

In some embodiments, after a sample and/or non-genetic target molecules have been labeled with a plurality of target probes described herein, the identification nucleotide sequences of the target probes can be released from the bound non-genetic target molecules simultaneously with extraction of nucleic acid molecules (cells' genetic materials) from the same labeled sample. In these embodiments, both the nucleic acid molecules of interest and the identification nucleotide sequences can be detected simultaneously in a single sample mixture. In one embodiment, both the nucleic acid molecules of interest and the identification nucleotide sequences can be detected simultaneously in a single sample mixture using nanoString nCounter® analysis system, for example, as described in U.S. Pat. No. 8,415, 102, the content of which is incorporated herein by reference. Other art-recognized methods for nucleic acid analyses as described herein can also be used for simultaneous detection of both nucleic acid molecules of interest (cells' genetic materials) and released identification nucleotide sequences from bound non-genetic target molecules.

In alternative embodiments, nucleic acid molecules can be extracted from a first portion of a sample, while non-genetic target molecules can be independently derived or obtained from a second portion of the same sample. In these embodiments, the nucleic acid molecules of interest and the non-genetic target molecules can be detected separately to determine expression levels of the nucleic acid molecules (cells' genetic materials) of interest and non-genetic target molecules (e.g., but not limited to proteins) in the same sample. The nucleic acid molecules of interests can be subjected to any art-recognized nucleic acid analysis, while the non-genetic target molecules can be detected through detecting and identifying the corresponding identification nucleotide sequences released from the target probes using the methods, systems and/or kits described herein.

In some embodiments, the methods, systems and kits described herein can be adapted to measure proteins and nucleic acid molecules in the same sample. For example, the proteins can be detected by one or more embodiments of the target probes described herein, while the nucleic acid molecules can be detected by any methods known in the art, thereby creating an integrated expression profiling for the sample, which can provide information on interaction between the proteins and the nucleic acid molecules, e.g., genetic regulatory elements such as microRNAs.

The methods, systems and kits described herein can be used in any applications where detection of a plurality of target molecules in a sample is desirable. For example, a sample can be a biological sample, or a sample from an environmental source (e.g., water, soil, food products, and/or ponds).

The inventors have demonstrated that, in one embodiment, an antibody barcoding with photocleavable DNA (ABCD) platform described herein can enable analysis of hundreds of proteins from a single cell or a limited number of cells, e.g., from minimally invasive fine-needle aspirates (FNAs). Accordingly, samples amenable to the methods described herein can comprise less than 500 cells or fewer. In some embodiments, the sample can be a single-cell sample. In some embodiments, the sample can comprise cells isolated from a fine-needle aspirate.

Where the sample is a biological sample, in some embodiments, the methods, systems and kits described herein can be used in personalized treatment. For example, a biological sample can be collected from an individual subject who is in need of a treatment for a condition. Using the methods, systems and/or kits described herein, an expression profile of target molecules associated with the subject's condition can be generated to identify one or more therapeutic targets for the subject, thereby identifying a treatment regimen for the subject.

In some embodiments, the methods, systems and kits described herein can be used in monitoring response of a subject to a treatment for his/her condition. For example, biological sample(s) can be collected from the subject prior to and/or over the course of the treatment. Using the methods, systems and/or kits described herein, expression profiles of target molecules associated with the subject's condition before and/or over the course of the treatment can be generated for comparison to determine any changes in expression levels of the target molecules in the subject, thereby monitoring the treatment response in the subject.

In some embodiments, the methods, systems and kits described herein can be used in diagnosing a condition in a subject. For example, a biological sample can be collected from a subject who is at risk for a condition. Using the methods, systems and/or kits described herein, an expression profile of target molecules associated with the condition to be diagnosed can be generated for comparison with one or more reference expression profiles (e.g., corresponding to a normal healthy subject and/or a subject having the condition to be diagnosed), thereby determining whether the subject is at risk for the condition.

BRIEF DESCRIPTION OF THE DRAWINGS

(FIG. 1A) Cells were harvested from cancer patients by FNAs. In this case, a heterogeneous population of EpCAM-positive cancer cells (green) is displayed alongside mesothelial cells (red) with nuclei shown in blue (Hoechst) from an abdominal cancer FNAs. Cancer cells were enriched and isolated via magnetic separation in polydimethylsiloxane (PDMS) microfluidic devices with herringbone channels using both positive (for example, EpCAM+/CK+) and negative (for example, CD45−) selection modes. (FIG. 1B) Cells of interest were incubated with a cocktail of DNA-conjugated antibodies containing a photocleavable linker (FIG. 2A) to allow DNA release after exposure to ultraviolet light. (FIG. 1C) DNA-antibody conjugates released from lysed cells (FIG. 3) were isolated using size separation and IgG pull-down. Released "alien" DNA barcodes were processed with a fluorescent DNA barcoding platform (NanoString). Fluorescent barcodes were hybridized and imaged using a CCD camera. The quantified barcodes were translated to protein expression levels by normalizing to DNA per antibody and housekeeping proteins and subtracting nonspecific binding from control IgGs. A representative profile of SKOV3 ovarian cancer cell lines shows high CD44 and high Her2 expression, characteristic of this cell line.

(FIG. 2A) Various linker strategies were investigated to conjugate DNA to antibodies. In some embodiments, the photocleavable linker (PCL) was selected owing to its better cleavage efficiency compared with DTT, tetrazine-trans-cyclooctene (via click chemistry, linker 1), and Traut's reagent (linker 2). Linker cleavage was tested by measuring released DNA via the NanoString platform. Data are averages of two independent trials. **$P<0.01$, paired t-test. (FIG. 2B) Linking DNA to an antibody via the PCL. The linker was first reacted with the amine (—$NH_2$) groups on the antibody. After excess small molecule was removed, thiolated DNA was added at 10-fold excess to the antibody-linker mix. The final antibody-DNA chimera was purified via both size separation and IgG-specific pulldown. DNA could subsequently be released from the antibody by photocleavage at a specific wavelength (365 nm).

The lysate conditions were tested in duplicate (x-axis) measuring DNA signal (y-axis) and different intracellular proteins (z-axis). The best reaction condition was method B (Proteinase K+ATL lysis buffer), with a 20% increase in signal over methods (Methods A and C).

Figure 4:
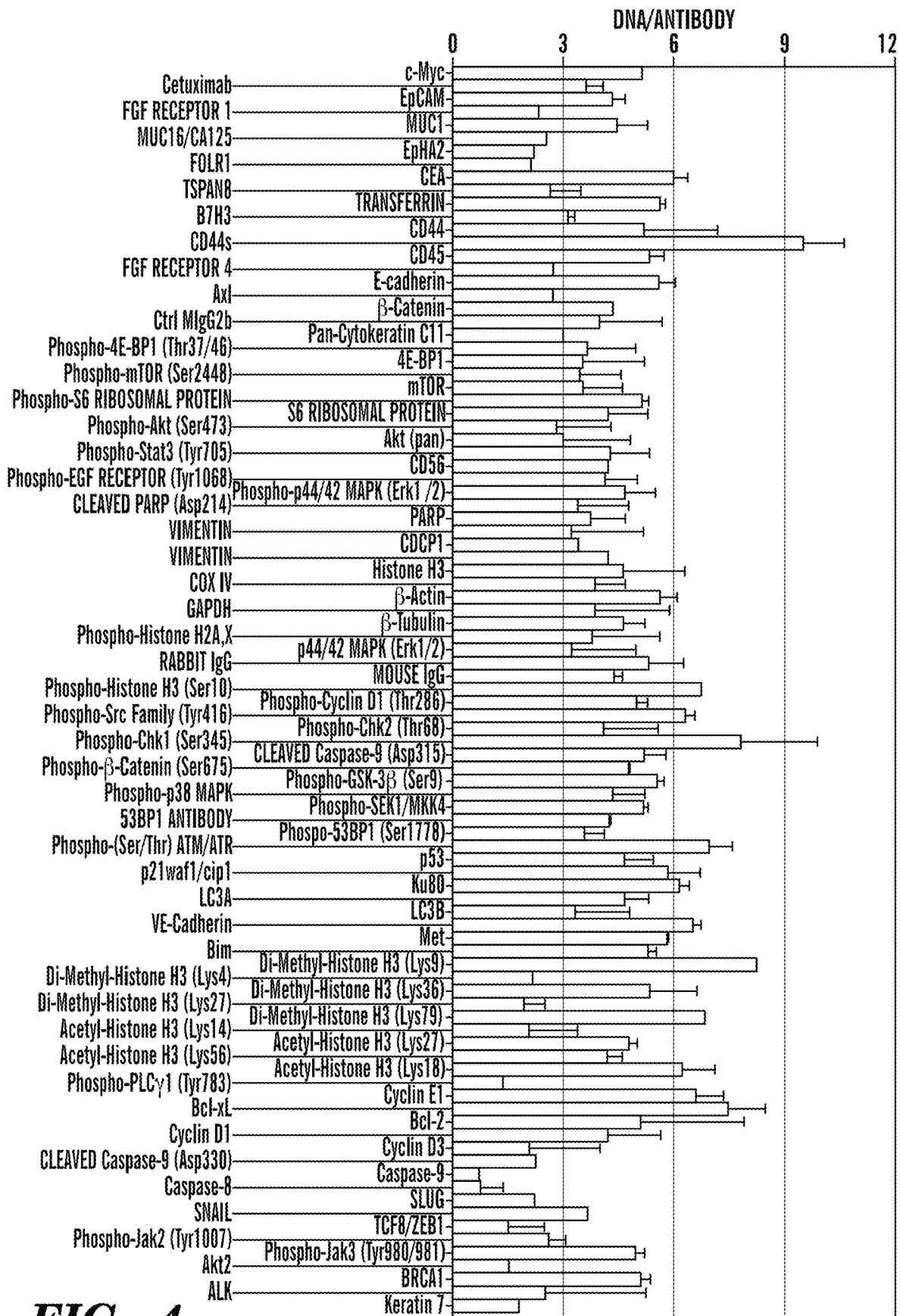

FIG. 4 is a graph showing the readouts of DNA per antibody for each target molecule. The number of alien DNA fragments per antibody was measured by Nanostring method (shown in graph) and independently confirmed by ssDNA quantification and Qubit protein measurement. Data are displayed from triplicate measurements±SEM.

Figure 5:
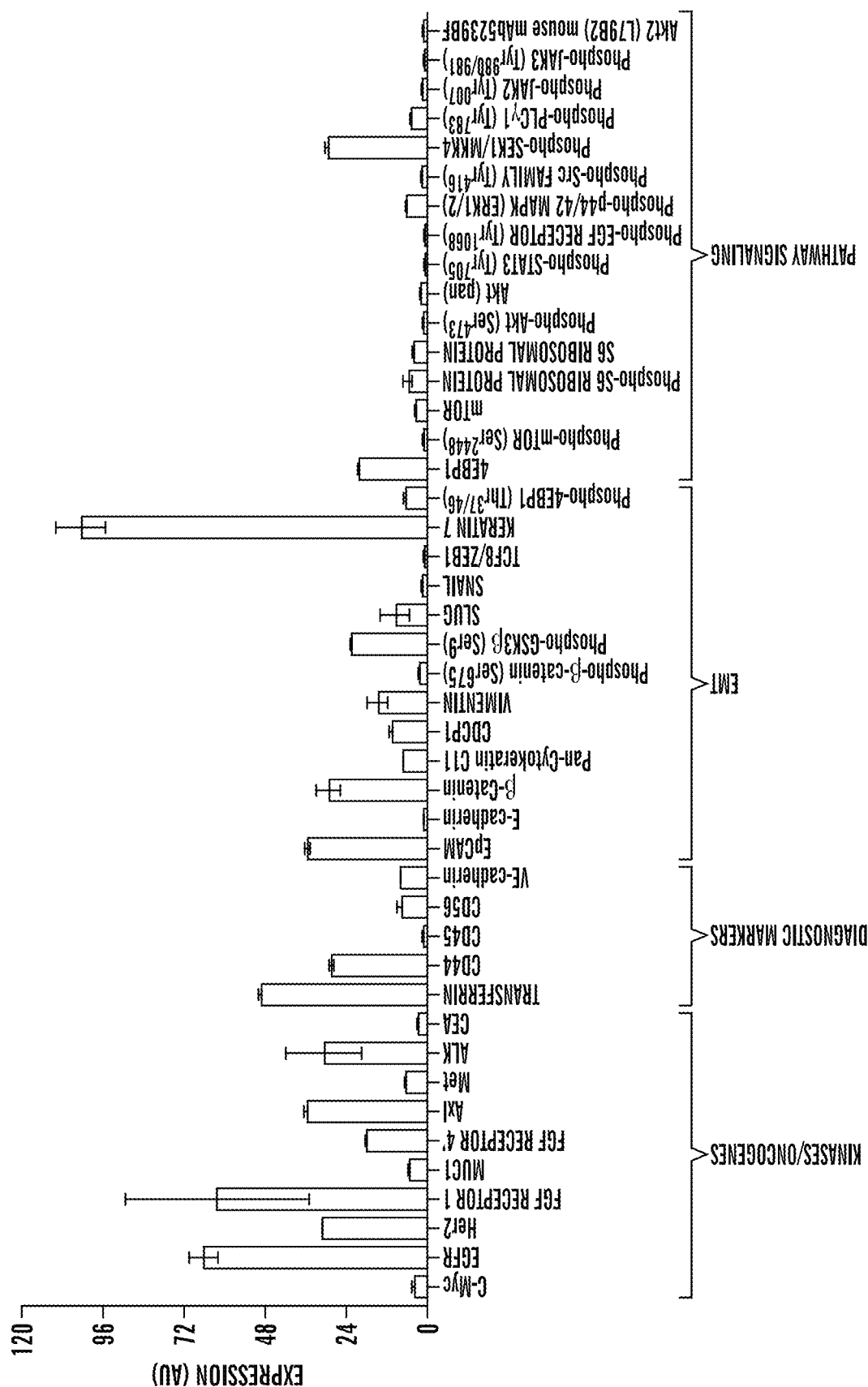
Figure 5:
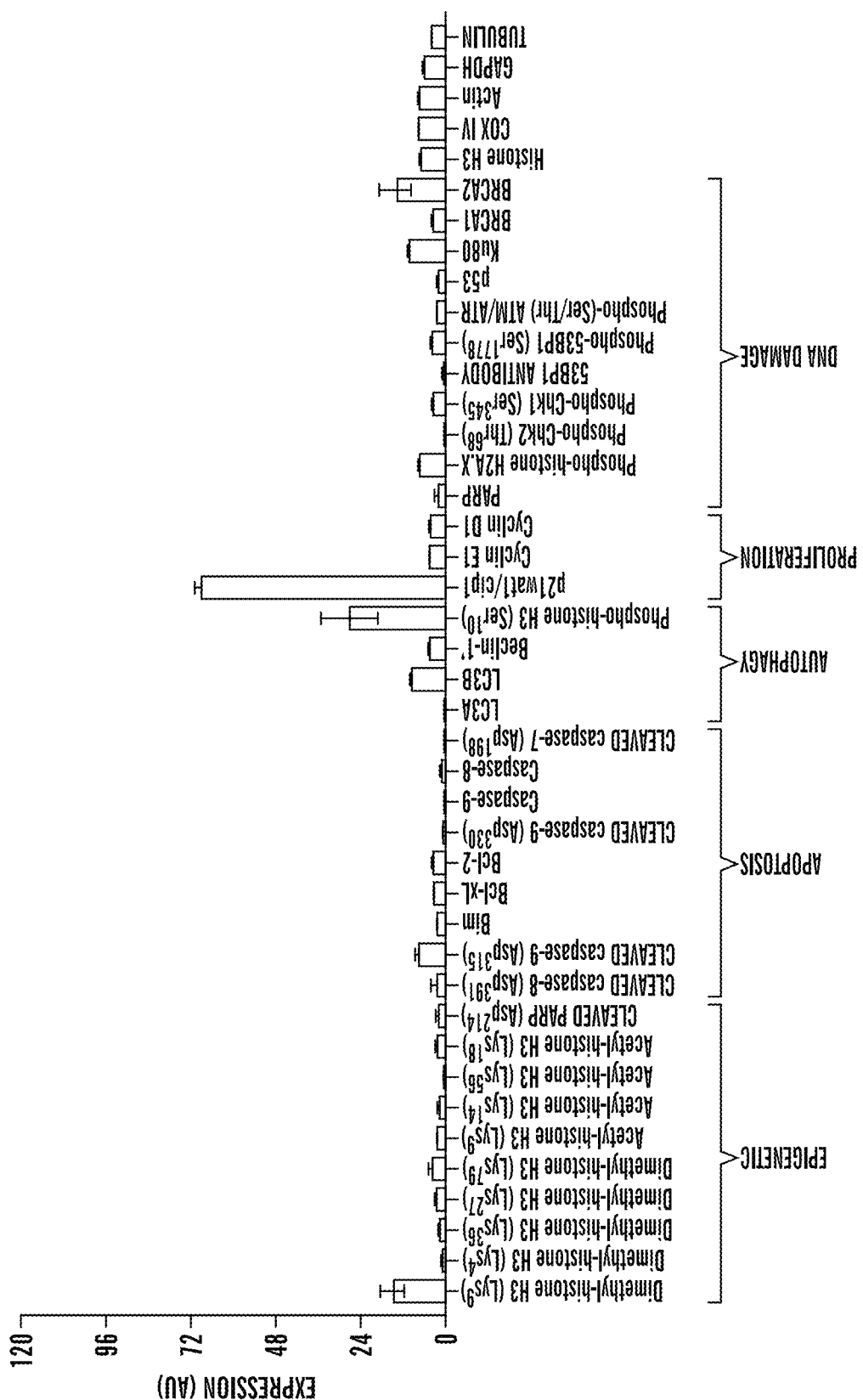

FIG. 5 shows a multiplexed protein profiling of a human breast cancer cell line. Representative example of 88 different antibodies spanning cancer-relevant pathways (color-coded) profiled in triplicate (mean±SEM) on the MDAMB-231 triple-negative breast cancer cell line. DNA counts were converted to protein binding by normalizing to the amount of DNA per antibody. Nonspecific binding from expression of six control IgGs was subtracted, and expression was normalized by housekeeping proteins Cox IV, histone H3, tubulin, actin, and glyceraldehyde-3-phosphate dehydrogenase (GAPDH) (far right). AU, arbitrary units; EMT, epithelial-to-mesenchymal transition.

FIGS. 6A-6B are graphs showing effect of permeabilization schemes on antibody labeling. (FIG. 6A) Methanol and saponin permeabilization were similar for both intracellular and nuclear proteins. Representative examples are graphed, such as phospho-histone H3 (pH3), epithelial cell adhesion molecule (EpCAM), phosphorylated Src (pSRC), and phosphorylated glycogen synthase kinase 3β(pGSK3b). (FIG. 6B) Nonspecific binding was much higher with methanol permeabilization.

Figure 7A:
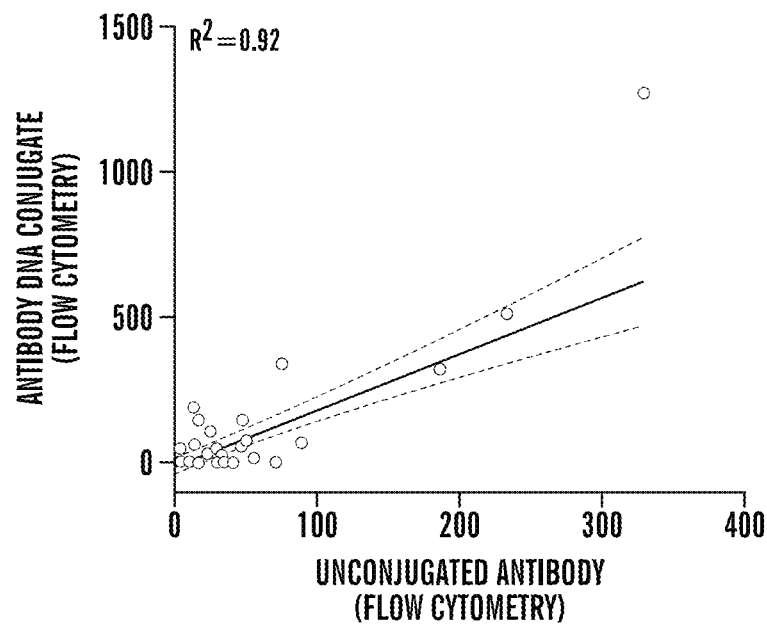
Figure 7B:
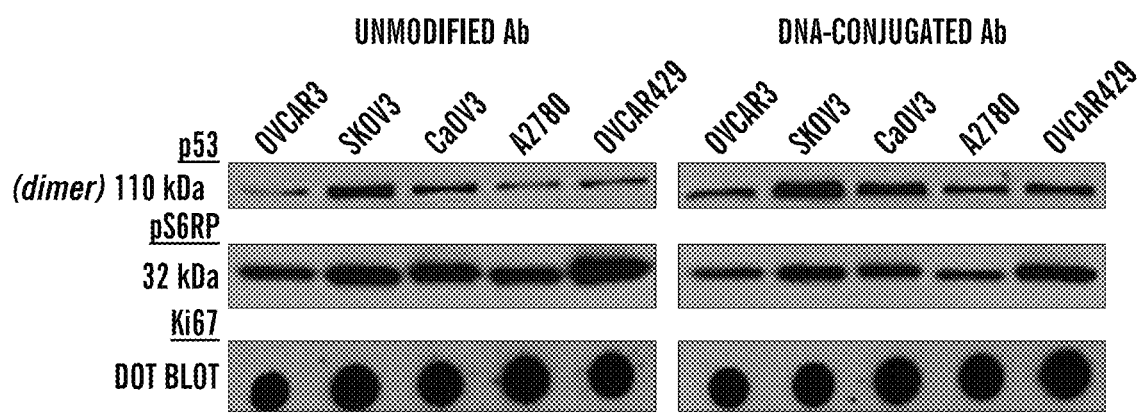

FIGS. 7A-7B are experimental data showing comparison of unmodified antibodies to DNA-antibody conjugates. (FIG. 7A) Antibody-DNA conjugates show good correlation against unconjugated, native antibodies, as determined by flow cytometry. Experiments were performed on multiple cell lines. A representative example is shown with a head-to-head comparison of multiple antibodies on the human SKOV3 cell line ($R^2$=0.92). (FIG. 7B) Protein expression detected in different cell lysates showed similar patterns of expression whether detected by unmodified antibodies or DNA conjugates. This held true for p53 and phospho-S6RP (immunoblotting), and Ki67 (dot blot).

Figure 8C:
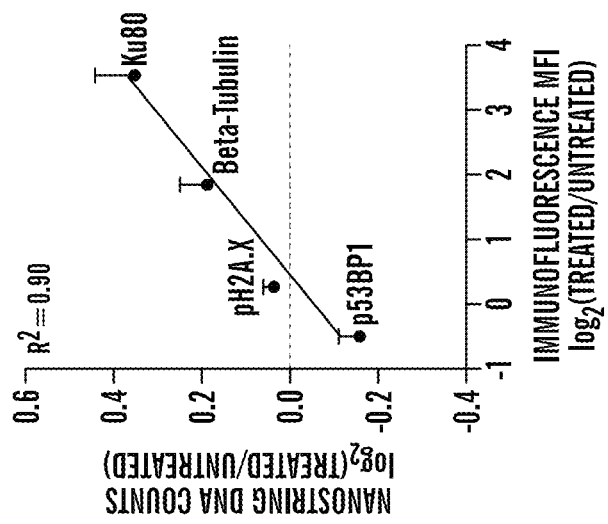
Figure 8B:
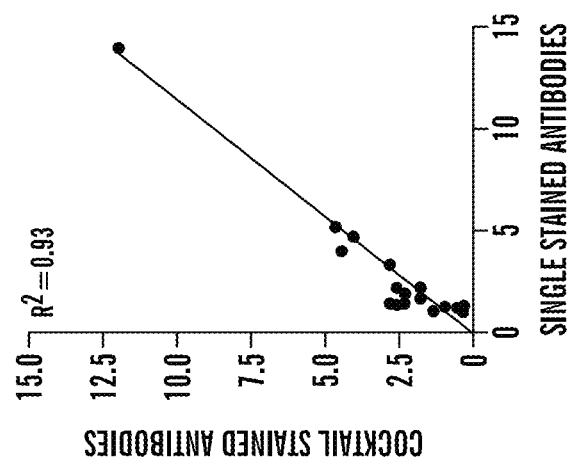
Figure 8A:
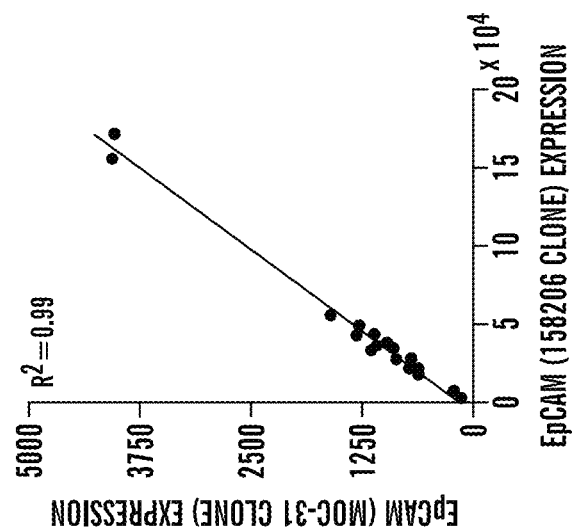

FIGS. 8A-8C show validation data of DNA-antibody conjugates. (FIG. 8A) Concordance between two different antibody clones of EpCAM (MOC-31 and 158206) when conjugated to separate DNA barcodes. The antibodies were assayed across multiple patient samples (n=22). (FIG. 8B) Antibody expression was measured when cell lines were stained with a single antibody as compared to a cocktail (80+ antibodies). Data were collected from 5 antibodies (CD44, EGFR, 53BP1, p-S6RP, rabbit IgG) on 3 different human cell lines (MDA-MB-231, MDA-MB-436, and A431). The experiment was repeated in duplicate and each data point corresponds to one marker on a given cell line. Expression measurements were calculated by normalized DNA counts for the same number of cells. (FIG. 8C) Changes in marker expression before and after treatment were assayed and quantified using both the method in the Examples (ABCD platform) and an independent immunofluorescence screen (standard error is shown from biological triplicate).

Figure 9:
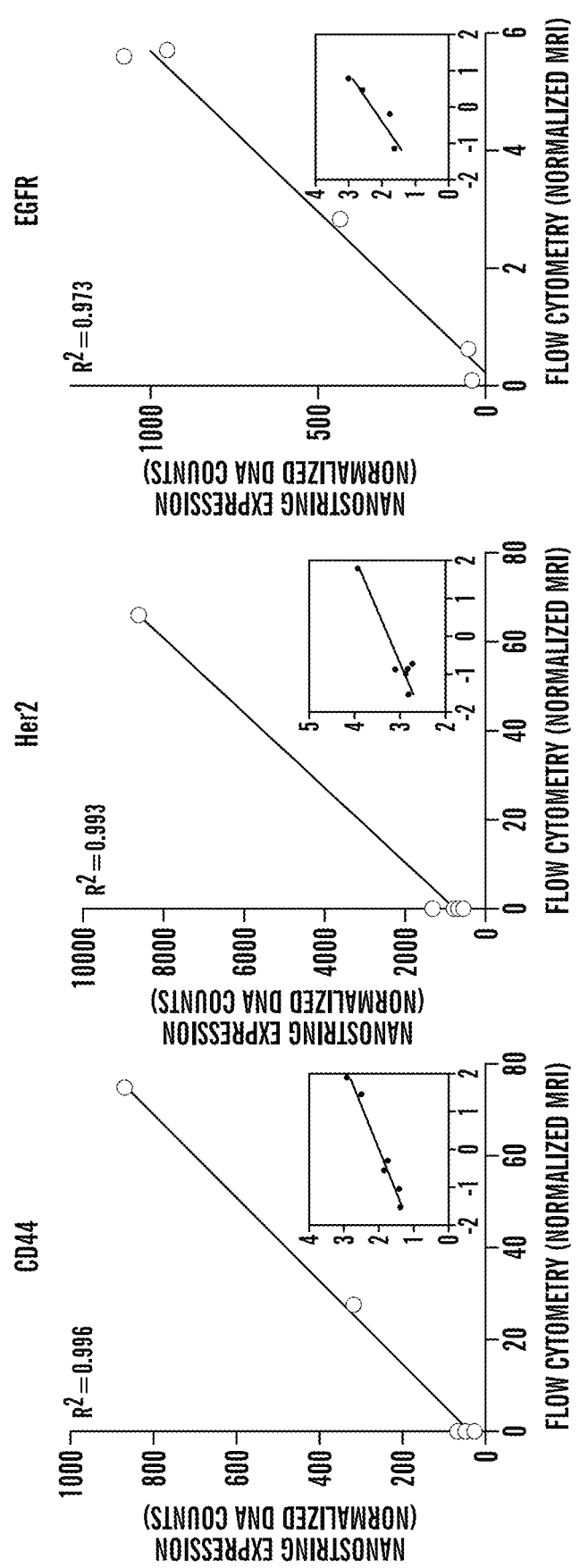
Figure 9:
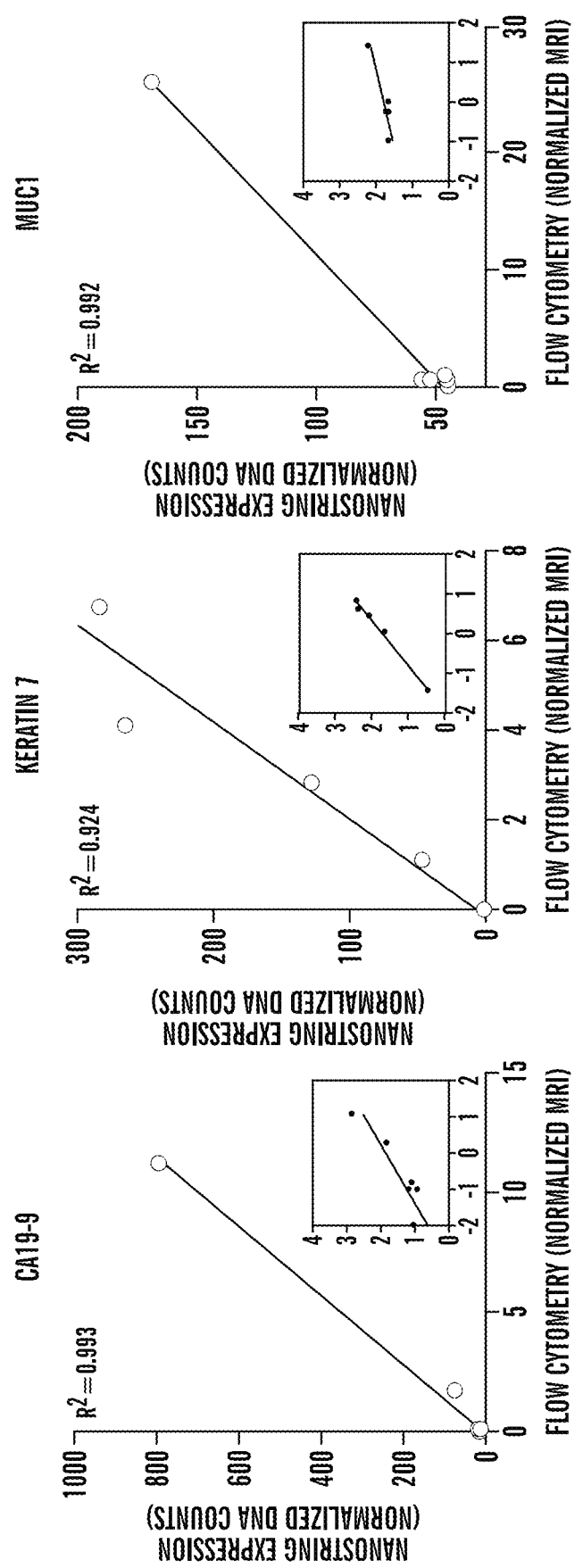

FIG. 9 is a set of graphs showing that protein marker expression correlates with flow cytometry. Multiple markers (CD44, Her2, EGFR, CA19-9, Keratin 7, and Muc 1) were screened across multiple cell lines (SK-OV-3, ES-2, OVCA429, UCI-107, UCI-101, TOV-112D, TOV-21G, and A2780). Each data point represents expression derived from NanoString DNA counts or flow cytometry for a particular cell line. Expression values were normalized by housekeeping proteins GAPDH, tubulin, and actin. Cell lines with measurements below that of the negative control (IgG antibodies) either on flow cytometry or Nanostring were excluded. These measurements were compared to independently performed flow cytometry measurements, which were calculated from the mean fluorescence intensity (signal/background), where the background was the secondary antibody without the primary antibody. The inset shows the log-log plot of the data.

Figure 1A:
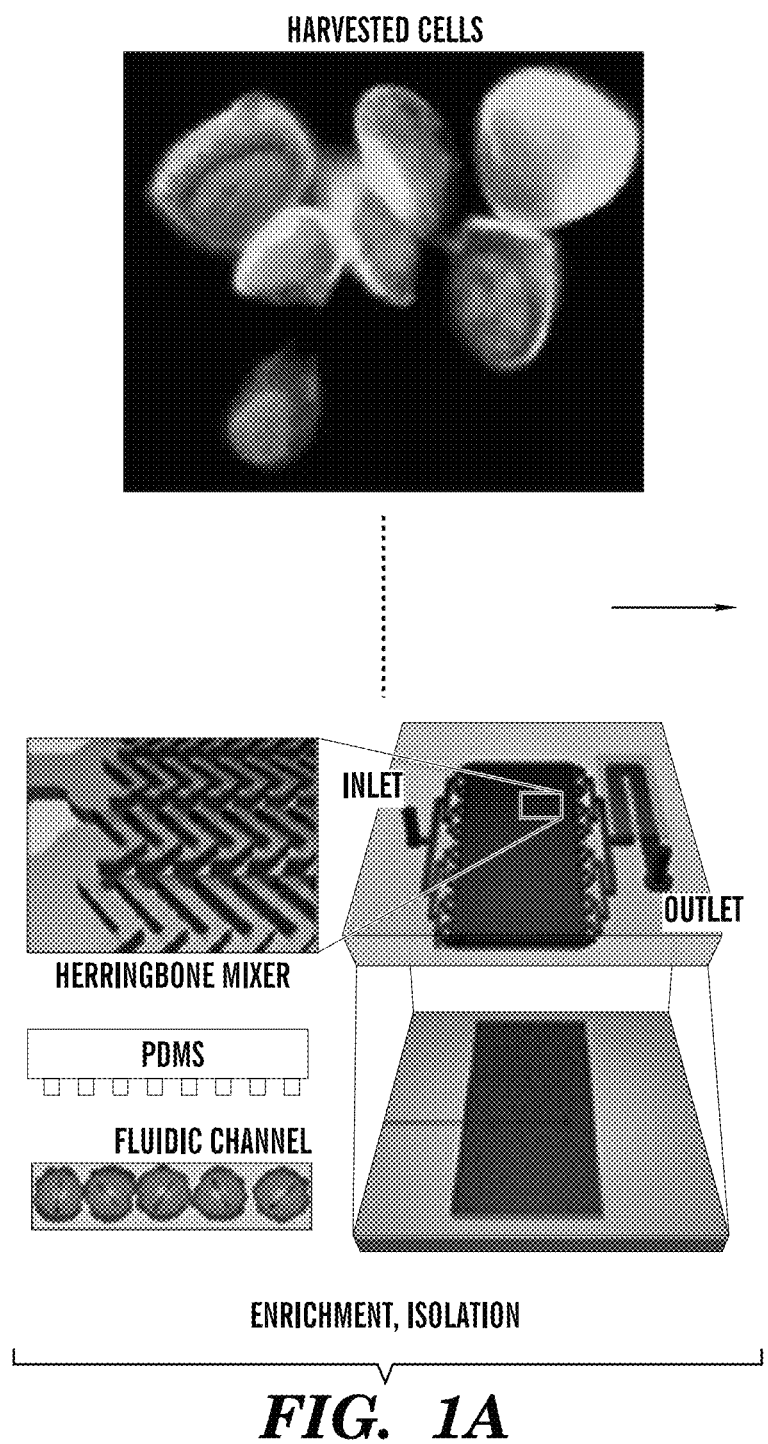
FIGS. 1A-1C shows an exemplary scheme of a multiplexed protein analysis in single cells in accordance with one or more embodiments of the methods described herein.
Figure 1B:
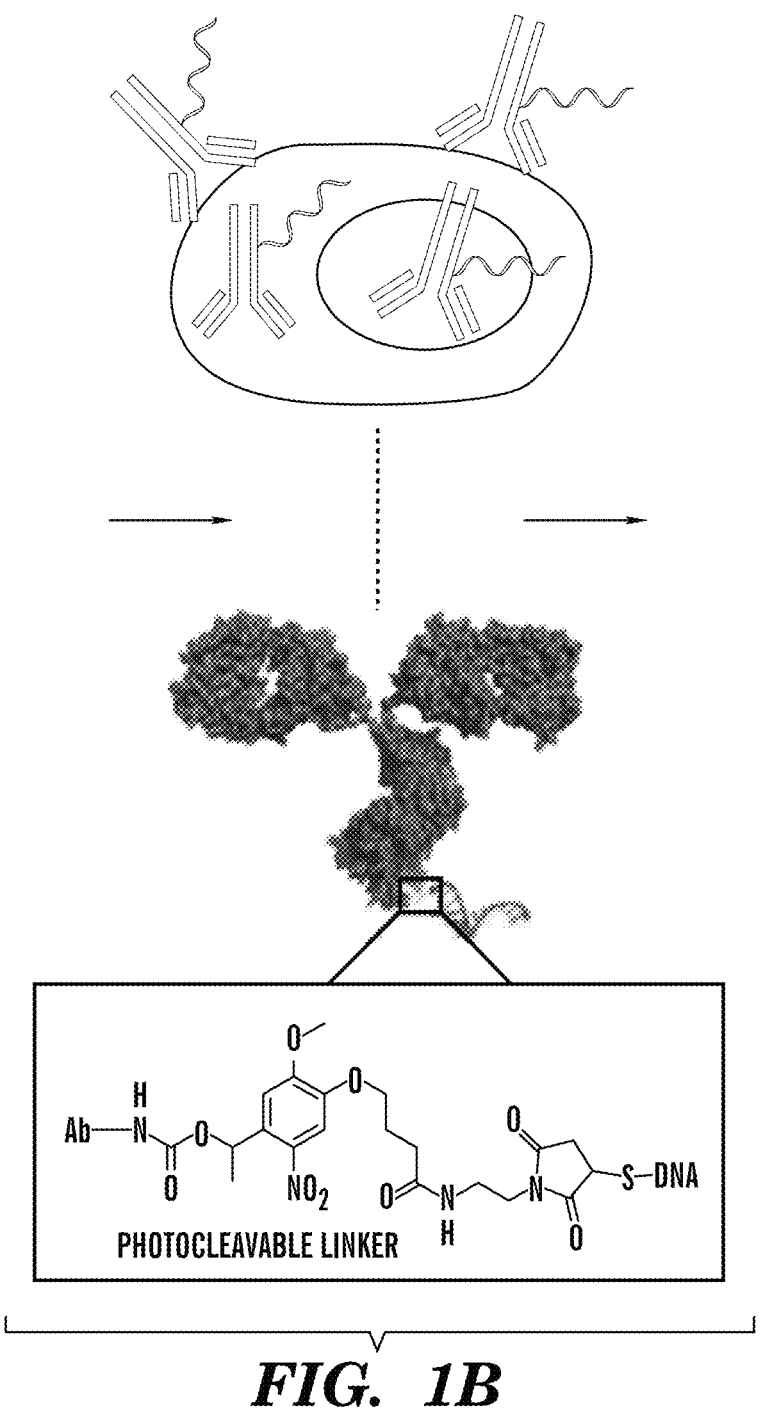
Figure 1C:
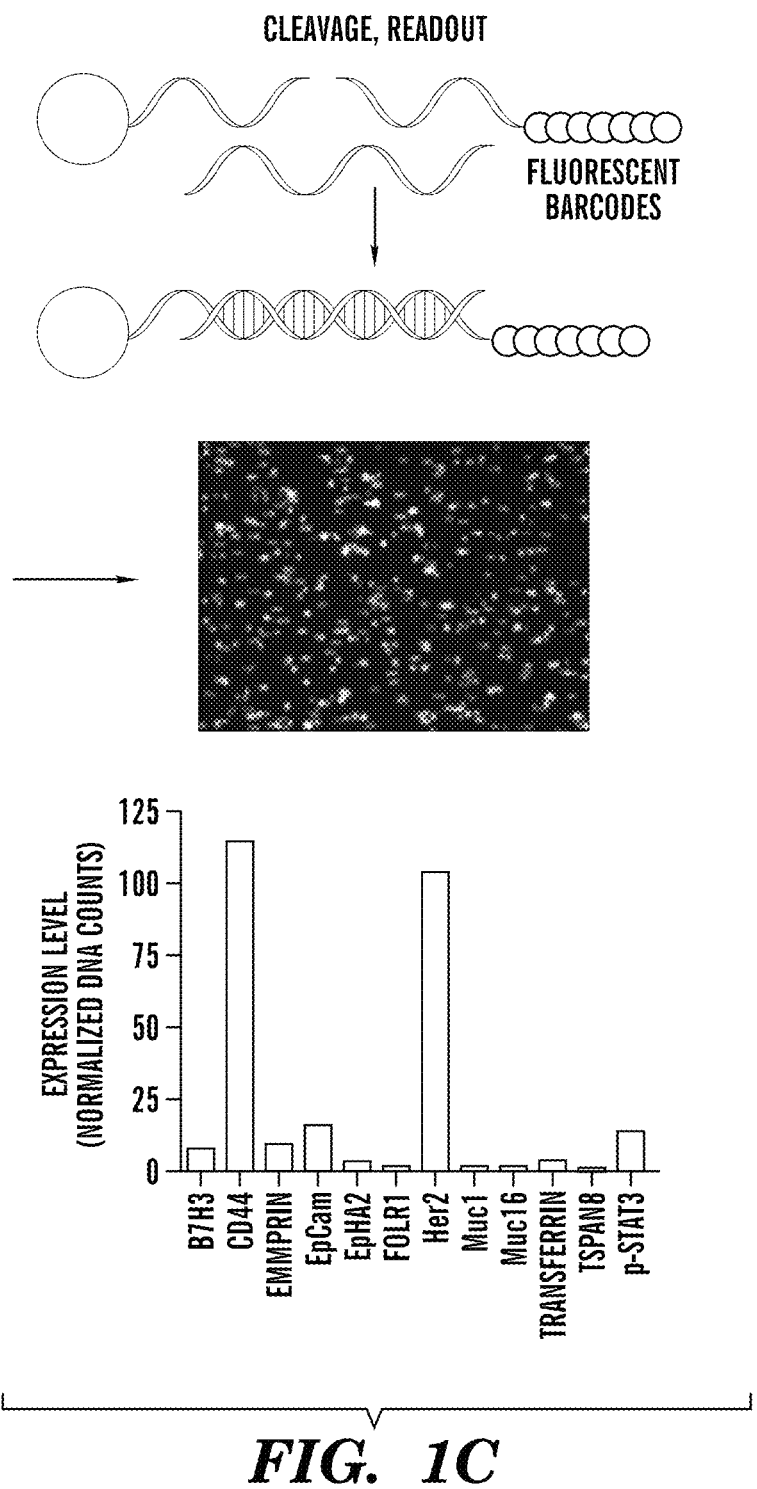
Figures 10A, 10B:
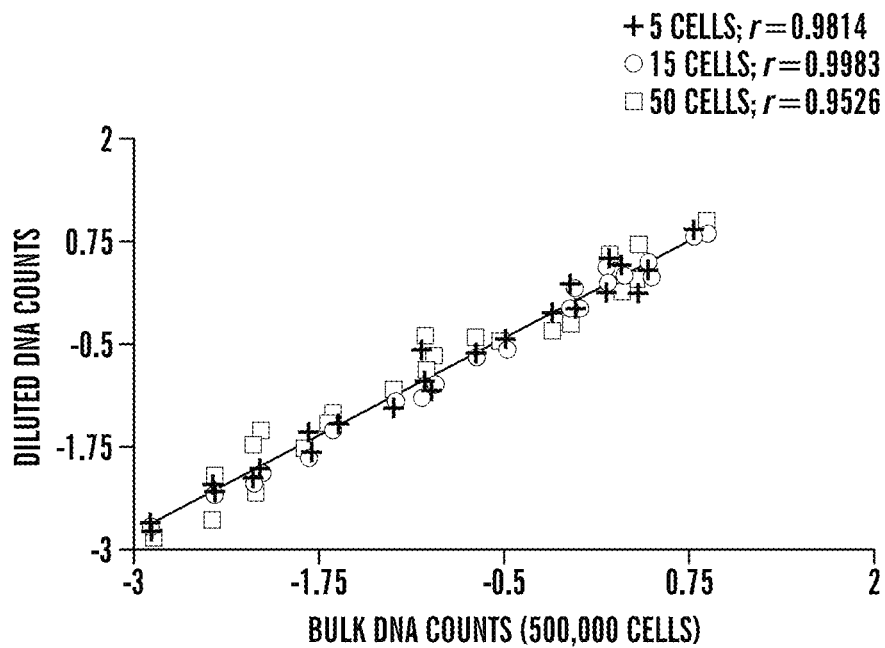
Figure 10C:
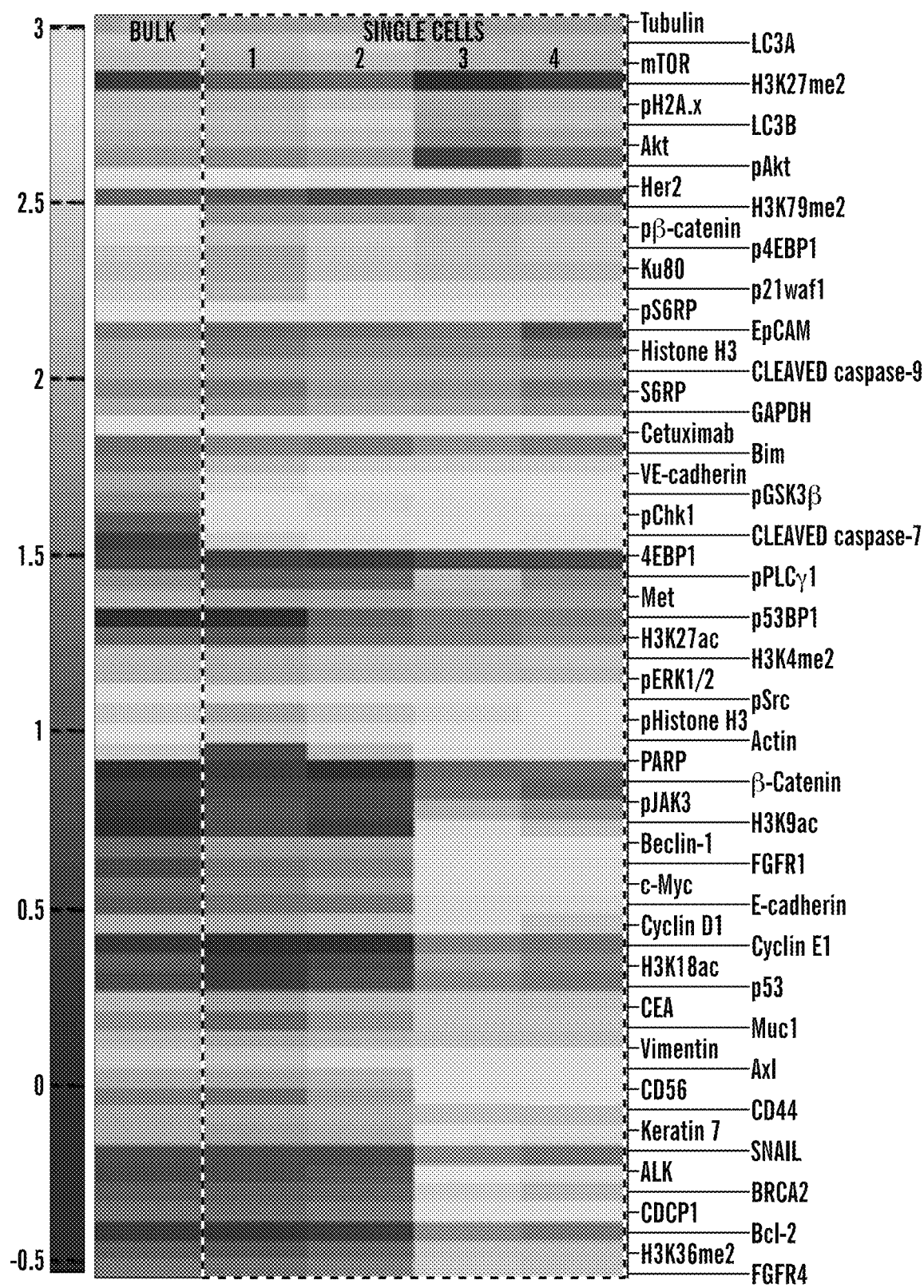

FIGS. 10A-10C are experimental data on detection sensitivity using a human epidermal cancer cell line. (FIG. 10A) A bulk sample of 500,000 cells from the epidermoid carcinoma cell line A431 was lysed and processed as shown in FIGS. 1A-1C. Dilutions corresponding to 5, 15, and 50 cells were then compared to the bulk measurement. (FIG. 10B) Correlation values for single A431 cells selected by micromanipulation are compared to the bulk measurements (500, 000 cells). (FIG. 10C) Protein expression profiles ($\log_2$ expression values) of four single cells compared with the bulk sample. Correlations were highly significant when comparing all single cells to bulk measurements (P<0.0001, paired t test; GraphPad Prism 6.0).

Figure 11A:
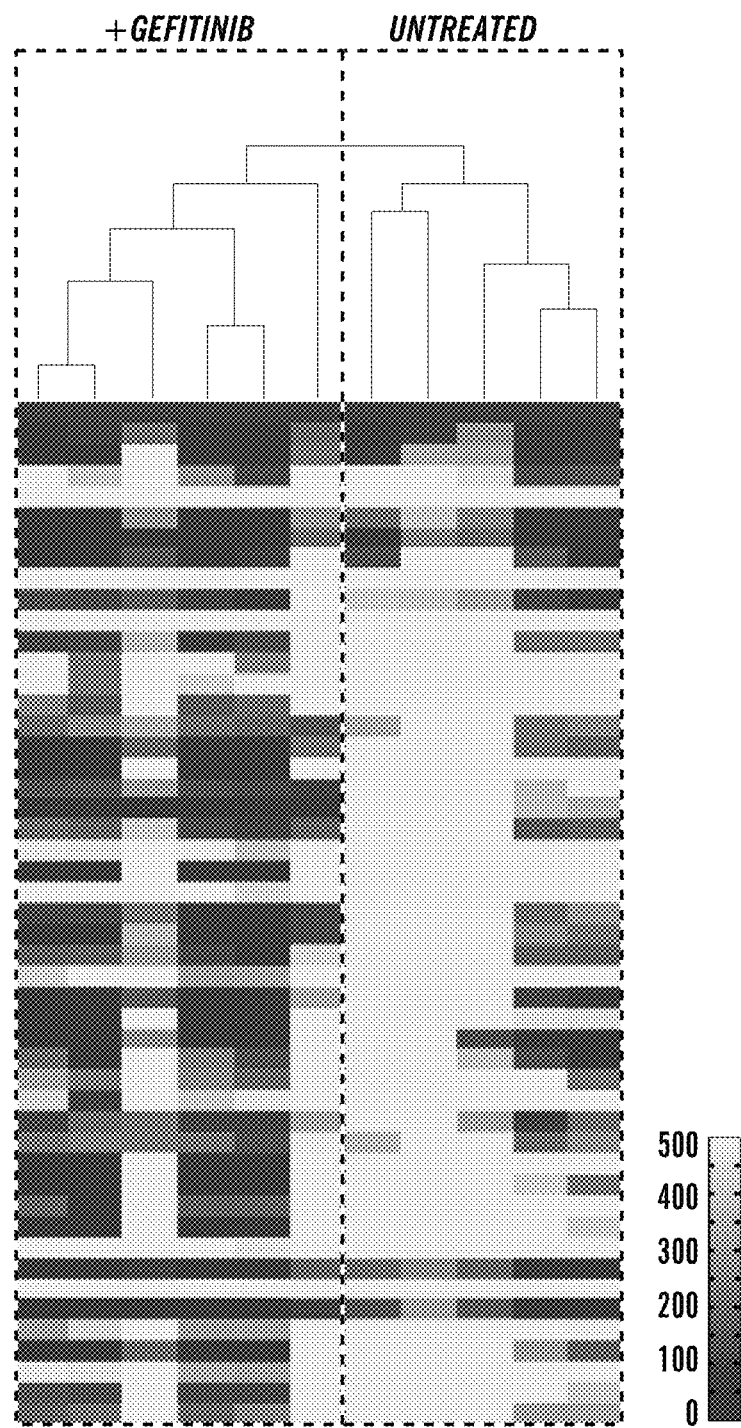
Figure 11B:
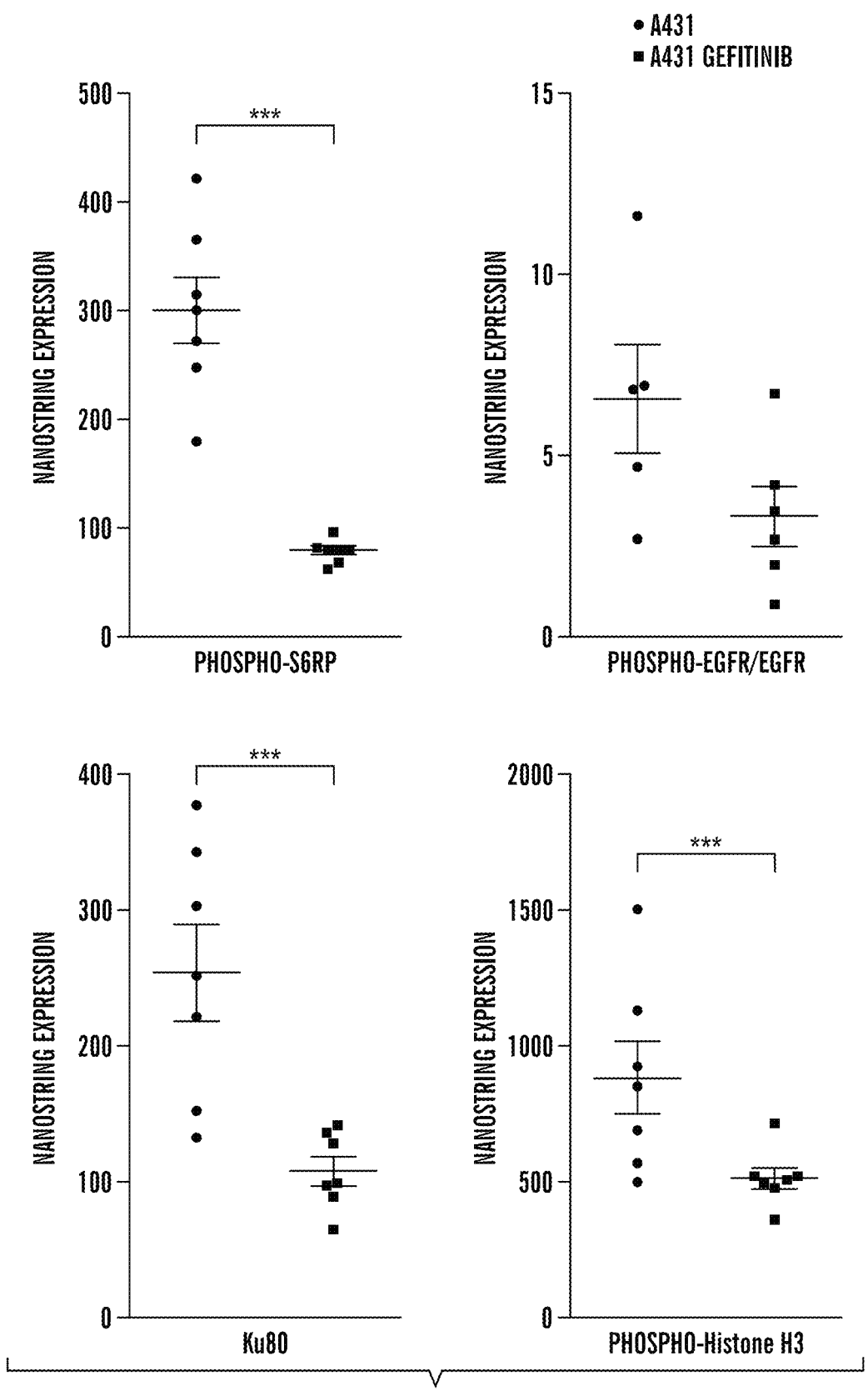

FIGS. 11A-11B are experimental data showing single-cell variability in treated and untreated A431 cells. (FIG. 11A) Single cell measurements in human A431 cell lines that were either treated or untreated with the EGFR inhibitor gefitinib were clustered based on a correlation metric (MatLab). (FIG. 11B) Pairwise t-tests for four markers (FDR=0.1, ***P<0.001, GraphPad Prism), are shown. Markers that were most significant are shown, as well as phosphor-EGFR, which is the primary target of gefitinib inhibition. The distribution between signals from untreated cells (blue) and treated cells (yellow) are shown. Each point represents expression levels calculated from a single cell, and the mean and standard deviation are shown in the box plot.

Figure 12A:
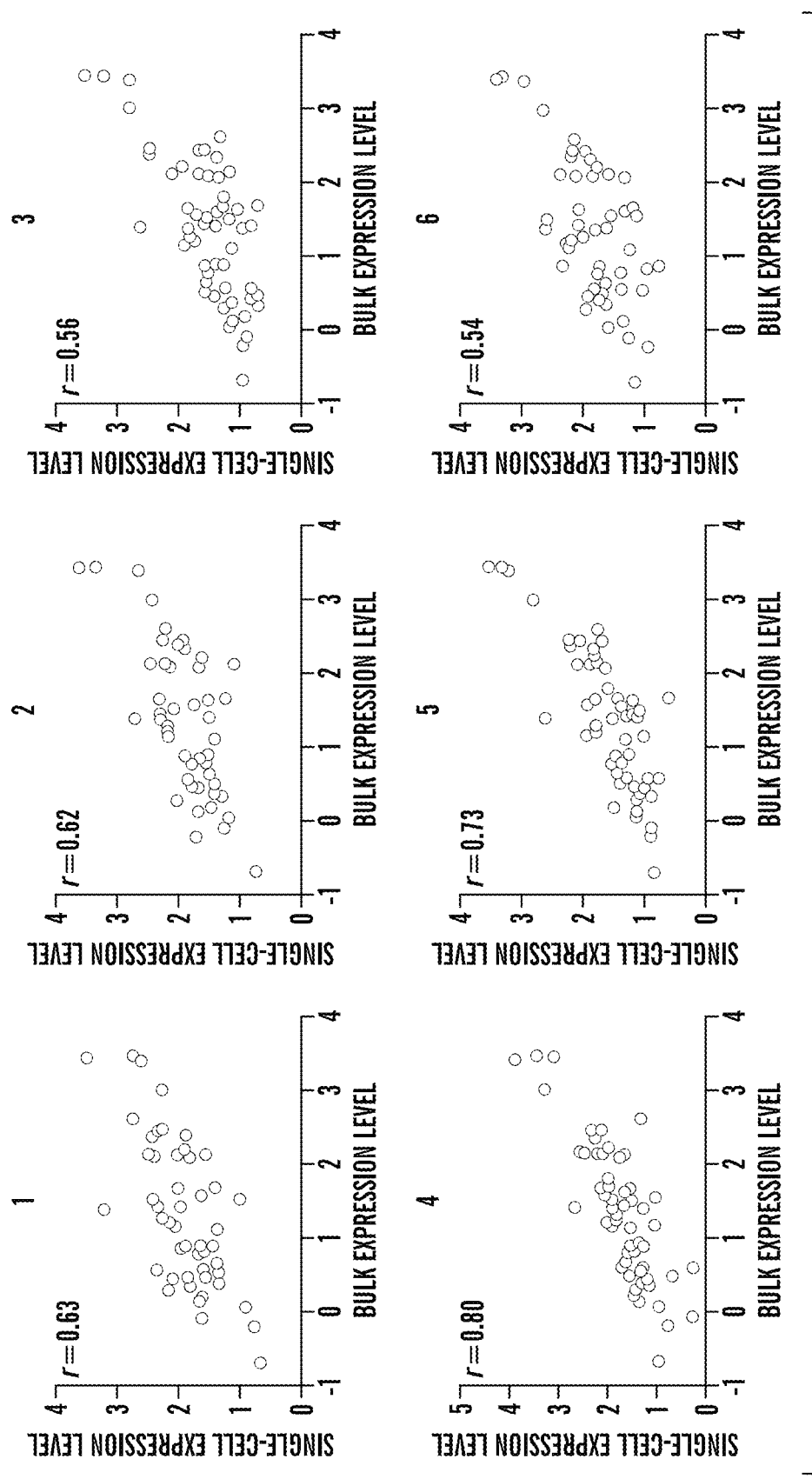
Figure 12A:
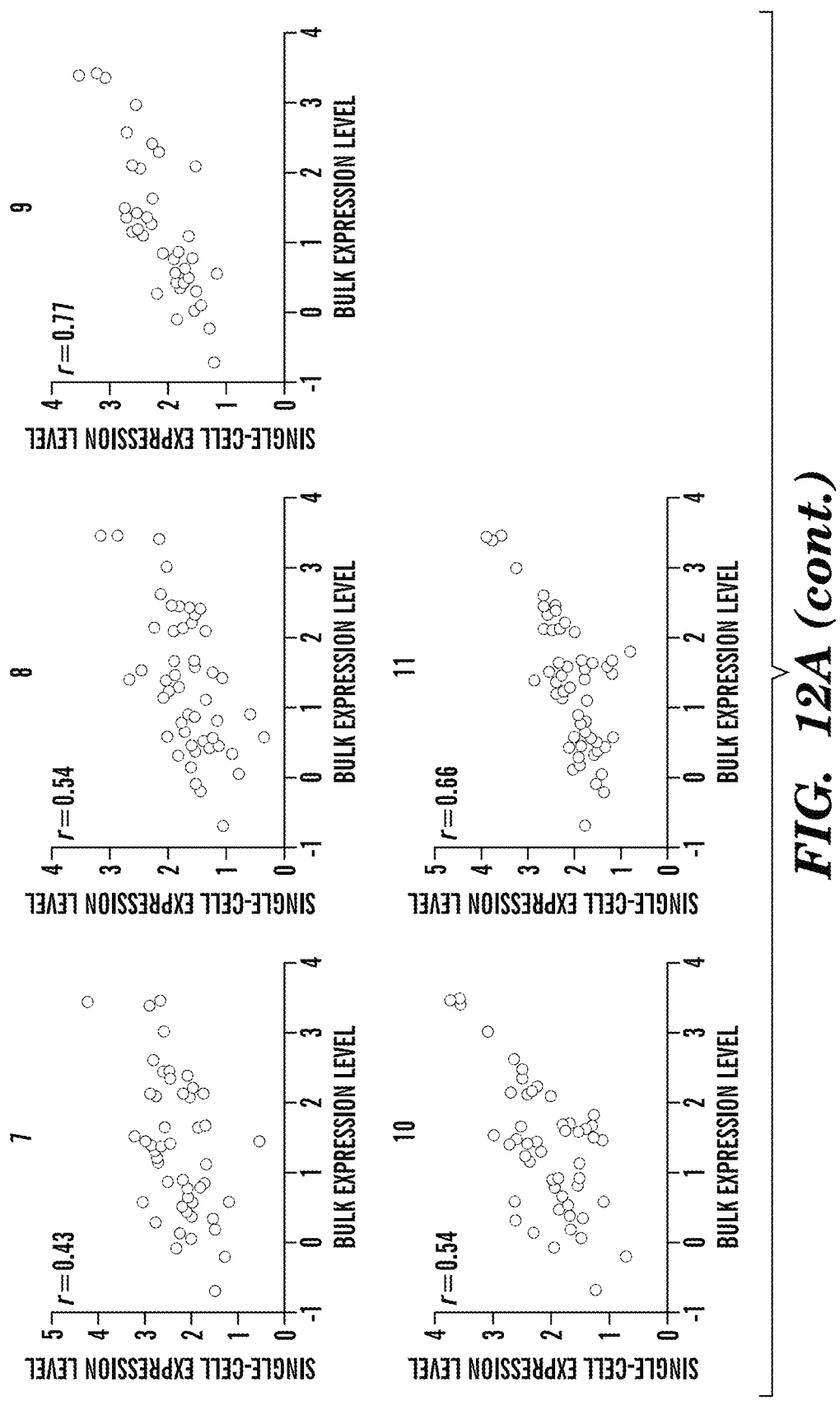
Figure 12B:
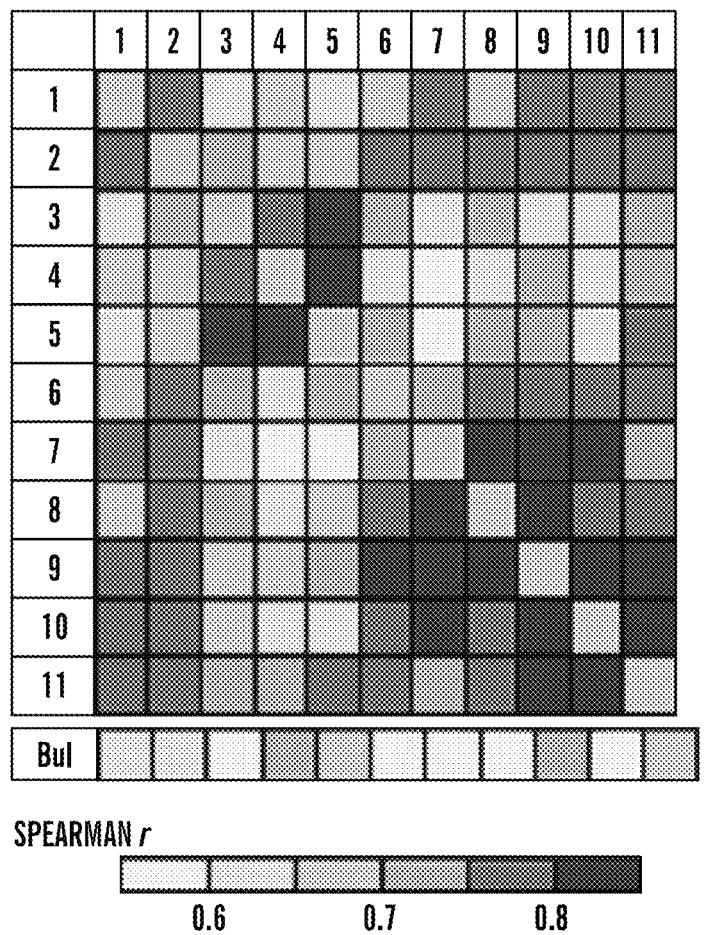

FIGS. 12A-12B show experimental data based on a single-cell protein analysis in a patient sample. An FNA was obtained from a patient with biopsy-proven lung adenocarcinoma. (FIG. 12A) Eleven harvested cells were analyzed individually, and protein expression levels in each cell (y axis) were correlated with expression levels from the bulk tumor sample (x axis). Each data point represents the expression for a given marker (n=85 markers, 3 below detection threshold). (FIG. 12B) Spearman R correlation coefficient values for each of the single cells in (FIG. 12A) relative to each other and to the bulk measurement.

Figure 13:
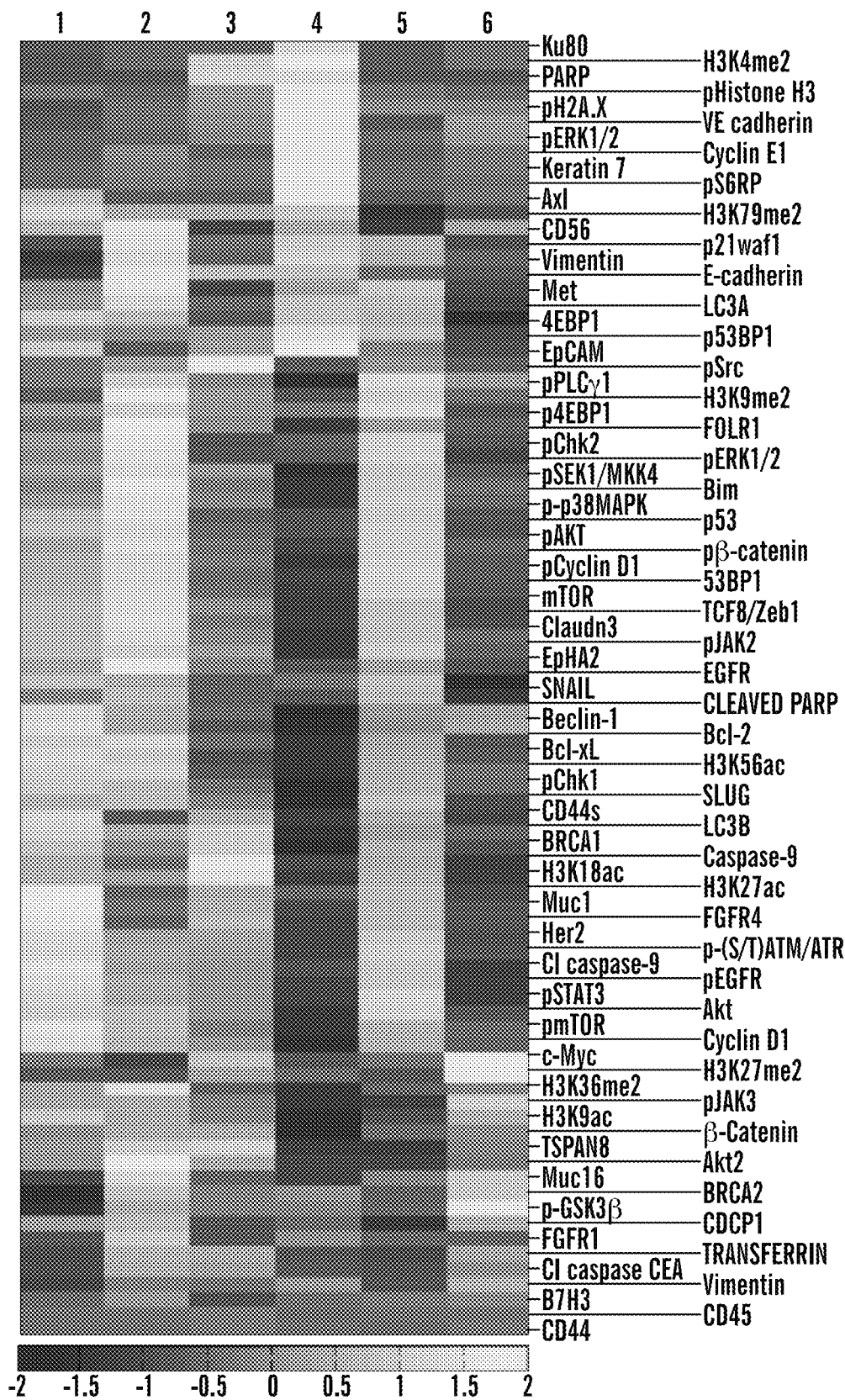

FIG. 13 shows interpatient heterogeneity in lung cancer. FNAs were obtained from six patients with biopsy-proven lung adenocarcinoma, and bulk samples (~100 cells each) were processed as shown in FIGS. 1A-1C with 88 barcoded antibodies. Expression data were log 2-normalized by row to show differences between each patient. Expression profiles were heterogeneous despite the identical histological type: Upon genetic analysis, patients 1 and 2 had EGFR exon 19 amplification and T790M mutations, patient 3 had an exon 20 EGFR mutation, patient 4 had an EGFR L858R mutation and an additional BRAF mutation, patient 5 had a KRAS mutation, and patient 6 had an EML4-ALK translocation.

Figure 14A:
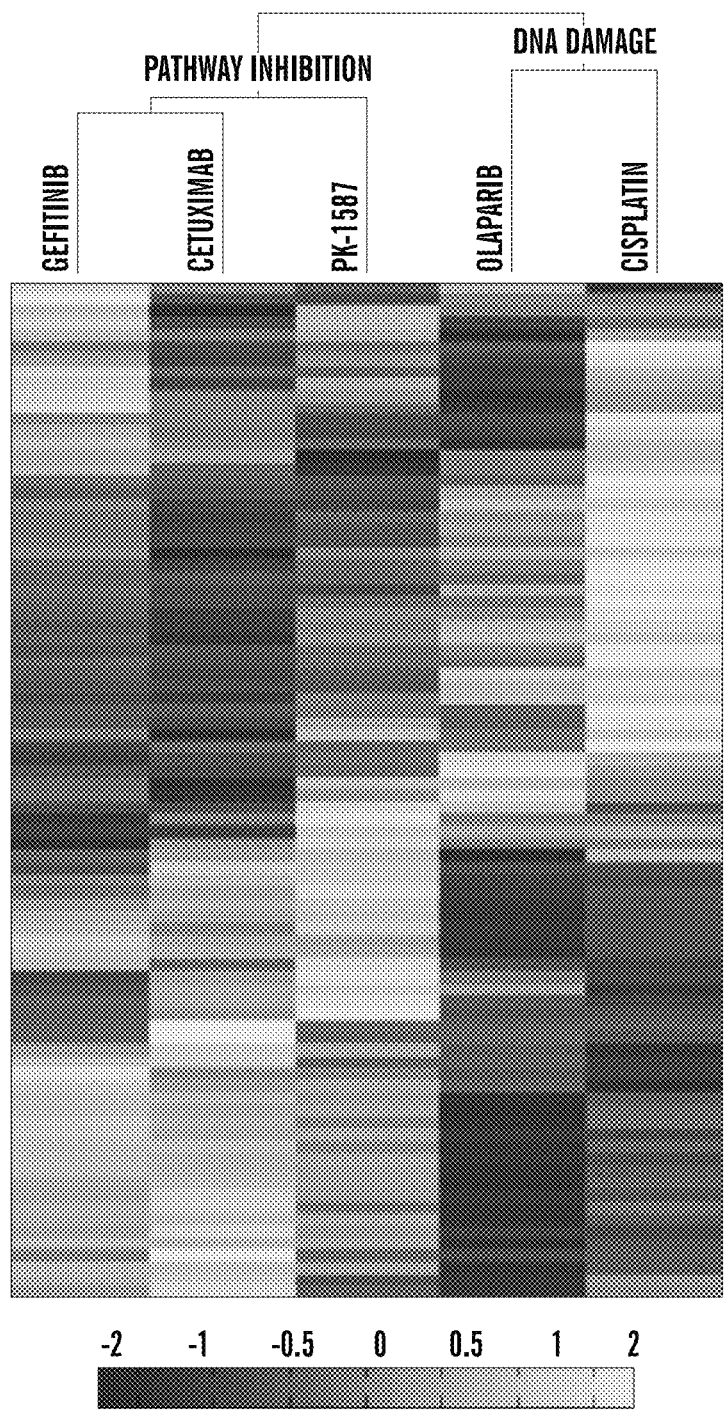
Figure 14B:
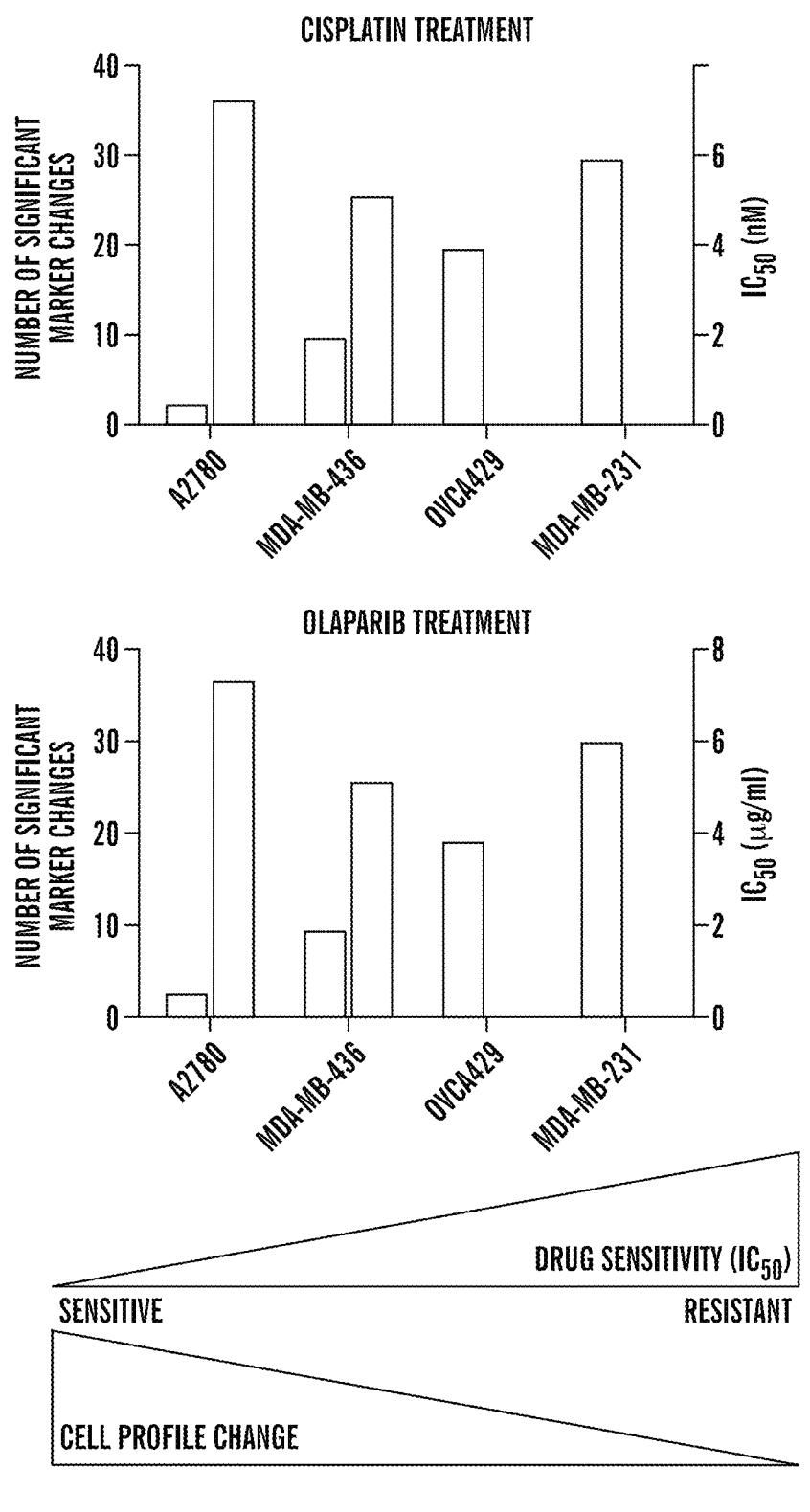
Figure 15A:
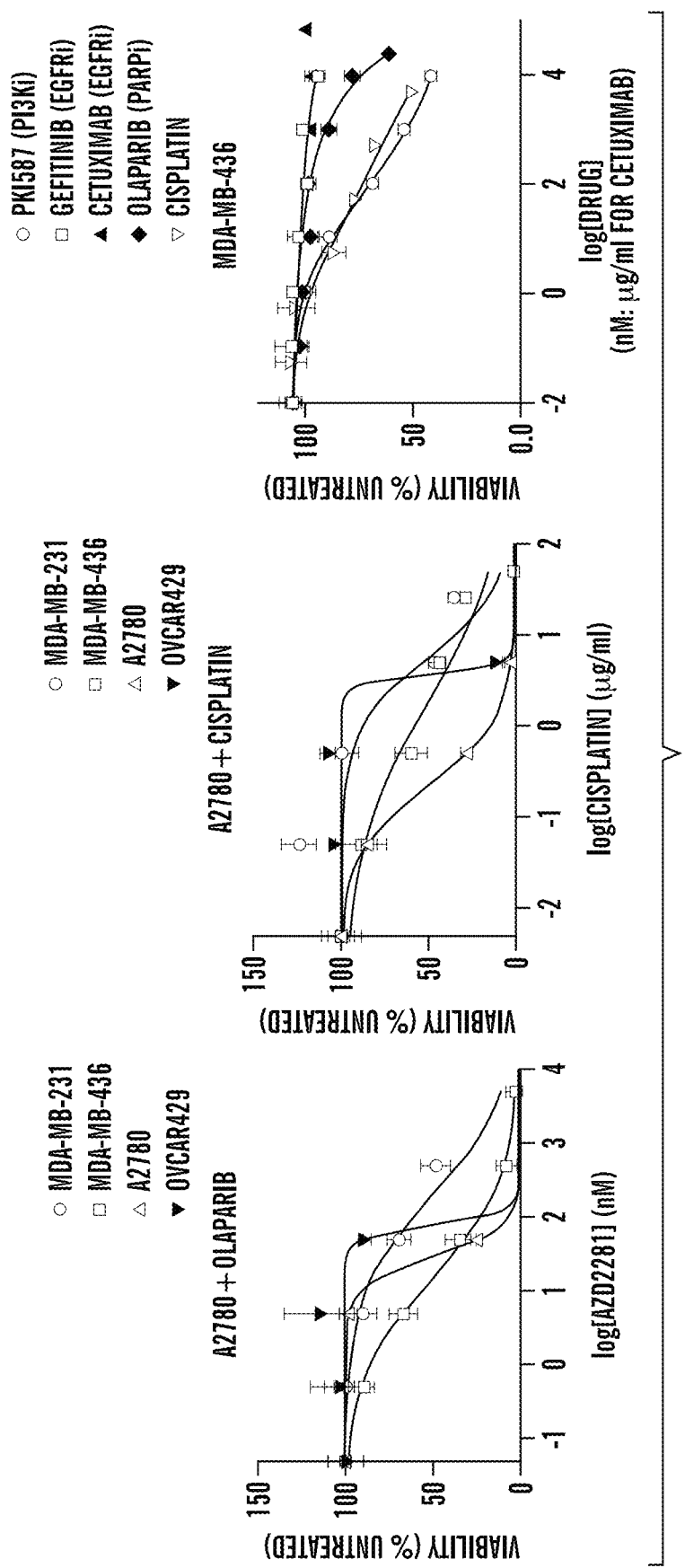

FIGS. 14A-14B show experimental data on effect of different therapies on protein expression profiles in MDA-MB-436 triple-negative breast cancer cell line. (FIG. 14A) MDA-MB-436 cells were treated with different agents, and marker proteins were measured. Unsupervised hierarchical clustering based on Euclidean distance grouped drug treatments by their mechanisms of action (molecularly targeted versus DNA damaging) and primary targets [EGFR for gefitinib/cetuximab and mammalian target of rapamycin (mTOR)/PI3K for PKI-587]. Data show the $\log_2$ fold change of marker expression in treated compared to untreated cells for n=84 markers. All experiments were performed in triplicate. (FIG. 14B) Correlating drug sensitivity of four different cell lines with proteomic profile changes after treatment with cisplatin and olaparib. IC50 values (black bars) were calculated on the basis of viability curves (FIG. 15A). The cell profile change after treatment is represented by the number of significant markers (gray bars) that were identified by a pairwise t test of treated versus untreated samples (FDR=0.1).

FIGS. 15A-15E are graphs showing protein marker changes correlate with drug sensitivity. Human ovarian carcinoma (A2780, OVCAR429) and breast cancer (MDA-MB-436, MDA-MB-231) cell lines react differently to chemotherapy. Those with increased sensitivity to a drug are expected to show a greater degree of change in their cell profiles. (FIG. 15A) Sensitivity was determined by IC50 values calculated from MTS viability curves in biological triplicate for each cell line as shown. Exact values and the fit of the viability curves were determined by GraphPad Prism 5.0 (dose-response curve). (FIG. 15B) Data of a control study where cell lines were treated with cetuximab, which resulted in drug inhibition. (FIGS. 15C-15E) Changes across a selected panel of several DNA damage markers (pH2A.X, Ku80, pChk2, pChhk1), apoptosis markers (cleaved PARP, cleaved caspase 7), and other mechanisms commonly associated with platinum treatment (pERK, Bim). Data are means±SEM, performed in triplicate.

FIGS. 16A-16D show that taxol treatment and dose response screens in human HT1080 cells in vitro. (FIG. 16A) Select marker changes from dose response taxol treatment are displayed with DNA barcoding profiles with standard error from biological duplicate. (FIG. 16B) EC50 values from the dose response curves are displayed along with $R^2$ values. (FIG. 16C) Markers that significantly differed from untreated (pairwise multiple t-test, FDR=0.2) were shown to have a dose-dependent response to taxol treatment. (FIG. 16D) The markers that significantly different between untreated and treated conditions are shown in a venn diagram. CDCP1 was significantly different at all doses.

Figure 17A:
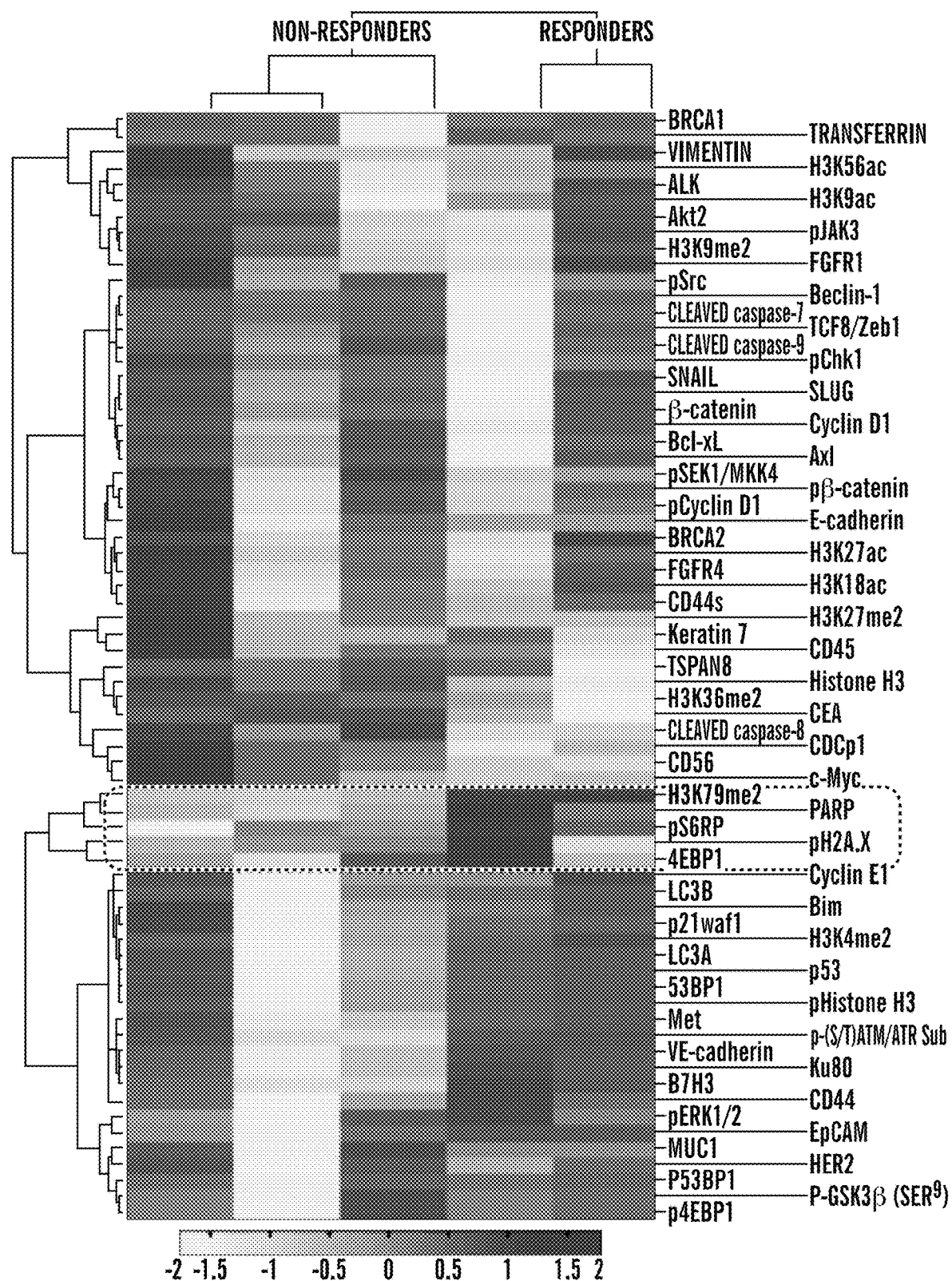
Figure 17B:
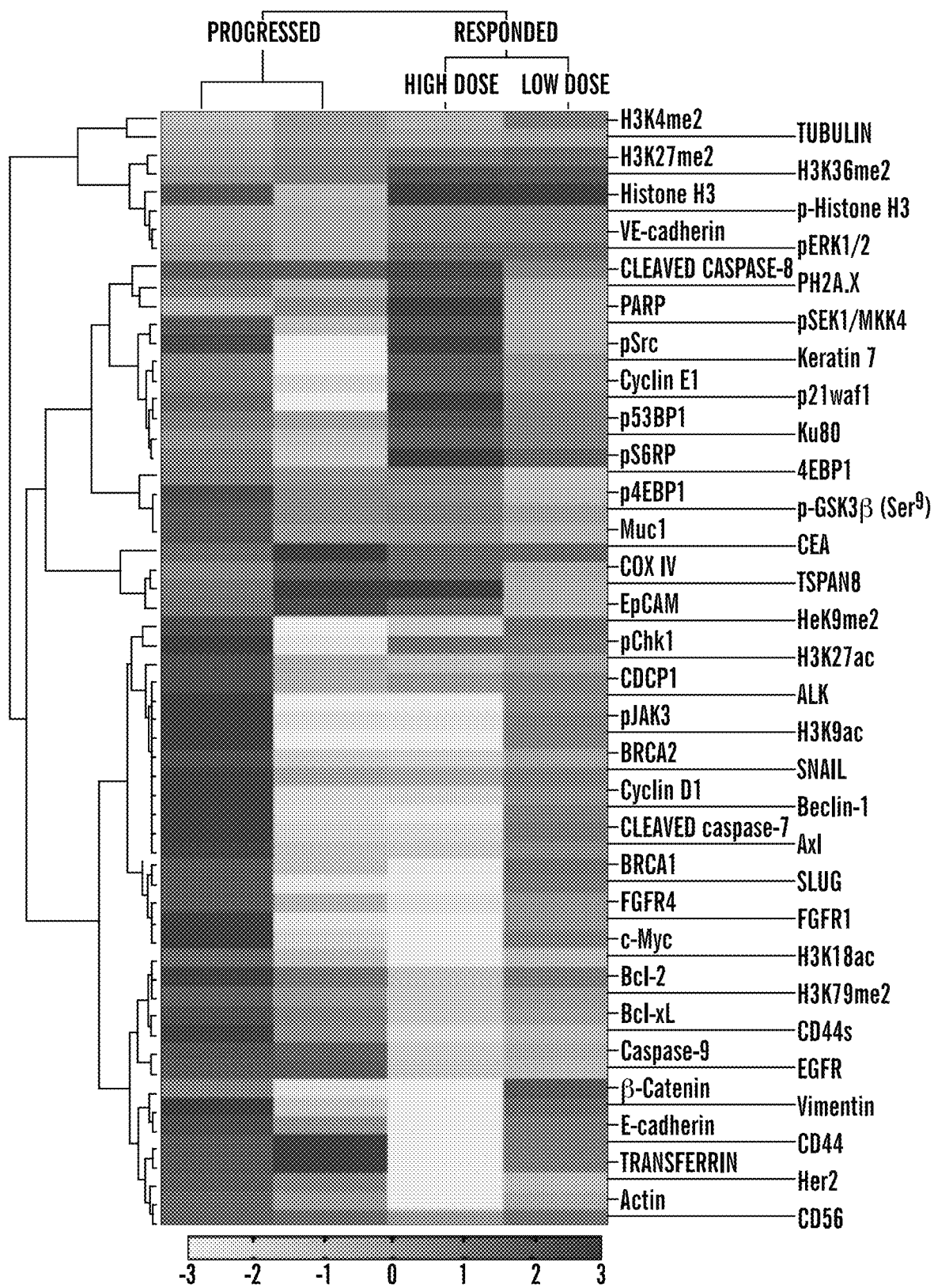

FIGS. 17A-17B show expression profilings of various cancer patients for monitoring and predicting treatment response in patients receiving PI3K inhibitors. (FIG. 17A) Profiles of five drug-naïve cancer patients are shown with clustering based on correlation metrics with weighted linkage. The dotted box shows the cluster including the marker that best separated responders and nonresponders (H3K79me2). Other markers in the cluster include pS6RP (a downstream target of PI3K), pH2A.X (DNA damage marker), PARP (DNA repair protein), and 4EBP1 (protein translation). (FIG. 17B) Four patients with biopsy-proven adenocarcinoma were treated with PI3Ki, and primary cancers were biopsied before and after treatment. The heat map is a pre-post treatment difference map showing log 2 fold changes in protein expression (normalized by row to highlight differences between patients). Patient segregation is by correlation distance metric (weighted linkage). The patient in the third column received a higher dose of the PI3Ki (400 mg, twice daily) than the patient in the fourth column (150 mg, twice daily).

Figure 18A:
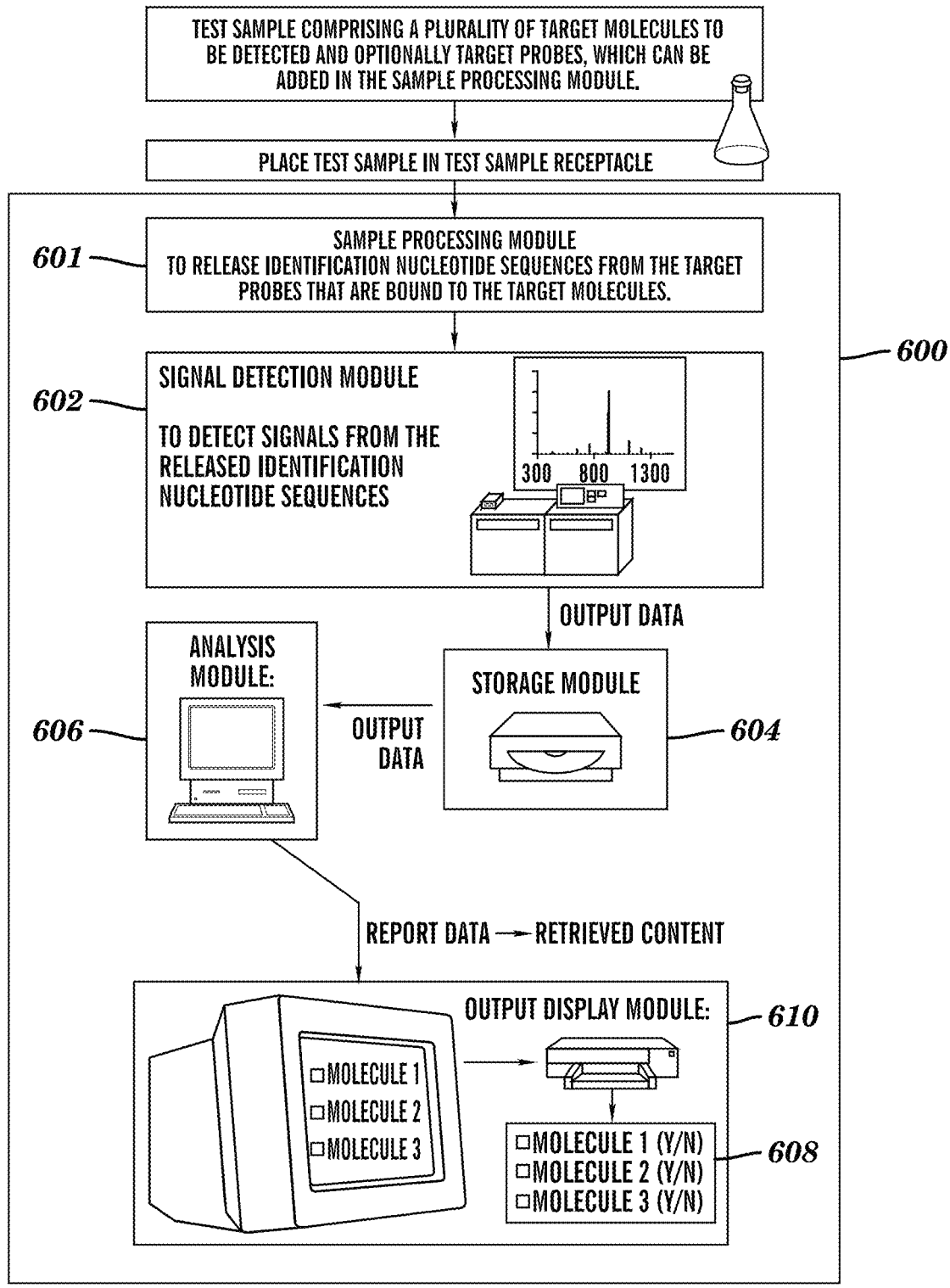
Figure 18B:
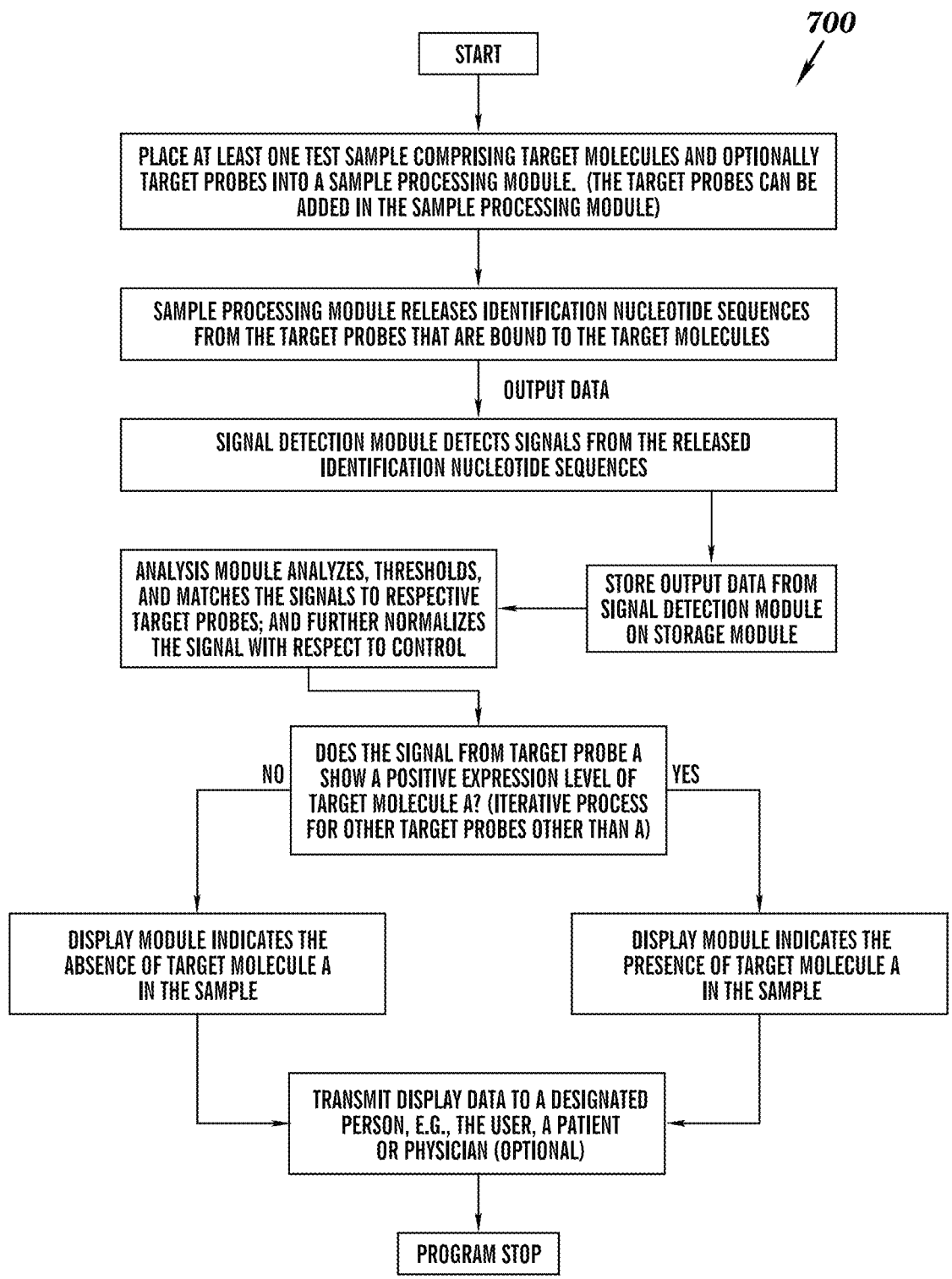

FIGS. 18A-18B are block diagrams showing exemplary systems for use in the methods described herein, e.g., for multiplexed detection of target molecules in a sample.

DETAILED DESCRIPTION

Immunohistochemistry-based clinical diagnoses generally require invasive core biopsies and use a limited number of protein stains to identify and classify cancers. Fine-needle aspirates (FNAs) employ thin needles to obtain cells from tumor masses and the procedure is thus minimally invasive. While FNAs can give tremendous insight into malignancy, the number of cells in the FNAs is so small (compared to core biopsy) that current technologies for protein analysis, such as immunohistochemistry, are insufficient. Embodiments of various aspects described herein are, in part, based on the development of a scalable method that not only allows analysis of a plurality of proteins from a limited amount of sample, e.g., FNAs, but also preserves genetic material from the same sample to enable simultaneous measurements of proteins and genetic materials (e.g., DNA, RNA, epigenetic and microRNAs). In one embodiment, the method relies on DNA-barcoded antibody sensing, where barcodes-single strands of DNA- can be photocleaved and detected using fluorescent complementary probes without any amplification steps, and is referred to as an antibody barcoding with photocleavable DNA (ABCD) platform herein. Unlike the protein detection method described in U.S. Pat. App. Pub. No. US 2011/0086774, the DNA barcode and the antibody that the inventors developed is coupled together through a cleavable, non-hybridizable linker, not a hybridizable linker that is reversibly hybridized (e.g., by basepairing) to a portion of the DNA barcode. In addition, detection of a target protein is based on binding of a single DNA-barcoded antibody to the target protein, which is different from the protein detection method described in U.S. Pat. App. Pub. No. US 2011/0086774, where two antibodies (one for immobilization to a solid substrate, e.g., a bead, and another for detection purpose) are required for binding to different regions of the target protein.

To demonstrate the capability of the ABCD platform, inventors isolated cancer cells within the FNAs of patients and exposed these cells to a mixture of about 90 DNA-barcoded antibodies, covering the hallmark processes in cancer (for example, apoptosis and DNA damage). The inventors discovered that the single-cell protein analysis of the patients' FNAs showed high intratumor heterogeneity, indicating the ability of the ABCD platform to perform protein profiling on rare single cells, including, but not limited to circulating tumor cells. Further, the inventors discovered that patients who showed identical histopathology yet showed patient heterogeneity in proteomic profiling, indicating the ability of the ABCD platform to identify personalized targets for treatment. By profiling and clustering protein expression in patients' samples, the inventors also showed use of the ABCD platform to monitor and predict treatment response in patients receiving chemotherapy, e.g., kinase inhibitors. The ABCD platform for generating a protein profiling is scalable and can be extended to detect other target molecules, e.g., metabolites and lipids. Not only can the ABCD platform measure protein quantitatively, but the ABCD platform can also enable simultaneous measurements of at least 90 different proteins or more (e.g., about 100-200 different proteins) in a single sample. Further, because of the high sensitivity of the ABCD platform, the ABCD platform can enable detection of rare proteins, e.g., proteins that are not generally highly-expressed, or not easily accessible or extracted, such as intracellular proteins. Accordingly, various aspects described herein provide for methods, systems and kits for detecting and/or quantifying a plurality of target molecules from a sample, as well as their uses thereof in various applications, e.g., diagnosis, prognosis, personalized treatment, and/or treatment monitoring.

Methods for Detecting or Quantifying a Plurality of Target Molecules in a Sample In one aspect, provided herein is a method for detecting a plurality of target molecules in a sample. The method comprises (a) contacting a sample with a composition comprising a plurality of target probes, wherein each target probe in the plurality comprises: (i) a target-binding molecule that specifically binds to a target molecule or a distinct target molecule in the sample; (ii) an identification nucleotide sequence that identifies the target-binding molecule; and (iii) a cleavable linker between the target-binding molecule and the identification nucleotide sequence; (b) releasing the identification nucleotide sequences from the bound target probes; and (c) detecting signals from the released identification nucleotide sequences, wherein the signals are distinguishable for the identification nucleotide sequences, thereby identifying the corresponding target-binding molecules and detecting a plurality of target molecules in the sample.

In some embodiments where each target probe in the plurality binds to a distinct target molecule, no two target probes in the plurality binds to different regions of the same target molecule.

Stated another way, the method comprises: (a) forming a plurality of complexes in a sample, each complex comprising a target molecule and a target probe bound thereto, wherein the target probe comprises (i) a target-binding molecule that specifically binds to the target molecule present in the sample; (ii) an identification nucleotide sequence that identifies the target-binding molecule; and (iii) a cleavable linker between the target-binding molecule and the identification nucleotide sequence; (b) releasing the identification nucleotide sequences from the complex; and (c) detecting signals from the released identification nucleotide sequences, wherein the signals are distinguishable for the identification nucleotide sequences, thereby identifying the corresponding target-binding molecules and detecting a plurality of target molecules in the sample. In some embodiments, the cleavable linker is not pre-hybridized (e.g., by basepairing) to any portion of the identified nucleotide sequences.

In some embodiments, e.g., cell assay, each complex comprising a target molecule and a target probe bound thereto does not require two or more target probes of different kinds bound to the same target molecule, where each of the target probes binds to a different region of the same target molecule. For example, unlike the protein detection method described in the U.S. Pat. App. No. US 2011/0086774, each complex described herein does not require both a first target probe binding to a first region of a target molecule, and a second target probe binding to a second region of the same target molecule. Stated another way, in some embodiments, a single target probe as described herein binding to a target molecule is sufficient for enablement of the methods described herein. In these embodiments, the method described herein does not require another target probe binding to the same target molecule for attachment to a solid substrate (e.g., a bead), e.g., as described in the U.S. Pat. App. No. US 2011/0086774.

In various embodiments of different aspects described herein, the cleavable linker does not comprise a polynucleotide sequence (e.g., a single-stranded polynucleotide sequence) that is complementary (for basepairing) to at least a portion of the identification nucleotide sequence. That is, in these embodiments, the identification nucleotide sequence is not released from the complex by detaching from the complementary polynucleotide sequence coupled to a target-binding molecule. Accordingly, in some embodiments, a target probe comprises (i) a target-binding molecule that specifically binds to the target molecule present in the sample; (ii) an identification nucleotide sequence that identifies the target-binding molecule; and (iii) a cleavable, non-hybridizable linker between the target-binding molecule and the identification nucleotide sequence.

"Target probes" is described in detail in the following "Target Probes" section.

In some embodiments, the method can further comprise separating unbound target probes from target probes that are bound to the target molecules in the sample.

As used herein, the term "bound target probes" refers to target probes binding to target molecules in a sample.

In some embodiments, the method can further comprise, prior to contacting the sample with target probes, separating target cells from interfering cells in the sample. Methods to separate target cells from interfering cells are known in the sample, e.g., based on cell surface proteins that distinguish target cells from interfering cells. By way of example only, target cells or interfering cells can be labeled with ligands that target specific cells of interests (e.g., cell-specific antibodies). In some embodiments where the cell-specific ligands are fluorescently labeled, the labeled cells can then be sorted, e.g., by flow cytometry. Alternatively, if the cell-specific ligands are attached to magnetic particles, the labeled cells with bound magnetic particles can be isolated from the sample by magnetic separation. In some embodiments, the cell sorting or selection can be performed in a microfluidic device. In some embodiments, methods for isolating target cells or interfering cells from a sample as described in the International Pat. App. No. WO 2013/078332, the content of which are incorporated herein by reference, can be used in combination with the methods described herein.

Target cells can be prokaryotic or eukaryotic (including microbes such as bacteria, fungi, virus and/or pathogens). In some embodiments, the target cells can comprise normal cells, diseased cells, mutant cells, germ cells, somatic cells, and/or rare cells. Example of rare cells include, without limitations, circulating tumor cells, fetal cells, stem cells, immune cells, clonal cells, and any combination thereof. In some embodiments, the target cells can comprise tumor cells. In some embodiments, the tumor cells can be derived from a tissue biopsy, a fine aspirate or a liquid biopsy (e.g., peritoneal, pleural, cerebrospinal fluid, and/or blood), a mucosal swap, a skin biopsy, a stool sample, or any combinations thereof. In some embodiments, whole cells and/or cell lysates can be analyzed by the methods described herein to detect a plurality of target molecules in a sample. In some embodiments, the whole cells can be obtained from a fixed cell or tissue sample.

Exemplary target molecules which can be detected by the methods described herein include, but are not limited to proteins, peptides, metabolites, lipids, carbohydrates, toxins, growth factors, hormones, cytokines, cells, and any combinations thereof. In some embodiments, the target molecules to be detected can be extracellular or secreted molecules. In some embodiments, the target molecules to be detected can be intracellular, e.g., cytoplasmic molecules or nuclear molecules.

To detect intracellular molecules (e.g., intracellular proteins), the target cells in the sample can be permeabilized or lysed (e.g., with a lysis buffer or a surfactant) such that target probes can contact the target intracellular molecules for further processing and analysis. In some embodiments, the lysis buffer can comprise a protease. An exemplary protease is a protease K.

The identification nucleotide sequences can be released from the bound target probes using any methods known in the art, depending on the types of the cleavable linkers. In some embodiments, the cleavable linker does not comprise a polynucleotide sequence (e.g., a single-stranded polynucleotide sequence) that is complementary (for basepairing) to at least a portion of the identification nucleotide sequence. That is, in these embodiments, the identification nucleotide sequence is not released from the complex by detaching from the complementary polynucleotide sequence (hybridizable linker) coupled to a target-binding molecule. Cleavable, non-hybridizable linkers are known in the art, of which examples include, but are not limited to the ones that are sensitive to an enzyme, pH, temperature, light, shear stress, sonication, a chemical agent (e.g., dithiothreitol), or any combination thereof. In some embodiments, the cleavable linker can be sensitive to light and enzyme degradation.

In some embodiments where a photocleavable linker is used, the identification nucleotide sequences can be released from the bound target probes by exposing the bound target probes to a light of a specified wavelength. In some embodiments, ultraviolet light can be used to release identification nucleotide sequences from bound target probes.

The signals from the released identification nucleotide sequences can be detected by various methods known in the art, including, but not limited to sequencing, quantitative polymerase chain reaction (PCR), multiplexed (PCR), mass cytometry, fluorophore-inactivated multiplexed immunofluorescence, hybridization-based methods, fluorescence hybridization-based methods, imaging, and any combinations thereof. In some embodiments, the signals from the released identification nucleotide sequences can be determined by electrophoresis-based methods. In some embodiments, the signals from the released identification nucleotide sequences are not determined by electrophoresis-based methods. Gel electrophoresis-based methods are generally not as quantitative or sensitive as other detection methods described herein such as PCR, fluorescence hybridization-based methods, and nanoString nCounter® hybridization technology, for example, as described in U.S. Pat. No. 8,415,102, and Geiss et al. Nature Biotechnology. 2008. 26(3): 317-325, the contents of each of which is incorporated herein by reference. Thus, gel electrophoresis-based methods do not necessarily have required sensitivity for detection of rare proteins, e.g., proteins that are not generally highly-expressed, or not easily accessible or extracted, such as intracellular proteins. In addition, limited size resolution on gels can limit simultaneous measurements of a large number (e.g., more than 5 or more than 10) of different target molecules, as compared to other detection methods described herein such as PCR, fluorescence hybridization-based methods, and nanoString nCounter® hybridization technology, for example, as described in U.S. Pat. No. 8,415,102, and Geiss et al. Nature Biotechnology. 2008. 26(3): 317-325, the contents of each of which is incorporated herein by reference.

The nature of the signals from the released identification nucleotide sequences can vary with choice of detection methods and/or detectable labels. In some embodiments, the signals from the released identification nucleotide sequences can be detected by hybridization-based methods. For example, in some embodiments, the method can further comprise, prior to detecting the signals from the released identification nucleotide sequences, coupling the released identification nucleotide sequences to a detection composition comprising a plurality of reporter probes. Each reporter probe in the plurality can comprise (i) a first target probe-specific region that is capable of binding a first portion of the identification nucleotide sequence; and (ii) a detectable label that identifies the reporter probe. In these embodiments, signals from the respective detectable labels of the reporter probes that are coupled to the released identification nucleotide sequences can be detected accordingly. Since the signals are distinguishable for each respective reporter probes that are bound to the identification nucleotide sequences, target-binding molecules can be correspondingly identified, thereby detecting a plurality of target molecules in the sample. Additional information of "reporter probes" will be found in the following "Reporter Probes" section.

In some embodiments, the detection composition used in the methods described herein can additionally comprise a plurality of capture probes as described herein. Additional information of capture probes will be found in the "Capture Probes" section below.

In some embodiments, the method selected to detect signals from the released identification nucleotide sequences does not require amplification of the released identification nucleotide sequences, first target probe-specific region, or the second target probe-specific region. Amplification-free detection methods can minimize any bias or errors introduced during amplification, e.g., due to varying amplification efficiencies among the nucleotide sequences.

In some embodiments, the identification nucleotide sequences can be detected by nanoString nCounter® hybridization technology, for example, as described in U.S. Pat. No. 8,415,102, and Geiss et al. Nature Biotechnology. 2008. 26(3): 317-325, the contents of each of which is incorporated herein by reference.

Typically, signals detected from the identification nucleotide sequences of the target probes corresponding to target molecules can be compared to a control reference to account for any non-specific binding. Accordingly, in some embodiments, the composition added to the sample can further comprise a plurality of control probes. Each control probe in the plurality can comprise: (i) a control-binding molecule that specifically binds to one control molecule in the sample; (ii) an identification control sequence that identifies the control-binding molecule; and (iii) a cleavable linker between the control-binding molecule and the identification control sequence. The control-binding molecule can bind to a control protein present in a sample. Non-limiting examples of control proteins include housekeeping proteins, control IgG isotypes, mutant non-functional or non-binding proteins, and any combinations thereof.

Signals from the control probes can then be used to threshold the signals from the target probes. Accordingly, in some embodiments, the method can further comprise thresholding the target signals. In some embodiments, the target signals can be thresholded on the basis of nonspecific binding. For example, in some embodiments, the threshold can be determined by using standard deviation and measurement error from at least one or more control proteins. The threshold is generally set to be greater than that of the signals from the non-specific binding. In some embodiments, the threshold can be at least 50% or more (including, e.g., at least 60%, at least 70%, at least 80%, at least 90%, at least 95%, or higher) greater than that of the signals from the non-specific binding. In some embodiments, the threshold can be at least 1.1-fold or more (including, e.g., at least 1.2-fold, at least 1.3-fold, at least 1.4-fold, at least 1.5-fold, at least 2-fold, or higher) greater than that of the signals from the non-specific binding.

In some embodiments, the method can further comprise quantifying the signals (e.g., signals that are above the pre-determined threshold) by normalizing the signals associated with the target probes by the signals associated with the control probes. In some embodiments, the signals can be analyzed and expressed as number of identification nucleotide sequences per target-binding molecule (or target molecule).

In some embodiments, the methods described herein can complement other art-recognized single-cell proteomic techniques. Exemplary single-cell proteomic techniques include, e.g., mass cytometry and fluorophore-inactivated multiplexed immunofluorescence. See, e.g., Bendall et al. Science 332, 687-696 (2011) and Gerdes et al. Proc. Natl. Acad. Sci. U.S.A. 110, 11982-11987 (2013) for additional information about single-cell mass cytometry and fluorophore-inactivated multiplexed immunofluorescence.

In some embodiments, the methods, systems and kits described herein can enable measurements of at least two target molecules of different types. For example, the methods, systems, and kits described herein can be used to measure, for example, nucleic acid molecules and proteins, or proteins and metabolites, or proteins and lipids. The measurements of at least two target molecules of different types can be performed simultaneously or sequentially.

By way of example only, the methods, systems and kits described herein applied to a sample can preserve genetic materials in a sample while detecting other non-genetic target materials in the same sample. This is one of the advantages over existing non-genetic (e.g., proteomic) analysis methods such as flow cytometry and mass cytometry, which generally require an entire cell to measure non-genetic target molecules (e.g., but not limited to proteins). Accordingly, following the non-genetic (e.g., proteomic) measurements, the entire cell including its genetic material is lost. In flow cytometry, the cell is lost as it goes through the flow chamber to detect fluorescence; in mass cytometry, the cellular sample is vaporized, destroying any genetic material that may be available. Cell vaporization in mass cytometry results in destruction of ~60% of the sample even for proteomic detection let alone recovery genetic material.

In contrast, the methods and/or systems presented herein employ an identification nucleotide sequence (which comprises nucleotides) as a tag or barcode to label and/or measure non-genetic target molecules (e.g., but not limited to proteins). Thus, the methods and/or systems described herein ensure that any nucleotide-containing materials (e.g., identification nucleotide sequences and even genetic material extracted from cells) will not be destroyed. As such, in one embodiment, the methods to perform simultaneous measurements on the identification nucleotide sequences (barcodes for identification of non-genetic target molecules, e.g., but not limited to proteins) as well as cells' genetic material of interest (including, but not limited to DNA, RNA, microRNAs, long non-coding RNAs, etc.) are essentially the same, except that the complementary probe set (comprising reporter probes and optionally capture probes) has to be expanded to detect not only the identification nucleotide sequences to measure the non-genetic target molecules (e.g., but not limited to proteins), but also the genetic materials (e.g., but not limited to DNA/RNA) from cells.

Accordingly, in some embodiments, the methods, systems and/or kits described herein for detection of non-genetic target molecules (e.g., but not limited to proteins) can be used in combination with a nuclei acid analysis for genetic materials, for example, to study the non-genetic target molecules (e.g., but not limited to proteins) that interact with genetic materials or genetic regulatory elements. In these embodiments, the methods and systems described herein for detecting a plurality of target molecules in a sample as described herein can further comprise extracting a nucleic acid molecule from the same sample in which target molecules are to be detected. In some embodiments, the methods and systems described herein can further comprise subjecting the extracted nucleic acid molecule to a nucleic acid analysis. Various methods can be used for nucleic acid analysis, including, but not limited to sequencing, next generation sequencing, quantitative polymerase chain reaction (PCR), multiplexed (PCR), DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing, nanopore DNA sequencing, sequencing by hybridization, sequencing with mass spectrometry, microfluidic Sanger sequencing, microscopy-based sequencing techniques, RNA polymerase (RNAP) sequencing, fluorescence hybridization-based technology (e.g., but not limited to nanoString nCounter® technology), any art-recognized nucleic acid detection methods, or any combinations thereof.

In some embodiments, after a sample and/or non-genetic target molecules have been labeled with a plurality of target probes described herein, the identification nucleotide sequences of the target probes can be released from the bound non-genetic target molecules simultaneously with extraction of nucleic acid molecules (cells' genetic materials) from the same labeled sample. In these embodiments, both the nucleic acid molecules (cells' genetic materials) of interest and the identification nucleotide sequences can be detected simultaneously in a single sample mixture. In one embodiment, both the nucleic acid molecules (cells' genetic materials) of interest and the identification nucleotide sequences can be detected simultaneously in a single sample mixture using nanoString nCounter® analysis system, for example, as described in U.S. Pat. No. 8,415,102, the content of which is incorporated herein by reference. In this embodiment, once the nucleic acid molecules (genetic materials) from cells and the released identification nucleotide sequences are in solution, the solution mixture can be contacted with probe sets comprising both reporter probes and capture probes as described herein for the identification nucleotide sequences as well as for the cell's nucleic acid molecules (cells' genetic materials) of interest. One of the advantages of using nanoString nCounter® hybridization technology is that the analysis can be done on cell lysates, as well as on fixed samples, without the need for amplification that can introduce bias, and with minimal hands-on time preparation. However, other art-recognized methods for nucleic acid analyses or genetic analysis as described herein (e.g., but not limited to sequencing) can also be used for simultaneous detection of both nucleic acid molecules (cells' genetic materials) of interest and released identification nucleotide sequences from bound non-genetic target molecules. For example, in the case of sequencing, both the cells' genetic materials (e.g., DNA and/or mRNA) and the identification nucleotide sequences corresponding non-genetic target molecules can be sequenced together.

In alternative embodiments, nucleic acid molecules can be extracted from a first portion of a sample, while non-genetic target molecules can be independently derived or obtained from a second portion of the same sample. In these embodiments, the nucleic acid molecules of interest and the non-genetic target molecules can be detected separately to determine expression levels of the nucleic acid molecules of interest and non-genetic target molecules in the same sample. The nucleic acid molecules of interests can be subjected to any art-recognized nucleic acid analysis, while the non-genetic target molecules can be detected through detecting and identifying the corresponding identification nucleotide sequences released from the target probes using the methods, systems and/or kits described herein.

In some embodiments, the methods, systems and/or kits described herein can be adapted to measure proteins and nucleic acid molecules (cells' genetic materials) present in the same sample. For example, the proteins can be labeled by one or more embodiments of the target probes described herein and detected using the methods, systems and/or kits described herein, while the nucleic acid molecules (cells' genetic materials) can be detected separately or simultaneously by any methods known in the art (e.g., using, in one embodiment, nanoString nCounter® gene expression kit), e.g., for a multi-analyte assay on the same sample. In one embodiment, the sample can comprise cancer cells. The multi-analyte assay can enable generation of an integrated expression profiling for the sample, which can provide information on interaction between the proteins and the nucleic acid molecules, e.g., genetic regulatory elements such as microRNAs. This would be valuable or desirable in cases where rare samples with only limited sample size are available. For example, after labeling a sample or cells or non-genetic target molecules (e.g., proteins) with the target probes each comprising an unique identification nucleotide sequence (where in one embodiment, the identification nucleotide sequences are alien or foreign DNA barcodes), the identification nucleotide sequences (e.g., alien or foreign DNA barcodes) can then be released from the bound cells or target molecules (e.g., proteins) simultaneously with nucleic acid molecules (e.g., RNA and/or DNA) from the same sample or cells, e.g., using lysis buffer with or without additional cleaving agents (e.g., but not limited to, UV and/or chemical agents). Once the nucleic acid molecules (e.g., RNA and/or DNA) from the cells and unique identification nucleotide sequences (e.g., alien DNA barcodes) are in solution, a hybridization assay can be performed. In one embodiment, the hybridization assay can be nanoString nCounter® analysis assay. In the nCounter® analysis assay, the probe sets can have both reporter probes and capture probes as described herein for the identification nucleotide sequences (e.g., alien DNA barcodes) as well as for the genes of interest. If sample size is not a concern, a sample can be aliquoted or split such that the protein assay and gene expression assay can be run separately to get a readout of both mRNA and protein on the same sample (e.g., a certain population of cells).

In some embodiments, to optimize the nanoString nCounter® hybridization technology for detection of identification nucleotide sequences and/or cells' genetic materials, one can, for example, make sure that all the probes fall into a linear range when counting them in bulk and expression of one does not saturate the system. This can readily be done with optimization by one of skill in the art depending on the kit of interest.

In another embodiment, by releasing identification nucleotide sequences from bound target molecules (e.g., proteins), genetic material and the identification nucleotide sequences can be concurrently extracted from a single sample, enabling analyses of protein-DNA-RNA interrelationships.

While the methods described herein are described in the context where the identification nucleotide sequences are released from bound target probes before detection, in some embodiments, the identification nucleotide sequences do not need to be released from the bound target probes. Accordingly, in some embodiments, the methods described herein can also apply when the identification nucleotide sequences remain bound to target probes during detection.

In certain embodiments, the methods of detection are performed in multiplex assays, whereby a plurality of target molecules are detected in the same assay (a single reaction mixture). In a one embodiment, the assay is a hybridization assay in which the plurality of target molecules are detected simultaneously. In certain embodiments, the plurality of target molecules detected in the same assay is, at least 2 different target molecules, at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 different target molecules, or up to 5000 different target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, or from 500 to 5000 different target molecules.

Target Probes

As used herein, the term "target probe" generally refers to a synthetic molecule that specifically binds to a target molecule for identification and detection. In accordance with various aspects described herein, each target probe comprises: (i) a target-binding molecule that specifically binds to a target molecule in a sample; (ii) an identification nucleotide sequence that identifies the target-binding molecule; and (iii) a cleavable linker between the target-binding molecule and the identification nucleotide sequence.

In some embodiments, the cleavable linker does not comprise a polynucleotide sequence (e.g., a single-stranded polynucleotide sequence) that is complementary (for base-pairing) to at least a portion of the identification nucleotide sequence. That is, in these embodiments, the identification nucleotide sequence is not released from a target-binding molecule by detaching from the complementary polynucleotide sequence coupled to the target-binding molecule. Accordingly, in some embodiments, a target probe comprises (i) a target-binding molecule that specifically binds to the target molecule present in the sample; (ii) an identification nucleotide sequence that identifies the target-binding molecule; and (iii) a cleavable, non-hybridizable linker between the target-binding molecule and the identification nucleotide sequence.

Target-binding molecules: A target-binding molecule is a molecule that specifically binds to target molecule in a sample. As used herein, the term "specifically bind(s)" or "specific binding" refers to a target binding molecule that binds to a target molecule with a greater affinity than when it binds to other non-target molecule under the same conditions. Specific binding is generally indicated by a dissociation constant of 1 µM or lower, e.g., 500 nM or lower, 400 nM or lower, 300 nM or lower, 250 nM or lower, 200 nM or lower, 150 nM or lower, 100 nM or lower, 50 nM or lower, 40 nM or lower, 30 nM or lower, 20 nM or lower, 10 nM or lower, or 1 nM or lower. Typically the nature of the interaction or binding is noncovalent, e.g., by hydrogen, electrostatic, or van der Waals interactions, however, binding can also be covalent. Target-binding molecules can be naturally-occurring, recombinant or synthetic. Examples of the target-binding molecule can include, but are not limited to a nucleic acid, an antibody or a portion thereof, an antibody-like molecule, an enzyme, an antigen, a small molecule, a protein, a peptide, a peptidomimetic, a carbohydrate, an aptamer, and any combinations thereof. In some embodiments, the target-binding molecule does not include a nucleic acid molecule.

In some embodiments, the target-binding molecules can be modified by any means known to one of ordinary skill in the art. Methods to modify each type of target-binding molecules are well recognized in the art. Depending on the types of target-binding molecules, an exemplary modification includes, but is not limited to genetic modification, biotinylation, labeling (for detection purposes), chemical modification (e.g., to produce derivatives or fragments of the target-binding molecule), and any combinations thereof. In some embodiments, the target-binding molecule can be genetically modified. In some embodiments, the target-binding molecule can be biotinylated.

In some embodiments, the target-binding molecule can comprise an antibody or a portion thereof, or an antibody-like molecule. An antibody or a portion thereof or antibody-like molecule can detect expression level of a cellular protein (including cell surface proteins, secreted proteins, cytoplasmic proteins, and nuclear proteins), or phosphorylation or other post-translation modification state thereof. In some embodiments, the antibody or a portion thereof or antibody-like molecule can specifically bind to a protein marker present in a rare cell. Examples of a rare cell include, but are not limited to a circulating tumor cell, a fetal cell, and/or a stem cell. In some embodiments, the antibody or a portion thereof or antibody-like molecule can specifically bind to a target marker or protein associated with a condition (e.g., a normal healthy state, or a disease or disorder). In some embodiments, the antibody or a portion thereof or antibody-like molecule can specifically bind to a target marker or protein associated with cancer. For example, target markers or proteins associated with cancer can be involved in apoptosis, epigenetic, DNA damage, kinases/ oncogenes, cancer diagnostic markers, epithelial-mesenchymal transition, autophagy, proliferation, and/or immune response.

In some embodiments, the target-binding molecule can comprise a cell surface receptor ligand. As used herein, a "cell surface receptor ligand" refers to a molecule that can bind to the outer surface of a cell. Exemplary cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors.

In some embodiments, the target-binding molecule comprises an antibody selected from Table 1 in the Example, or a fragment thereof.

In some embodiments, the target-binding molecules of the target probes used in the methods described herein can comprise at least a portion or all of the antibodies listed in Table 1 in the Example, or fragments thereof.

Identification nucleotide sequences: As used herein, the term "identification nucleotide sequence" refers to a nucleotide sequence that identifies a specific target-binding molecule. Thus, each identification nucleotide sequence acts as a unique identification code for each target-binding molecule to which it was coupled.

In some embodiments, the identification nucleotide sequences have minimal or no secondary structures such as any stable intra-molecular base-pairing interaction (e.g., hairpins). Without wishing to be bound by theory, in some embodiments, the minimal secondary structure in the identification nucleotide sequences can provide for better hybridization between a first portion of the identification nucleotide sequence and the reporter probe, and/or between a second portion of the identification nucleotide sequence and the capture probe. In addition, the minimal secondary structure in the identification nucleotide sequence can provide for better binding of the target-binding molecule to the corresponding target molecule. In some embodiments, the identification nucleotide sequences described herein have no significant intra-molecular pairing at a pre-determined annealing temperature. The pre-determined annealing temperature can range from about 65° C.-80° C. or from about 70° C.-80° C., or at about 70° C.-75° C.

In some embodiments, identification nucleotide sequences of the target probes described herein can be selected or designed such that they do not cross-react with or bind to any nucleic acid sequence in a genome of a subject whose sample is being evaluated. Thus, the identification nucleotide sequences of the target probes used to detect target molecules in a subject's sample can be selected or designed based on nucleotide sequences of a species or genus that share a homology (sequence identity) with that of the subject by no more than 50% or less, including, e.g., no more than 40%, no more than 30%, no more than 20%, no more than 10% or less. In some embodiments, the identification nucleotide sequences can be pre-screened for no homology against major organisms (e.g., but not limited to human and/or other mammals) in the NCBI Reference Sequence (RefSeq) database. By way of example only, in some embodiments, the identification nucleotide sequences of the target probes used in an animal's sample (e.g., a mammal such as a human) can be derived from a plant genome. In one embodiment, the identification nucleotide sequences of the target probes used in a human's sample can be derived from a potato genome. In some embodiments, the identification nucleotide sequence can comprise a sequence selected from Table 2 (SEQ ID NO: 1 to SEQ ID NO: 110), or a fragment thereof.

Generally, identification nucleotide sequences of the target probes can have any sequence length and can vary depending on a number of factors, including, but not limited to detection methods, and/or the number of target molecules to be detected. For example, in some embodiments, the length of the identification nucleotide sequences can increase to provide sufficient identification of a large number of target molecules in a sample. In some embodiments where a hybridization-based method is used to detect identification nucleotide sequences, the identification nucleotide sequences can have a length sufficient to provide reliable binding to complementary reporter probes and/or capture probes and to generate detectable signals. In some embodiments, the identification nucleotide sequences can have a length of about 30-150 nucleotides, or about 30-100 nucleotides, or about 50-100 nucleotides. In some embodiments, the identification nucleotide sequences can have a length of at least about 30, at least 40, at least 50, at least 60, at least 70, at least 80, at least 90, at least 100 or more nucleotides. In some embodiments, the identification nucleotide sequences can have a length of about 70 nucleotides.

In some embodiments, the identification nucleotide sequences described herein can have a fairly consistent melting temperature (Tm). Without wishing to be bound by theory, the Tm of the identification nucleotide sequences described herein refers to the temperature at which 50% of the oligonucleotide and its complement are in duplex. The consistent Tm among a population of the identification nucleotide sequences allows for the synthesis and hybridization procedures to be tightly optimized, as the optimal conditions are substantially the same for all spots and positions. In some embodiments, the Tm of an identification nucleotide sequence when hybridized to its complementary reporter probes and/or capture probes can be selected to minimize any potential formation of secondary structures (e.g., hairpins) that could interfere with probe hybridization. In some embodiments, the Tm of an identification nucleotide sequence when hybridized to its complementary reporter probes and/or capture probes can range from about 70-90° C., from about 75-85° C., or from about 79-82° C. In some embodiments, the Tm of an identification nucleotide sequence when hybridized to its complementary reporter probes and/or capture probes can be at least 70° C., at least 75° C., at least 80° C., at least 85° C. or higher. In some embodiments, the Tm of an identification nucleotide sequence when hybridized to its complementary reporter probes and/or capture probes can be about 80° C.

The GC content of the identification nucleotide sequences can vary depending on a number of factors including, e.g., desired lengths of reporter probes and/or capture probes described and/or desired Tm temperatures. For example, when the reporter and/or capture probes are shorter, the GC content of the identification nucleotide sequences can be increased to maintain the desired Tm consistent between the reporter and/or capture probes and identification nucleotide sequences to minimize potential formation of secondary structures (e.g., hairpins) that could interfere with probe hybridization. In one embodiment, the GC content of the identification nucleotide sequence is optimized to maintain the Tm of an identification nucleotide sequence when hybridized to its complementary reporter probes and/or capture probes to be about 80° C.

In some embodiments, the identification nucleotide sequences have a balanced GC content. For example, in some embodiments, no single nucleotide in the identification nucleotide sequence can run longer than 3 nt. For example, no G nucleotide or C nucleotide runs longer than 3 nt in the identification nucleotide sequence. In one embodiment where the reporter and/or capture probes have a length of about 35 nucleotides, the GC content can be optimized to maintain the Tm of the corresponding identification nucleotide sequences to be about 80° C.; where the identification nucleotide sequence should have a balanced GC content as much as possible to avoid local regions of very high GC or poly C/poly G runs.

In some embodiments, the identification nucleotide sequences are DNA sequences.

Cleavable linkers: As used herein, the term "cleavable linker" refers to a linker which is sufficiently stable under one set of conditions, but which is cleaved under a different set of conditions to release the two parts the linker is holding together. In some embodiments, the cleavable linker can be cleaved at least 1.5 times or more (including, e.g., at least 2 times, at least 3 times, at least 4 times, at least 5 times, at least 6 times, at least 7 times, at least 8 times, at least 9 times, at least 10 times, at least 20 times, at least 30 times, at least 40 times, at least 50 times or more) faster under a first reference condition (e.g., with a cleaving agent) than under a second reference condition (e.g., without a cleaving agent).

For example, a cleavable linker couples an identification nucleotide sequence and a target-binding agent together under one set of conditions and can be cleaved, digested or degraded under a different set of conditions to release the identification nucleotide sequence. The cleavable linker coupling a target-binding molecule to an identification nucleotide sequence in a target probe can control release of the identification nucleotide sequence from the target probe when needed, e.g., upon binding to a target molecule, such that the identification nucleotide can be released for detection. Cleavable linkers are known in the art, of which examples include, but are not limited to the ones that are sensitive to an enzyme, pH, temperature, light, shear stress, sonication, a chemical agent (e.g., dithiothreitol), or any combination thereof. In some embodiments, the cleavable linker can be sensitive to light and protein degradation, e.g., by an enzyme.

Cleavable linkers are susceptible to cleavage agents, e.g., hydrolysis, pH, redox potential, and light (e.g., infra-red, and/or UV) or the presence of degradative molecules. Examples of such degradative agents include: redox agents which are selected for particular substrates or which have no substrate specificity, including, e.g., oxidative or reductive enzymes or reductive agents such as mercaptans, present in cells, that can degrade a redox cleavable linker by reduction; esterases; amidases; endosomes or agents that can create an acidic environment, e.g., those that result in a pH of five or lower; enzymes that can hydrolyze or degrade an acid cleavable linker by acting as a general acid, peptidases (which can be substrate specific) and proteases, and phosphatases. In some embodiments, the cleavable linker can be cleavable by a particular enzyme.

In some embodiments, the cleavable linker is a cleavable, non-hybridizable linker. As used herein, the term "cleavable, non-hybridizable linker" refers to a cleavable linker as defined earlier that does not comprise a polynucleotide sequence (e.g., a single-stranded polynucleotide sequence) complementary (for basepairing) to at least a portion of the identification nucleotide sequence described herein. That is, in these embodiments, the identification nucleotide sequence is not released from the target-binding molecule by detaching from the complementary polynucleotide sequence coupled to the target-binding molecule.

Exemplary cleavable, non-hybridizable linkers include, but are not limited to, hydrolyzable linkers, redox cleavable linkers (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linkers (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(OR)—S—, —S—P(S)(OR)—O—, —O—P(O)(R)—O—, —O—P(S)(R)—O—, —S—P(O)(R)—O—, —S—P(S)(R)—O—, —O—P(O)(R)—S—, —O—P(S)(R)—S—, . —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C1-C10 alkyl); acid cleavable linkers (e.g., hydrazones, esters, and esters of amino acids, —C=NN— and —OC(O)—); ester-based cleavable linkers (e.g., —C(O)O—); peptide-based cleavable linkers, (e.g., linkers that are cleaved by enzymes such as peptidases and proteases in cells, e.g., —NHCHR$^A$C(O)NHCHR$^B$C(O)—, where R$^A$ and R$^B$ are the R groups of the two adjacent amino acids), photocleavable linkers and any combinations thereof. A peptide based cleavable linker comprises two or more amino acids. In some embodiments, the peptide-based cleavage linkage comprises the amino acid sequence that is the substrate for a peptidase or a protease. In some embodiments, an acid cleavable linker is cleavable in an acidic environment with a pH of about 6.5 or lower (e.g., about 6.5, 6.0, 5.5, 5.0, or lower), or by agents such as enzymes that can act as a general acid.

In some embodiments, the cleavable, non-hybridizable linker can comprise a disulfide bond, a tetrazine-trans-cyclooctene group, a sulfhydryl group, a nitrobenzyl group, a nitoindoline group, a bromo hydroxycoumarin group, a bromo hydroxyquinoline group, a hydroxyphenacyl group, a dimethozybenzoin group, or any combinations thereof.

Figure 2A:
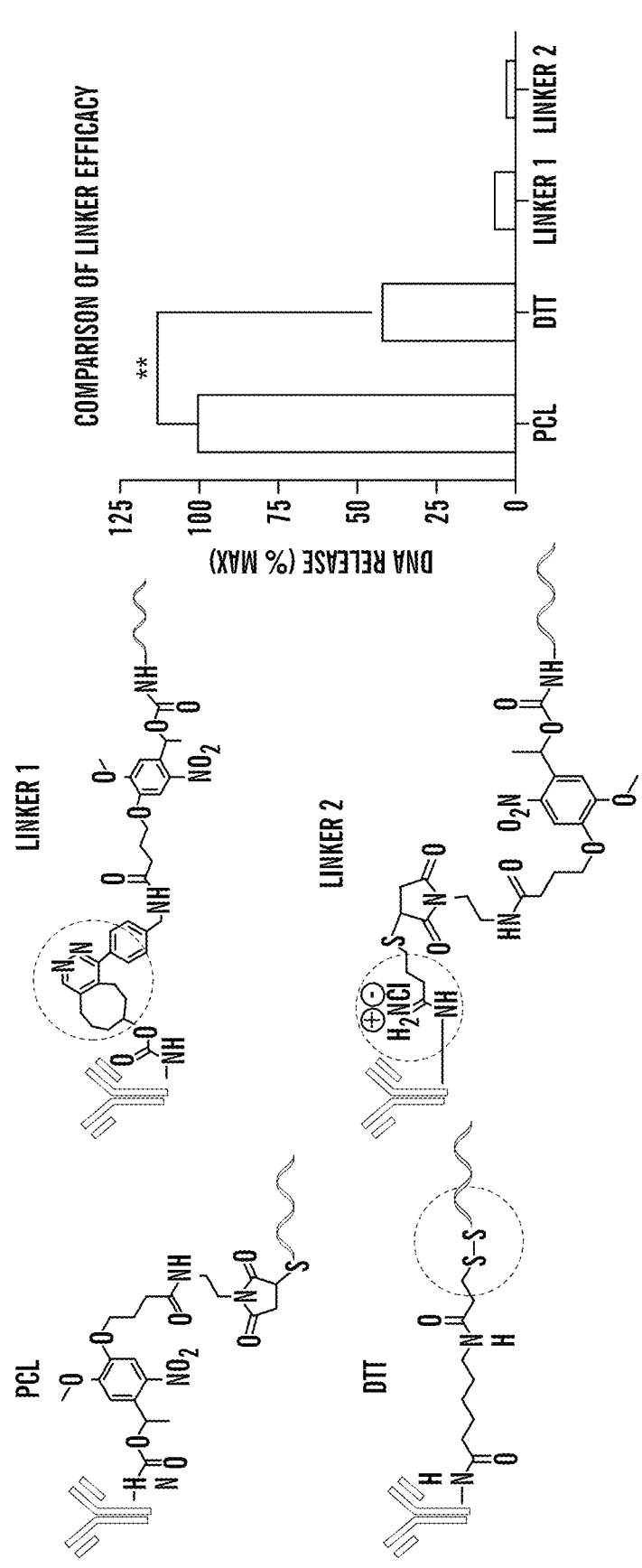
FIGS. 2A-2B shows an exemplary scheme of DNA-antibody conjugation.

In some embodiments, the cleavable, non-hybridizable linker can comprise at least one of the linkers shown in FIG. 2A.

In some embodiments, the cleavable, non-hybridizable linker can comprise a photocleavable linker. A photocleavable linker is a linker that can be cleaved by exposure to electromagnetic radiation (e.g., visible light, UV light, infrared, etc.). The wavelength of light necessary to photocleave the linker is dependent upon the structure of the photocleavable linker used. Any art-recognized photocleavable linker can be used for the target probes described herein. Exemplary photocleavable linker include, but are not limited to, chemical molecules containing an o-nitrobenzyl moiety, a p-nitrobenzyl moiety, a m-nitrobenzyl moiety, a nitoindoline moiety, a bromo hydroxycoumarin moiety, a bromo hydroxyquinoline moiety, a hydroxyphenacyl moiety, a dimethozybenzoin moiety, or any combinations thereof.

Additional exemplary photocleavable groups are generally described and reviewed in Pellicchioli et al., Photoremovable protecting groups: reaction mechanisms and applications, Photochem. Photobiol. Sci. 1 441-458 (2002); Goeldner and Givens, Dynamic Studies in Biology, Wiley-VCH, Weinheim (2005); Marriott, Methods in Enzymology, Vol. 291, Academic Press, San Diego (1998); Morrison, Bioorganic Photochemistry, Vol. 2, Wiley, New York (1993); Adams and Tsien, Annu. Rev. Physiol. 55 755-784 (1993); Mayer et al., Biologically Active Molecules with a "Light Switch," Angew. Chem. Int. Ed. 45 4900-4921 (2006); Pettit et al., Neuron 19 465-471 (1997); Furuta et al., Brominated 7-hydroxycoumarin-4-ylmethyls: Photolabile protecting groups with biologically useful cross-sections for two photon photolysis, Proc. Natl. Acad. Sci. USA 96 1 193-1200 (1999); and U.S. Pat. Nos. 5,430,175; 5,635,608; 5,872,243; 5,888,829; 6,043,065; and Zebala, U.S. Patent Application No. 2010/0105120, the disclosures of which are incorporated by reference herein.

In some embodiments, the photocleavable linker can generally be described as a chromophore. Examples of chromophores which are photoresponsive to such wavelengths include, but are not limited to, acridines, nitroaromatics, and arylsulfonamides. The efficiency and wavelength at which the chromophore becomes photoactivated and thus releases the identification nucleotide sequences described herein will vary depending on the particular functional group(s) attached to the chromophore. For example, when using nitroaromatics, such as derivatives of o-nitrobenzylic compounds, the absorption wavelength can be significantly lengthened by addition of methoxy groups.

In some embodiments, the photocleavable linker can comprise a nitro-aromatic compound. Exemplary photocleavable linkers having an ortho-nitro aromatic core scaffold include, but are not limited to, ortho-nitro benzyl ("ONB"), 1-(2-nitrophenyl)ethyl ("NPE"), alpha-carboxy-2-nitrobenzyl ("CNB"), 4,5-dimethoxy-2-nitrobenzyl ("DMNB"), 1-(4,5-dimethoxy-2-nitrophenyl)ethyl ("DM-NPE"), 5-carboxymethoxy-2-nitrobenzyl ("CMNB") and ((5-carboxymethoxy-2-nitrobenzyl)oxy)carbonyl ("CMNCBZ") photolabile cores. It will be appreciated that the substituents on the aromatic core are selected to tailor the wavelength of absorption, with electron donating groups (e.g., methoxy) generally leading to longer wavelength absorption. For example, nitrobenzyl ("NB") and nitrophenylethyl ("NPE") are modified by addition of two methoxy residues into 4,5-dimethoxy-2-nitrobenzyl and 1-(4,5-dimethoxy-2-nitrophenyl)ethyl, respectively, thereby increasing the absorption wavelength range to 340-360 nm.

Further, other ortho-nitro aromatic core scaffolds include those that trap nitroso byproducts in a hetero Diels Alder reaction as generally discussed in Zebala, U.S. Patent Application No. 2010/0105120 and Pirrung et al., J. Org. Chem. 68: 1 138 (2003). The nitrodibenzofurane ("NDBF") chromophore offers an extinction coefficient significantly higher in the near UV region but it also has a very high quantum yield for the deprotection reaction and it is suitable for two-photon activation (Momotake et al, The nitrodibenzofuran chromophore: a new caging group for ultra-efficient photolysis in living cells, Nat. Methods 3 35-40 (2006)). The NPP group is an alternative introduced by Pfleiderer et al. that yields a less harmful nitrostyryl species (Walbert et al., Photolabile Protecting Groups for Nucleosides: Mechanistic Studies of the 2-(2-Nitrophenyl)ethyl Group, Helv. Chim. Acta 84 1601-161 1 (2001)).

In exemplary embodiments involving UV light, the photocleavable linkers can be selected from the group consisting of alpha-carboxy-2-nitrobenzyl (CNB, 260 nm), 1-(2-nitrophenyl)ethyl (NPE, 260 nm), 4,5-dimethoxy-2-nitrobenzyl (DMNB, 355 nm), 1-(4,5-dimethoxy-2-nitrophenyl)ethyl (DMNPE, 355 nm), (4,5-dimethoxy-2-nitrobenzoxy)carbonyl (NVOC, 355 nm), 5-carboxymethoxy-2-nitrobenzyl (CMNB, 320 nm), ((5-carboxymethoxy-2-nitrobenzyl)oxy) carbonyl (CMNCBZ, 320 nm), desoxybenzoinyl (desyl, 360 nm), and anthraquino-2-ylmethoxycarbonyl (AQMOC, 350 nm).

Other suitable photocleavable linkers are based on the coumarin system, such as BHC (Furuta and Iwamura, Methods Enzymol. 291 50-63 (1998); Furuta et al., Proc. Natl. Acad. Sci. USA 96 1 193-1200 (1999); Suzuki et al., Org. Lett. 5:4867 (2003); U.S. Pat. No. 6,472,541, the disclosure of which is incorporated by reference herein). The DMACM linkage photocleaves in nanoseconds (Hagen et al., [7-

(Dialkylamino)coumarin-4-yl]methyl-Caged Compounds as Ultrafast and Effective Long-Wavelength Phototriggers of 8-Bromo-Substituted Cyclic Nucleotides, Chem Bio Chem 4 434-442 (2003)) and is cleaved by visible light (U.S. patent application Ser. No. 11/402,715 the disclosure of which is incorporated by reference herein). Coumarin-based photolabile linkages are also available for linking to aldehydes and ketones (Lu et al., Bhc-diol as a photolabile protecting group for aldehydes and ketones, Org. Lett. 5 2119-2122 (2003)). Closely related analogues, such as BHQ, are also suitable (Fedoryak et al., Brominated hydroxyquinoline as a photolabile protecting group with sensitivity to multiphoton excitation, Org. Lett. 4 3419-3422 (2002)). Another suitable photocleavable linker comprises the pHP group (Park and Givens, J. Am. Chem. Soc. 119:2453 (1997), Givens et al., New Phototriggers 9: p-Hydroxyphenacyl as a C-Terminal Photoremovable Protecting Group for Oligopeptides, J. Am. Chem. Soc. 122 2687-2697 (2000); Zhang et al., J. Am. Chem. Soc. 121 5625-5632, (1999); Conrad et al., J. Am. Chem. Soc. 122 9346-9347 (2000); Conrad et al., Org. Lett. 2 1545-1547 (2000)). A ketoprofen derived photolabile linkage is also suitable (Lukeman et al., Carbanion-Mediated Photocages: Rapid and Efficient Photorelease with Aqueous Compatibility, J. Am. Chem. Soc. 127 7698-7699 (2005)).

In some embodiments, a photocleavable linker is one whose covalent attachment to an identification nucleotide sequence and/or target-binding agent is reversed (cleaved) by exposure to light of an appropriate wavelength. In some embodiments, release of the identification nucleotide sequences occurs when the conjugate is subjected to ultraviolet light. For example, photorelease of the identification nucleotide sequences can occur at a wavelength ranging from about 200 to 380 nm (the exact wavelength or wavelength range will depend on the specific photocleavable linker used, and can be, for example, 200, 210, 220, 230, 240, 250, 260, 270, 280, 290, 300, 310, 320, 330, 340, 350, 360, 370, or 380 or some range therebetween). In some embodiments, release of the identification nucleotide sequences occurs when the conjugate is subjected to visible light. For example, photorelease of the identification nucleotide sequences can occur at a wavelength ranging from about 380 to 780 nm (the exact wavelength or wavelength range will depend on the specific photocleavable linker used, and could be, for example, 380, 400, 450, 500, 550, 600, 650, 700, 750, or 780, or some range therebetween). In some embodiments, release of the identification nucleotide sequences occurs when the conjugate is subjected to infrared light. For example, photorelease of the identification nucleotide sequences can occur at a wavelength ranging from about 780 to 1200 nm (the exact wavelength or wavelength range will depend on the specific photocleavable linker used, and could be for example, 780, 800, 850, 900, 950, 1000, 1050, 1100, 1150, or 1200, or some range therebetween).

In some embodiments, a photocleavable linker can be selected from the group consisting of molecules (i)-(xiv) and any combinations thereof, wherein the chemical structures of the molecules (i)-(xiv) are shown as follows:

(i)
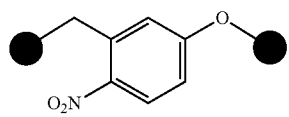

(ii)
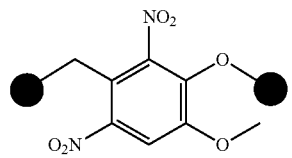

(iii)
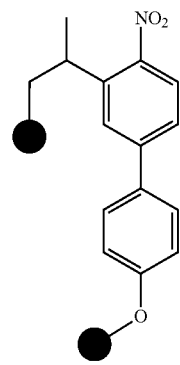

(iv)
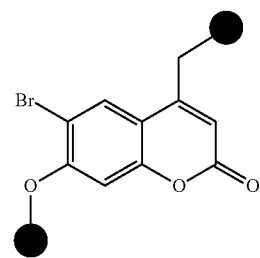

(v)
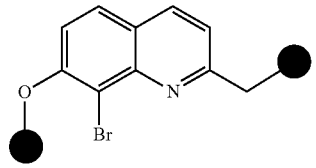

(vi)
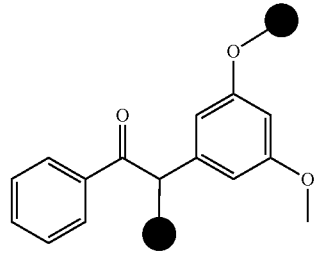

(vii)
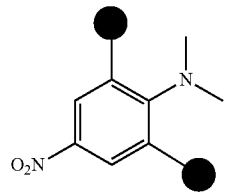

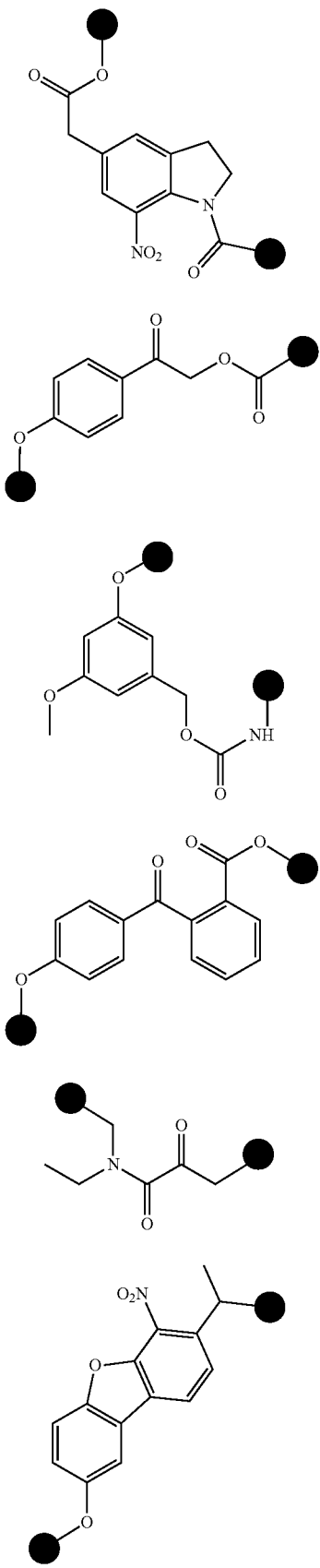
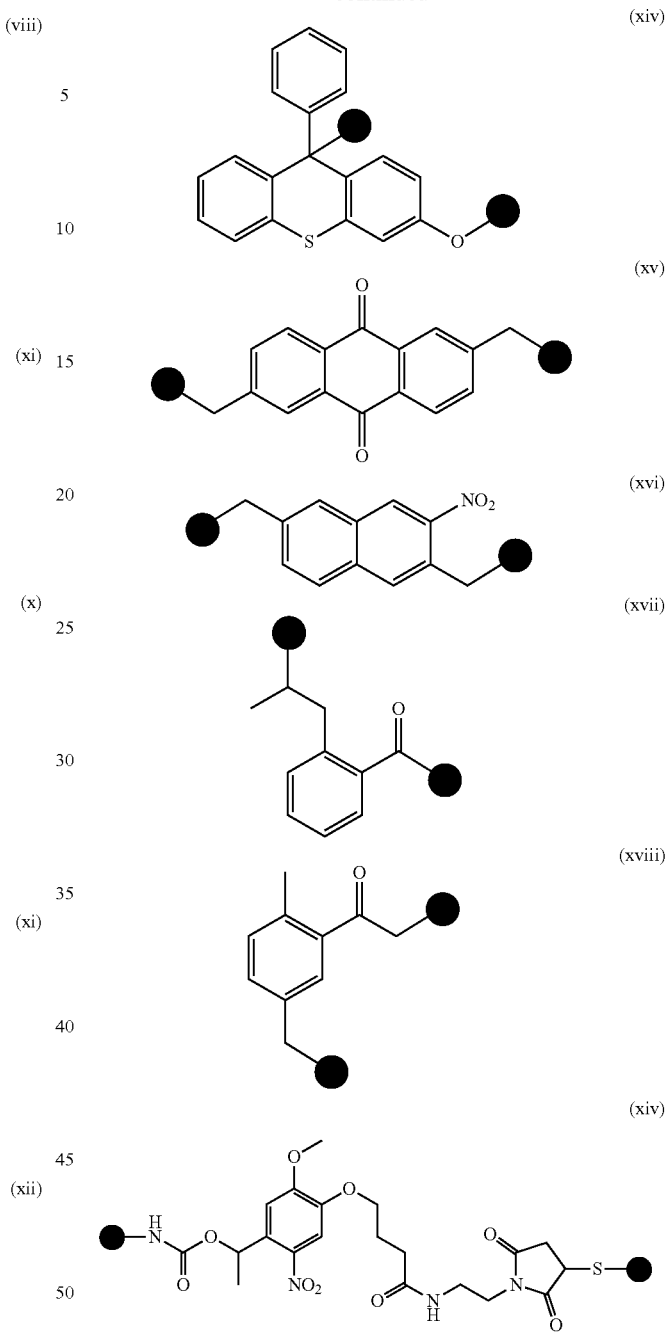

where each of the black dots in each molecule represents a connecting or coupling point that connects, directly or indirectly, to a target-binding molecule described herein or an identification nucleotide sequence described herein. The connecting point can be a bond, or comprise an atom, a molecule, and/or a linker described herein. In some embodiments, the connecting point is a bond.

In some embodiments, the photocleavable linker can comprise the molecule (xiv).

In some embodiments, the photocleavable linker is a photocleavable bifunctional linker. In some embodiments, the photocleavable linker is a photocleavable multi-functional linker.

In some embodiments where a photocleavable linker is used, the identification nucleotide sequences can be released from the bound target probes by exposing the bound target probes to a light of a specified wavelength. In some embodiments, ultraviolet (UV) light or near UV light can be used to release identification nucleotide sequences from bound target probes. In some embodiments, release of the identification nucleotide sequences can occur at a wavelength ranging from about 200 nm to about 450 nm.

Activation agents can be used to activate the components to be conjugated together (e.g., identification nucleotide sequences and/or target-binding molecules). Without limitations, any process and/or reagent known in the art for conjugation activation can be used. Exemplary surface activation method or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, sulfosuccinimidyl 6-[3'(2-[pyridyldithio)-propionamido] hexanoate (sulfo-LC-SPDP), 2-iminothiolane (Traut's agent), trans-cyclooctene N-hydroxy-succinimidyl ester (TCO-NHS), surface activation through plasma treatment, and the like.

Again, without limitations, any art known reactive group can be used for coupling a photocleavable linker between an identification nucleotide sequence and a target-binding molecule. For example, various surface reactive groups can be used for surface coupling including, but not limited to, alkyl halide, aldehyde, amino, bromo or iodoacetyl, carboxyl, hydroxyl, epoxy, ester, silane, thiol, and the like.

Control Probes

As used herein, the term "control probe" generally refers to a synthetic molecule that specifically binds to a control molecule for identification and detection. In accordance with various aspects described herein, each control probe comprises: (i) a control-binding molecule that specifically binds to a control molecule in a sample; (ii) an identification control sequence that identifies the control-binding molecule; and (iii) a cleavable linker between the control-binding molecule and the identification control sequence.

Control-binding molecules: A control-binding molecule is a molecule that specifically binds to a control molecule in a sample. Examples of a control protein include, but are not limited to, housekeeping proteins (e.g., GAPDH, actin and/or tubulin), control IgG isotypes, mutant non-functional or non-binding proteins (e.g., nonfunctional or non-binding antibodies, or mutated proteins such as a protein G that has been mutated at the binding site), and any combinations thereof. Typically the nature of the interaction or binding is noncovalent, e.g., by hydrogen, electrostatic, or van der Waals interactions, however, binding can also be covalent. Control-binding molecules can be naturally-occurring, recombinant or synthetic. Examples of the control-binding molecule can include, but are not limited to a nucleic acid, an antibody or a portion thereof, an antibody-like molecule, an enzyme, an antigen, a small molecule, a protein, a peptide, a peptidomimetic, a carbohydrate, an aptamer, and any combinations thereof. In some embodiments, the control-binding molecule does not include a nucleic acid molecule.

In some embodiments, the control-binding molecules can be modified by any means known to one of ordinary skill in the art. Methods to modify each type of control-binding molecules are well recognized in the art. Depending on the types of control-binding molecules, an exemplary modification includes, but is not limited to genetic modification, biotinylation, labeling (for detection purposes), chemical modification (e.g., to produce derivatives or fragments of the control-binding molecule), and any combinations thereof. In some embodiments, the control-binding molecule can be genetically modified. In some embodiments, the control-binding molecule can be biotinylated.

In some embodiments, the control-binding molecule can comprise an antibody or a portion thereof, or an antibody-like molecule. An antibody or a portion thereof or antibody-like molecule can detect expression level of a housekeeping protein, e.g., but not limited to GAPDH, actin, and/or tubulin. In some embodiments, the antibody or a portion thereof or antibody-like molecule can specifically bind to a control IgG isotype. In some embodiments, the antibody or a portion thereof or antibody-like molecule can specifically bind to a mutant non-function or non-binding protein, e.g., a protein G that has been mutated at the binding site.

Identification control sequences: As used herein, the term "identification control sequence" refers to a nucleotide sequence that identifies a specific control-binding molecule. Thus, each identification control sequence acts as a unique identification code for each control-binding molecule to which it was coupled.

In some embodiments, the identification control sequences have minimal or no secondary structures such as any stable intra-molecular base-pairing interaction (e.g., hairpins). Without wishing to be bound by theory, in some embodiments, the minimal secondary structure in the identification control sequences can provide for better hybridization between a first portion of the identification control sequence and the reporter probe, and/or between a second portion of the identification control sequence and the capture probe. In addition, the minimal secondary structure in the identification control sequence can provide for better binding of the control-binding molecule to the corresponding control molecule. In some embodiments, the identification control sequences described herein have no significant intra-molecular pairing at a pre-determined annealing temperature. The pre-determined annealing temperature can range from about 65° C.-80° C. or from about 70° C.-80° C., or at about 70° C.-75° C.

In some embodiments, identification control sequences of the control probes described herein can be selected or designed such that they do not cross-react with or bind to any nucleic acid sequence in a genome of a subject whose sample is being evaluated. Thus, the identification control sequences of the control probes used to detect control molecules in a subject's sample can be selected or designed based on nucleotide sequences of a species or genus that share a homology (sequence identity) with that of the subject by no more than 50% or less, including, e.g., no more than 40%, no more than 30%, no more than 20%, no more than 10% or less. By way of example only, in some embodiments, the identification control sequences of the control probes used in an animal's sample (e.g., a mammal such as a human) can be derived from a plant genome. In one embodiment, the identification control sequences of the control probes used in a human's sample can be derived from a potato genome. In some embodiments, the identification control sequence can comprise a sequence selected from Table 2 (SEQ ID NO: 1 to SEQ ID NO: 110), or a fragment thereof.

Generally, identification control sequences of the control probes can have any sequence length and can vary depending on a number of factors, including, but not limited to detection methods, and/or the number of control molecules to be detected. For example, in some embodiments, the length of the identification control sequences can increase to provide sufficient identification of a large number of control molecules in a sample. In some embodiments where a hybridization-based method is used to detect identification control sequences, the identification control sequences can have a length sufficient to provide reliable binding to complementary reporter probes and/or capture probes and to generate detectable signals. In some embodiments, the identification control sequences can have a length of about 30-150 nucleotides, or about 30-100 nucleotides, or about 50-100 nucleotides. In some embodiments, the identification control sequences can have a length of at least about 30, at least 40, at least 50, at least 60, at least 70, at least 80, at least 90, at least 100 or more nucleotides. In some embodiments, the identification control sequences can have a length of about 70 nucleotides.

In some embodiments, the identification control sequences described herein can have a fairly consistent melting temperature (Tm). Without wishing to be bound by theory, the Tm of the identification control sequences described herein refers to the temperature at which 50% of the oligonucleotide and its complement are in duplex. The consistent Tm among a population of the identification control sequences allows for the synthesis and hybridization procedures to be tightly optimized, as the optimal conditions are substantially the same for all spots and positions. In some embodiments, the Tm of an identification control sequence when hybridized to its complementary reporter probes and/or capture probes can range from about 70-90° C., from about 75-85° C., or from about 79-82° C. In some embodiments, the Tm of an identification control sequence when hybridized to its complementary reporter probes and/or capture probes can be at least 70° C., at least 75° C., at least 80° C., at least 85° C. or higher.

Cleavable linkers: Any cleavable linkers used in the target probes can be used in the control probes. In some embodiments, the cleavable linker comprises a photocleavable linker. In some embodiments, the photocleavable linker can be selected from the group consisting of molecules (i)-(xiv) shown herein and any combinations thereof. In some embodiments, the photocleavable linker can comprise the molecule (xiv).

Reporter Probes

As used herein, the term "reporter probe" generally refers to a synthetic molecule that binds a first portion of the identification nucleotide sequence of a target probe and generates a detectable signal that is distinguishable for the reporter probe and the bound identification nucleotide sequence.

In some embodiments, the reporter probes have minimal or no secondary structures such as any stable intra-molecular base-pairing interaction (e.g., hairpins). Without wishing to be bound by theory, the minimal secondary structure in the reporter probes can provide for better hybridization between the reporter probe's backbone and a portion of the identification nucleotide sequences. In addition, the minimal secondary structure in the reporter probes can provide for better detection of the detectable label in the reporter probes. In some embodiments, the reporter probes described herein have no significant intra-molecular pairing at a pre-determined annealing temperature. The pre-determined annealing temperature can range from about 65° C.-80° C. or from about 70° C.-80° C., or at about 70° C.-75° C. Secondary structures can be predicted by programs known in the art such as MFOLD.

In various aspects described herein, a reporter probe generally comprises a detectable label that identifies the reporter probe. As used herein, the term "detectable label" refers to a composition capable of producing a detectable signal indicative of the presence of a target, e.g., a reporter probe bound to an identification nucleotide sequence of a target probe. Detectable labels include any composition detectable by spectroscopic, photochemical, biochemical, immunochemical, electrical, optical or chemical means. Suitable detectable labels can include fluorescent molecules, radioisotopes, nucleotide chromophores, enzymes, substrates, chemiluminescent moieties, bioluminescent moieties, and the like. As such, a detectable label is any composition detectable by spectroscopic, photochemical, biochemical, immunochemical, electrical, optical or chemical means needed for the methods and devices described herein.

In some embodiments, the detectable label of the reporter probes can comprise one or more labeling molecules that create a unique signal for each reporter probe. In some embodiments, the detectable label of the reporter probes can comprise one labeling molecule. In some embodiments, the detectable label of the reporter probes can comprise at least two or more (e.g., at least 2, at least 3, at least 4, at least 5, at least 6 or more) labeling molecules. As used herein, the term "labeling molecule" is a molecule that is capable of producing a detectable signal, which constitutes at least part of the detectable signal produced by the detectable label. Accordingly, a labeling molecule can be a fluorescent molecule, a radioisotope, a nucleotide chromophore, an enzyme, a substrate, a chemiluminescent moiety, a bioluminescent moiety, or any combinations thereof.

In some embodiments, the detectable label and/or labeling molecule(s) can generate an optical signal. The optical signal can be a light-emitting signal or a series or sequence of light-emitting signals. In some embodiments, labeling molecules for generation of an optical signal can comprise one or a plurality of (e.g., at least 2 or more, including, e.g., at least 3, at least 4, at least 5 or more) a fluorochrome moiety, a fluorescent moiety, a dye moiety, a chemiluminescent moiety, or any combinations thereof.

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor350™; Alexa Fluor430™; Alexa Fluor488™; Alexa Fluor 532™; Alexa Fluor546™; Alexa Fluor568™; Alexa Fluor594™; Alexa Fluor 633™; Alexa Fluor 647™; Alexa Fluor660™; Alexa Fluor680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™

CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66 W; Yellow GFP; YFP; YO-PRO-1; YO-PRO-3; YOYO-1; and YOYO-3. Many suitable forms of these fluorescent compounds are available and can be used.

Other exemplary detectable labels and/or labeling molecules include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such detectable labels and/or labeling molecules are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the detectable label and/or labeling molecules can comprise at least one or more (e.g., at least two, at least three, at least four, at least five, at least six, at least or seven or more) fluorophores or quantum dots. Without wishing to be bound by a theory, using a fluorescent reagent can reduce signal-to-noise in the imaging/readout, thus maintaining sensitivity. The color sequence of the labeling molecules in the detectable label can provide an identity to the corresponding reporter probe. For example, a reporter probe I comprises a detectable label with three fluorophores in the following order: fluorophore A; fluorophore B and fluorophore C; whereas a reporter probe II comprises a detectable label with the same three fluorophores but in a different order: fluorophore A; fluorophore C and fluorophore B. While the reporter probes I and II have the same fluorophores, the color sequences of the reporter probe I and reporter probe II are distinct, which identifies the individual reporter probes.

In some embodiments, the labeling molecule can comprise an enzyme that produces a change in color of an enzyme substrate. A variety of enzymes such as horseradish peroxidase (HRP) and alkaline peroxide (AP) can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like.

In some embodiments, the reporter probe can further comprise a first target probe-specific region that binds to a first portion of the identification nucleotide sequence of a target probe. Accordingly, in some embodiments, a reporter probe can comprise: (a) a first target probe-specific region that binds to a first portion of the identification nucleotide sequence; and (b) a detectable label that identifies the reporter probe.

As used herein, the term "first target probe-specific region" refers to a region of a reporter probe that binds to a first portion of the identification nucleotide sequence of a target probe. The first target probe-specific region can comprise a fairly regularly-spaced pattern of a nucleotide residue and/or a group (e.g., at least 2 or more) of nucleotide residues in the backbone. In some embodiments, a nucleotide residue and/or a group (e.g., at least 2 or more) of nucleotide residues can be spaced at least an average of 1, 2, 3, 4, 5, 6, 7, 8, 9, 10, 11, 12, 13, 4, 15, 20, 25, 30, 35, 40, 45, or 50 bases apart within the first target probe-specific region. This allows for a first target probe-specific region having a regularly spaced pattern of a nucleotide or a group of nucleotides binds to a nucleotide sequence that has a complementary nucleotide or a group of complementary nucleotides regularly spaced apart by about the same number of bases. For example, in some embodiments, when the first target probe-specific region contain a fairly regularly-spaced pattern of adenine residues in the backbone, it can bind a nucleotide sequence that has a thymine residue fairly regularly spaced apart by about the same of number of bases.

In some embodiments, at least 30% or more (including, e.g., at least 40%, at least 50%, at least 60%, at least 70%, at least 80%, at least 90%, at least 95%, at least 97%, at least 99%, or 100%) of the first target probe-specific region is complementary to a first portion of the identification nucleotide sequence. As used herein and throughout the specification, the term "complementary" refers to a first nucleic acid strand able to form hydrogen bond(s) with a second nucleic acid strand by either traditional Watson-Crick or other non-traditional types. A percent complementarity indicates the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will form hydrogen bonds with the same number of contiguous residues in a second nucleic acid sequence. Less than perfect complementarity refers to the situation in which some, but not all, nucleotides of two strands can form hydrogen bonds with each other. "Substantial complementarity" refers to polynucleotide strands exhibiting 90% or greater complementarity, excluding regions of the polynucleotide strands, such as overhangs, that are selected so as to be non-complementary. Specific binding requires a sufficient degree of complementarity to avoid non-specific binding of the oligomeric sequence to non-target sequences under conditions in which specific binding is desired, i.e., in vitro assays, under conditions in which the assays are performed. The non-target sequences typically differ by at least 1, 2, 3, 4, or 5 nucleotides.

In some embodiments, the first target probe-specific region can be identified for use in the reporter probe using the methods and computer systems described in U.S. Pat. No. 8,415,102 to NanoString Technologies, Inc.

In some embodiments, the first target probe-specific region and a detectable label can be coupled to each other by at least one or more linkers as described herein. In some embodiments, the linker between the first target probe-specific region and the detectable label can comprise an amide bond. In some embodiments, the linker between the first target probe-specific region and the detectable label can comprise a chemical linker as described herein.

In some embodiments, the detectable label and/or labeling molecules can be detected using an epifluorescent microscope. In some embodiments, the detectable label and/or labeling molecules can be detected using a fluorescent microscope.

In some embodiments, the detectable label and/or labeling molecules can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, the detectable label and/or labeling molecules can be detected through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel-Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy can be coupled to numerous fluorescent labels as have been described herein and as have been described in the art.

In some embodiments, the detectable label and/or labeling molecules can be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect the detectable label and/or labeling molecules. For example, in some embodiments, a first labeling molecule can be labeled with a fluorescent donor and second labeling molecule can be labeled with a fluorescent acceptor. Accordingly, such labeled first and second labeling molecules can be used within competition assays to detect the detectable label and/or labeling molecules. Numerous combinations of fluorescent donors and fluorescent acceptors can be used for detection.

In some embodiments, the detectable and/or labeling molecules can be detected through use of polynucleotide analysis. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described, for example, in U.S. Pat. Nos. 7,118,910 and 6,960,437; herein incorporated by reference). Such methods can be adapted to provide for detection of the detectable label and/or labeling molecules. In some embodiments, fluorescence quenching, molecular beacons, electron transfer, electrical conductivity, and the like can be used to analyze polynucleotide interaction. Such methods are known and have been described, for example, in Jarvius, DNA Tools and Microfluidic Systems for Molecular Analysis, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al, Proc. Natl. Acad. Sci, 100:7605-7610 (2003); Wang et al. Anal. Chem, 75:3941-3945 (2003); and Fan et al, Proc. Natl. Acad. Sci, 100:9134-9137 (2003) and in U.S. Pat. Nos. 6,958,216; 5,093,268; and 6,090,545, the content of all of which is incorporated herein by reference. In some embodiments, the polynucleotide analysis is by polymerase chain reaction (PCR). The fundamentals of PCR are well-known to the skilled artisan, see, e.g. McPherson, et al., PCR, A Practical Approach, IRL Press, Oxford, Eng. (1991), hereby incorporated by reference.

In some embodiments, the reporter probes can further comprise an affinity tag, which is described in detail in the "Capture probes" section below.

In some embodiments, an affinity tag is placed near or at one end of the reporter probe such that attachment of the reporter probe to a solid substrate surface does not significantly interfere with detection of the detectable label.

In some embodiments, the reporter probe(s) described herein refers to a "reporter probe" or "labeled nanoreporter probe" or "nanoreporter probe(s)" as described in the U.S. Pat. No. 8,519,115; and US Patent App. Pub. Nos. US 2014/0017688; US 2014/0037620; US2013/0017971; US 2013/0230851; US 2011/0201515; US 2011/0086774; US 2011/0229888; and US 2010/0261026, all of which are assigned to Nanostring Technologies, Inc. and are incorporated herein by reference.

Capture Probes

As used herein, the term "capture probe" generally refers to a synthetic molecule that binds a second portion of the identification nucleotide sequence of a target probe and optionally comprise an affinity tag. As used herein, the term "affinity tag" refers to a molecule that permits reversible or reversible immobilization of the capture probe and bound identification nucleotide sequence to a solid substrate surface, e.g., to allow visualization and/or imaging of the bound complex. In some embodiments, immobilization of the released identification nucleotide sequences can provide distinguishable spatial signals that identify the capture probes coupled to the released identification nucleotide sequences. Examples of a solid substrate include, but are not limited to, a microfluidic device, a cartridge, a microtiter plate, a tube, a magnetic particle, a scaffold, and an array.

The affinity tag of the capture probe can attach to a solid substrate surface through a covalent or non-covalent interaction. The immobilization or attachment of the affinity tag to a solid substrate surface can occur covalently or non-covalently using any of the methods known to those of skill in the art. For example, covalent immobilization can be accomplished through, for example, silane coupling. See, e.g., Weetall, 15 Adv. Mol. Cell Bio. 161 (2008); Weetall, 44 Meths. Enzymol. 134 (1976). The covalent interaction between the affinity tag and the solid substrate surface can also be mediated by other art-recognized chemical reactions, such as NHS reaction or a conjugation agent. The non-covalent interaction between the affinity tag and the solid substrate surface can be formed based on ionic interactions, van der Waals interactions, dipole-dipole interactions, hydrogen bonds, electrostatic interactions, and/or shape recognition interactions.

In some embodiments, the affinity tag can comprise a linker as described herein. For example, in some embodiments, the affinity tag can comprise a member of a coupling molecule pair as described in the "Linkers" section below. In some embodiments, the affinity tag can comprise a member of the biotin-avidin or biotin-streptavidin coupling pair. For example, in some embodiments, the affinity tag can comprise a biotin molecule, while the solid surface can be coupled with avidin and/or streptavidin.

In some embodiments, the affinity tag can comprise a physical linker. For example, the affinity tag can comprise a magnetic particle, where the affinity tag is immobilized to a solid substrate surface under a magnetic force.

In some embodiments, the capture probes have minimal or no secondary structures such as any stable intra-molecular base-pairing interaction (e.g., hairpins). Without wishing to be bound by theory, the minimal secondary structure in the capture probes can provide for better hybridization between the capture probe's backbone and a portion of the identification nucleotide sequences. In addition, the minimal secondary structure in the capture probes can provide for better attachment of the bound complex (i.e., a complex comprising a capture probe bound to an identification nucleotide sequence) to a solid substrate surface. In some embodiments, the capture probes described herein have no significant intra-molecular pairing at a pre-determined annealing temperature. The pre-determined annealing temperature can range from about 65° C.-80° C. or from about 70° C.-80° C., or at about 70° C.-75° C.

In some embodiments, the capture probe can comprise a second target probe-specific region that binds to a second portion of the identification nucleotide sequence of a target probe. Accordingly, in some embodiments, a capture probe can comprise: (a) a second target probe-specific region that binds to a second portion of the identification nucleotide sequence; and optionally (b) an affinity tag.

As used herein, the term "second target probe-specific region" refers to a region of a capture probe that binds to a second portion of the identification nucleotide sequence of a target probe. The second target probe-specific region can comprise a fairly regularly-spaced pattern of a nucleotide residue and/or a group (e.g., at least 2 or more) of nucleotide residues in the backbone. In some embodiments, a nucleotide residue and/or a group (e.g., at least 2 or more) of nucleotide residues can be spaced at least an average of 1, 2, 3, 4, 5, 6, 7, 8, 9, 10, 11, 12, 13, 4, 15, 20, 25, 30, 35, 40, 45, or 50 bases apart within the second target probe-specific region. This allows for a second target probe-specific region having a regularly spaced pattern of a nucleotide or a group of nucleotides binds to a nucleotide sequence that has a complementary nucleotide or a group of complementary nucleotides regularly spaced apart by about the same number of bases. For example, in some embodiments, when the second target probe-specific region contain a fairly regularly-spaced pattern of adenine residues in the backbone, it can bind a nucleotide sequence that has a thymine residue fairly regularly spaced apart by about the same of number of bases.

In some embodiments, at least 30% or more (including, e.g., at least 40%, at least 50%, at least 60%, at least 70%, at least 80%, at least 90%, at least 95%, at least 97%, at least 99%, or 100%) of the second target probe-specific region is complementary to a second portion of the identification nucleotide sequence.

In some embodiments, the second target probe-specific region can be identified for use in the capture probe using the methods and computer systems described in U.S. Pat. No. 8,415,102 to NanoString Technologies, Inc.

In some embodiments, the second target probe-specific region and an affinity tag can be coupled to each other by at least one or more linkers as described herein. In some embodiments, the linker between the second target probe-specific region and the affinity tag can comprise an amide bond. In some embodiments, the linker between the second target probe-specific region and the affinity tag can comprise a chemical linker as described herein.

In some embodiments, the capture probe(s) described herein refers to a "capture probe" or "unlabeled nanoreporter probe" or "nanoreporter probe(s)" as described in the U.S. Pat. No. 8,519,115; and US Patent App. Pub. Nos. US 2014/0017688; US 2014/0037620; US2013/0017971; US 2013/0230851; US 2011/0201515; US 2011/0086774; US 2011/0229888; and US 2010/0261026, all of which are assigned to Nanostring Technologies, Inc. and are incorporated herein by reference.

Where both reporter probes and capture probes are used in the methods and/or systems described herein, the first target probe-specific region of a reporter probe and the second target probe-specific region of a capture probe should hybridize to a portion of an identification nucleotide sequence at different positions. For example, the portions of the identification nucleotide sequences to which the target-specific regions of the reporter and capture probes hybridize can be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40 or more base pairs apart.

Systems, e.g., for Multiplexed Detection of Target Molecules in a Sample

Various embodiments of the methods described herein can be carried out in one or more functional modules in a system or a computer system as described herein. Accordingly, another provided herein relates to a system for multiplexed detection of a plurality of target molecules in a sample.

FIG. 18A depicts a device or a computer system 600 comprising one or more processors 630 and a memory 650 storing one or more programs 620 for execution by the one or more processors 630.

In some embodiments, the device or computer system 600 can further comprise a non-transitory computer-readable storage medium 700 storing the one or more programs 620 for execution by the one or more processors 630 of the device or computer system 600.

In some embodiments, the device or computer system 600 can further comprise one or more input devices 640, which can be configured to send or receive information to or from any one from the group consisting of: an external device (not shown), the one or more processors 630, the memory 650, the non-transitory computer-readable storage medium 700, and one or more output devices 660.

In some embodiments, the device or computer system 600 can further comprise one or more output devices 660, which can be configured to send or receive information to or from any one from the group consisting of: an external device (not shown), the one or more processors 630, the memory 650, and the non-transitory computer-readable storage medium 700.

In some embodiments, the device or computer system 600 for multiplexed detection of target molecules in a sample comprises: one or more processors; and memory to store one or more programs, the one or more programs comprising instructions for:
(a) receiving said at least one test sample comprising a sample and a plurality of target probes described herein;
(b) releasing the identification nucleotide sequences from the target probes that are bound to target molecules in the sample;
(c) detecting signals from the released identification nucleotide sequences;
(d) determining the presence of one or more target molecules in the sample based on the detected signals by performing the following:
  i. identifying the detectable probes of the reporter probes that correspond to the detected signals;
  ii. identifying the identification nucleotide sequences of the target probes that correspond to the detectable probes based on the first target probe-specific regions of the reporter probes; and
  iii. identifying the target-binding molecules that correspond to the identification nucleotide sequences; and
(e) displaying a content based in part on the analysis output from said analysis module, wherein the content comprises a signal indicative of the following: (i) the presence of one or more target molecules in the sample, (ii) the absence of one or more target molecules in the sample, and/or (iii) expression levels of one or more target molecules in the sample.

FIG. 18B depicts a device or a system 600 (e.g., a computer system) for obtaining data from at least one test sample obtained from at least one subject is provided. The system can be used for multiplexed detection of target molecules in a sample. The system comprises:
(a) at least one sample processing module 601 comprising instructions for
  receiving said at least one test sample comprising a sample and a plurality of target probes described herein; and
  releasing the identification nucleotide sequences from the target probes that are bound to target molecules in the sample;
(b) a signal detection module 602 comprising instructions for detecting signals from the released identification nucleotide sequences;
(c) at least one data storage module 604 comprising instructions for storing the detected signals from (b) and information associated with identification nucleotide sequences of the target probes;

(d) at least one analysis module 606 comprising instructions for determining the presence of one or more target molecules in the sample based on the detected signals; and (e) at least one display module 610 for displaying a content based in part on the analysis output from said analysis module, wherein the content comprises a signal indicative of the following: (i) the presence of one or more target molecules in the sample, (ii) the absence of one or more target molecules in the sample, and/or (iii) expression levels of one or more target molecules in the sample.

In some embodiments, the sample processing module 601 can be adapted for isolating target cells, as single cells or as a population, from the sample. In some embodiments, the sample processing module can comprise a microfluidic device for magnetic separation of target cells or interfering cells from a sample using the methods and devices as described in as described in the International Pat. App. No. WO 2013/078332, the content of which is incorporated herein by reference.

In some embodiments, the sample processing module 601 can comprise a multi-well plate (e.g., 96-well, 384 wells, or nano- or micro-wells) for single-cell analyses.

In some embodiments, the sample processing module 601 can be adapted for extracting nucleic acid molecules from the same sample for nucleic acid analysis. Techniques for nucleic acid analysis are known in the art and can be used to assay the test sample to determine nucleic acid or gene expression measurements, for example, but not limited to, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing), nanopore DNA sequencing, sequencing by hybridization, sequencing with mass spectrometry, microfluidic Sanger sequencing, microscopy-based sequencing techniques, RNA polymerase (RNAP) sequencing, or any combinations thereof.

Accordingly, in some embodiments, the system described herein can be used to generate integrate profiling, e.g., expression profiles of proteins and nucleic acid molecules from the same sample.

In some embodiments, the sample processing module 601 or the signal detection module 602 can further comprise instructions for contacting the released identification nucleotide sequences with reporter probes described herein.

In some embodiments, the sample processing module 601 or the signal detection module 602 can further comprise instructions for contacting the released identification nucleotide sequences with capture probes described herein.

In some embodiments, the sample processing module 601 or the signal detection module 602 can further comprise instructions for immobilizing the released identification nucleotides to a solid substrate through the affinity tag described herein. Examples of a solid substrate include, but are not limited to a microfluidic device, a cartridge, a tube, a microtiter plate, a magnetic particle, and any combinations thereof.

In some embodiments, the analysis module 606 can further comprise instructions for (i) identifying the detectable probes of the reporter probes that correspond to the detected signals; (ii) identifying the identification nucleotide sequences of the target probes that correspond to the detectable probes based on the first target probe-specific regions of the reporter probes; and (iii) identifying the target-binding molecules that correspond to the identification nucleotide sequences, thereby determining the presence of one or more target molecules in the sample based on the detected signals.

In some embodiments, the analysis module 606 can further comprise instructions for identifying a detectable label corresponding for a plurality of light signals emitted from each detectable label, wherein a spatial or temporal order of the plurality of the light signals is unique for each detectable label.

In some embodiments, the analysis module 606 can further comprise instructions for thresholding the detected signals. For example, the signals can be thresholded on the basis of nonspecific binding. In some embodiments, the threshold is greater than that of the signals from the non-specific binding. By way of example only, the threshold can be determined by using standard deviation and measurement error from at least one control protein. In some embodiments, the threshold can be at least 50% or more (including, e.g., at least 60%, at least 70%, at least 80%, at least 90%, at least 95%, or higher) greater than that of the signals from the non-specific binding. In some embodiments, the threshold can be at least 1.1-fold or more (including, e.g., at least 1.2-fold, at least 1.3-fold, at least 1.4-fold, at least 1.5-fold, at least 2-fold, or higher) greater than that of the signals from the non-specific binding.

In some embodiments, the analysis module 606 can further comprise instructions for quantifying the signals by normalizing the signals associated with the target probes by the signals associated with the control probes. In one embodiment, the signals is quantified and expressed as number of identification nucleotide sequences detected per target-binding agent.

Depending on the nature of test samples and/or applications of the systems as desired by users, the display module 610 can further display additional content. In some embodiments where the test sample is collected or derived from a subject for diagnostic assessment, the content displayed on the display module 610 can further comprise a signal indicative of a diagnosis of a condition (e.g., disease or disorder such as cancer)

In some embodiments wherein the test sample is collected or derived from a subject for selection and/or evaluation of a treatment regimen for a subject, the content can further comprise a signal indicative of a treatment regimen personalized to the subject. In some embodiments, the content can further comprise a signal indicative of the treatment response.

A tangible and non-transitory (e.g., no transitory forms of signal transmission) computer readable medium 700 having computer readable instructions recorded thereon to define software modules for implementing a method on a computer is also provided herein. In some embodiments, the computer readable medium 700 stores one or more programs for multiplexed detection of target molecules in a sample. The one or more programs for execution by one or more processors of a computer system comprises (a) instructions for determining the presence of one or more target molecules in the sample based on the detected signals from the released identification nucleotide sequences by performing the following: (i) identifying the detectable probes of the reporter probes that correspond to the detected signals; (ii) identifying the identification nucleotide sequences of the target probes that correspond to the detectable probes based on the first target probe-specific regions of the reporter probes; and (iii) identifying the target-binding molecules that correspond to the identification nucleotide sequences; and (b) instructions for displaying a content based in part on the analysis output from said analysis module, wherein the content comprises a signal indicative of the following: (i) the presence of one or more target molecules in the sample, (ii) the absence of one or more target molecules in the sample, and/or (iii) expression levels of one or more target molecules in the sample.

Depending on the nature of test samples and/or applications of the systems as desired by users, the computer readable storage medium 700 can further comprise instructions for displaying additional content. In some embodiments where the test sample is collected or derived from a subject for diagnostic assessment, the content displayed on the display module can further comprise a signal indicative of a diagnosis of a condition (e.g., disease or disorder) in the subject. In some embodiments wherein the test sample is collected or derived from a subject for selection and/or evaluation of a treatment regimen for a subject, the content can further comprise a signal indicative of a treatment regimen personalized to the subject. In some embodiments, the content can further comprise a signal indicative of the treatment response.

Embodiments of the systems described herein have been described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times. Furthermore, it should be appreciated that the modules may perform other functions, thus the modules are not limited to having any particular functions or set of functions.

Computing devices typically include a variety of media, which can include computer-readable storage media and/or communications media, in which these two terms are used herein differently from one another as follows. Computer-readable storage media or computer readable media (e.g., 700) can be any available tangible media (e.g., tangible storage media) that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM (random access memory), ROM (read only memory), EEPROM (erasable programmable read only memory), flash memory or other memory technology, CD-ROM (compact disc read only memory), DVD (digital versatile disk) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, radio frequency (RF), infrared and other wireless media.

In some embodiments, the computer readable storage media 700 can include the "cloud" system, in which a user can store data on a remote server, and later access the data or perform further analysis of the data from the remote server.

Computer-readable data embodied on one or more computer-readable media, or computer readable medium 700, may define instructions, for example, as part of one or more programs, that, as a result of being executed by a computer, instruct the computer to perform one or more of the functions described herein (e.g., in relation to system 600, or computer readable medium 700), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 600, or computer readable medium 700 described herein, may be distributed across one or more of such components, and may be in transition there between.

The computer-readable media can be transportable such that the instructions stored thereon can be loaded onto any computer resource to implement the assays and/or methods described herein. In addition, it should be appreciated that the instructions stored on the computer readable media, or computer-readable medium 700, described above, are not limited to instructions embodied as part of an application program running on a host computer. Rather, the instructions may be embodied as any type of computer code (e.g., software or microcode) that can be employed to program a computer to implement the assays and/or methods described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the system or computer system described herein can include a sample processing module, a signal detection module, a storage device, an analysis module and a display module. The functional modules can be executed on one, or multiple, computers, or by using one, or multiple, computer networks. The signal detection module 602 can have computer executable instructions to detect signals from the released identification nucleotide sequences.

In some embodiments, the signal detection module 602 can have computer executable instructions to provide sequence information in computer readable form, e.g., for RNA sequencing. In these embodiments, the system can enable simultaneous measurements of target molecules (e.g., proteins) and nucleic acid molecules from the same sample. For example, the integrated expression profiles of the protein and nucleic acid molecules can be used to study proteins that interact with genetic regulatory elements such as microRNAs. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, signal detection modules 602 for determining sequence information may include known systems for automated sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England).

Alternative methods for determining sequence information, i.e. signal detection modules 602, include systems for protein and DNA analysis. For example, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); automated ELISA systems (e.g., DSX® or DS2® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence in situ hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The signals from the released identification nucleotide sequences determined in the signal detection module can be read by the storage device 604. As used herein the "storage device" 604 is intended to include any suitable computing or processing apparatus or other device configured or adapted for storing data or information. Examples of electronic apparatus suitable for use with the system described herein can include stand-alone computing apparatus, data telecommunications networks, including local area networks (LAN), wide area networks (WAN), Internet, Intranet, and Extranet, and local and distributed computer processing systems. Storage devices 604 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 604 is adapted or configured for having recorded thereon sequence information or expression level information. Such information may be provided in digital form that can be transmitted and read electronically, e.g., via the Internet, on diskette, via USB (universal serial bus) or via any other suitable mode of communication, e.g., the "cloud."

As used herein, "expression level information" refers to expression levels of any target molecules to be measured, e.g., but not limited to, proteins, peptides, lipids, metabolites, carbohydrates, toxins, growth factors, hormones, cytokines, cells, and any combinations thereof. In some embodiments, the expression level information can be determined from the detected signals from the released identification nucleotide sequences corresponding to each target molecule.

As used herein, "stored" refers to a process for encoding information on the storage device 604. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information and/or expression level information in computer-readable form, one can use the sequence information and/or expression level information in readable form in the analysis module 606 to generate expression profiles for the sample being tested. The analysis made in computer-readable form provides a computer readable analysis result which can be processed by a variety of means. Content 608 based on the analysis result can be retrieved from the analysis module 606 to indicate the presence or absence of one or more target molecules present in a sample.

The "analysis module" 606 can use a variety of available software programs and formats for calculating expression profiles of various target molecules. In one embodiment, the analysis module 606 can calculate proteomic expression profiles as follows. First, raw counts of the released identification nucleotide sequences can be first normalized by using the nSolver analysis software to account for hybridization differences on a cartridge, before normalization via the mean of the internal positive controls, which account for hybridization efficiency. These counts can then be converted to expression values using the relative counts of identification nucleotide sequences per a target-binding agent (e.g., an antibody). Next, average background signal from control IgG can be subtracted. Housekeeping genes can then be used for normalization that accounted for cell number variations. Signals can then be normalized via a housekeeping protein, e.g., GAPDH, actin, and/or β-tubulin.

In some embodiments, the analysis module 606 can comprise, e.g., MATLAB or functionally equivalent thereof to generate heat maps and clustergrams with a matrix input of marker expression values that were calculated as described above. In some embodiments, the clustergrams can be performed as a weighted linkage. In some embodiments, the clustergrams can be clustered using correlation values as a distance metric. If a target molecule was not detectable, it can be removed from the matrix or heat map and is not displayed.

In some embodiments, the analysis module 606 can comprise one or more programs for analyzing reporter probes and/or capture probes as described in U.S. Pat. No. 7,941,279 to NanoString Technologies, Inc.

In some embodiments, the analysis module 606 can compare protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Protein chip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

The analysis module 606, or any other module of the system described herein, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular embodiment, users can directly access data (via Hypertext links for example) residing on Internet databases using a HTML interface provided by Web browsers and Web servers. In another embodiment, users can directly access data residing on the "cloud" provided by the cloud computing service providers.

The analysis module 606 provides computer readable analysis result that can be processed in computer readable form by predefined criteria, or criteria defined by a user, to provide a content based in part on the analysis result that may be stored and output as requested by a user using a display module 610. The display module 610 enables display of a content 608 based in part on the comparison result for the user, wherein the content 608 is a signal indicative of the presence of one or more target molecules in the sample, a signal indicative of the absence of one or more target molecules in the sample, a signal indicative of expression levels of one or more target molecules in the sample, or any combinations thereof. Such signal, can be for example, a display of content 608 on a computer monitor, a printed page of content 608 from a printer, or a light or sound indicative of the absence of a target molecule in a sample.

In various embodiments of the computer system described herein, the analysis module 606 can be integrated into the signal detection module 602.

Depending on the nature of test samples and/or applications of the systems as desired by users, the content 608 based on the analysis result can also include a signal indicative of a diagnosis of a condition (e.g., disease or disorder) in the subject. In some embodiments, the content 608 based on the analysis result can further comprise a signal indicative of a treatment regimen personalized to the subject. In some embodiments, the content 608 based on the analysis result can further comprise a signal indicative of a response of a subject to a treatment, which provides a means of monitoring the treatment response in a subject.

In some embodiments, the content 608 based on the analysis result can include a graphical representation reflecting the expression profiles of target molecules, e.g., as shown in FIG. 5.

In one embodiment, the content 608 based on the analysis result is displayed a on a computer monitor. In one embodiment, the content 608 based on the analysis result is displayed through printable media. The display module 610 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In some embodiments, the content can be displayed on a computer display, a screen, a monitor, an email, a text message, a website, a physical printout (e.g., paper), or provided as stored information in a data storage device.

In one embodiment, a World Wide Web browser is used for providing a user interface for display of the content 608 based on the analysis result. It should be understood that other modules of the system described herein can be adapted to have a web browser interface. Through the Web browser, a user may construct requests for retrieving data from the analysis module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the expression profile of target molecules in a sample, e.g., display of an indication of the presence or absence of one or more target molecules in the sample, or display of information based thereon. In one embodiment, the information of the control reference is also displayed.

In any embodiments, the analysis module can be executed by a computer implemented software as discussed earlier. In such embodiments, a result from the analysis module can be displayed on an electronic display. The result can be displayed by graphs, numbers, characters or words. In additional embodiments, the results from the analysis module can be transmitted from one location to at least one other location. For example, the comparison results can be transmitted via any electronic media, e.g., internet, fax, phone, a "cloud" system, and any combinations thereof. Using the "cloud" system, users can store and access personal files and data or perform further analysis on a remote server rather than physically carrying around a storage medium such as a DVD or thumb drive.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

The system 600, and computer readable medium 700, are merely illustrative embodiments, e.g., for multiplexed detection of target molecules in a sample and/or for use in the methods of various aspects described herein and is not intended to limit the scope of the inventions described herein. Variations of system 600, and computer readable medium 700, are possible and are intended to fall within the scope of the inventions described herein.

The modules of the machine, or used in the computer readable medium, may assume numerous configurations. For example, function may be provided on a single machine or distributed over multiple machines.

Kits, e.g., for Multiplexed Detection of Target Molecules in a Sample

Kits, e.g., for multiplexed detection of different target molecules from a sample, are also provided herein. In some embodiments, the kit comprises (a) a plurality of target probes in accordance with one or more embodiments described herein; and (b) a plurality of reporter probes in accordance with one or more embodiments described herein.

In some embodiments, each subset of the target probes in the plurality binds to a different target molecule, wherein the target probes in the subset comprise the same target-binding molecule. That is, no two target probes in the subset binds to different regions of the same target molecule.

In some embodiments, the kit comprises at least 3 or more (including at least 4, at least 5, at least 10, at least 15, at least 20, at least 30, at least 40, at least 50, at least 60, at least 70, at least 80, at least 90, at least 100, at least 150, at least 200, at least 250 or more) different target probes described herein, wherein each target probe specifically binds to a different target molecule. Accordingly, in some embodiments, the kit further comprises at least 3 or more (including at least 4, at least 5, at least 10, at least 15, at least 20, at least 30, at least 40, at least 50, at least 60, at least 70, at least 80, at least 90, at least 100, at least 150, at least 200, at least 250 or more) different reporter probes, wherein each reporter probe identifies a distinct target probe.

In some embodiments, depending on the design of the identification nucleotide sequences of the target probes, the kit can further comprise at least one or more (including at least 4, at least 5, at least 10, at least 15, at least 20, at least 30, at least 40, at least 50, at least 60, at least 70, at least 80, at least 90, at least 100, at least 150, at least 200, at least 250 or more) capture probes described herein. In some embodiments, the same capture probe can be used, e.g., for immobilization of different identification nucleotide sequences to a solid substrate surface for visualization and/or imaging. In some embodiments, different capture probes can be used, e.g., for immobilization of different identification nucleotide sequences to a solid substrate surface for visualization and/or imaging.

In some embodiments, reporter probes and capture probes can be provided in the kit individually or in a mixture.

In some embodiments, the target-binding molecules of the target probes can comprise antibodies or fragments thereof. In some embodiments, the antibodies or fragments thereof can be selected from Table 1.

In some embodiments, the cleavable linker of the target probes can comprise a photocleavable linker. In some embodiments, the photocleavable linker can be selected from the molecules (i)-(xiv) as shown earlier. In some embodiments, the photocleavable linker can comprise molecule (xiv).

In some embodiments, the detectable label of the reporter probes can comprise one or more labeling molecules that create a unique signal for each reporter probe. An exemplary unique signal can be an optical signal. The optical signal can comprise one or a series or a sequence of light-emitting signals. In these embodiments, non-limiting examples of the labeling molecules include fluorochrome moieties, fluorescent moieties, dye moieties, chemiluminescent moieties, and any combinations thereof.

In some embodiments, the kit can further comprise a plurality of (e.g., at least 2 or more, including, at least 3, at least 4, at least 5, at least 6, at least 7 or more) control probes in accordance with one or more embodiments described herein.

In some embodiments, the kit can further comprise reagents for detecting a plurality of nucleic acid molecules. Example reagents for nucleic acid detection and analysis can include, but are not limited to, nucleic acid polymerase, primers, nucleotides, an agent for nucleic acid extraction, a buffered solution, control nucleic acid sequences, and any combination thereof. Such kit can be used to generate an integrated profiling that combines both target molecule (e.g., protein) and genetic material information (e.g., DNA, RNA, epigenetic, and microRNAs). Thus, the kit can be used to study target molecules that interact with genetic materials such as genetic regulatory elements.

In some embodiments, the kit can further comprise at least one reagent for use in one or more embodiments of the methods or systems described herein. Reagents that can be provided in the kit can include at least one or more of the following: a hybridization reagent, a purification reagent, an immobilization reagent, an imaging agent, a cell permeabilization agent, a blocking agent, a cleaving agent for the cleavable linker, and any combinations thereof.

In some embodiments, the kit can further include at least one or more devices (e.g., sample cartridges or microfluidic devices) or tubes for use in one or more embodiments of the methods and/or systems described herein. In some embodiments, the device can comprise a surface for immobilization of the capture probes upon coupling to the identification nucleotide sequences. In some embodiments, the device can comprise a microfluidic device for separating target cells from interfering cells as described herein. For example, a microfluidic device for magnetic separation of target cells or interfering cells from a sample as described in the International Pat. App. No. WO 2013/078332, the content of which are incorporated herein by reference, can be included in the kit.

In some embodiments, the kit can further include a computer-readable (non-transitory) storage medium in accordance with one or more embodiments described herein. For example, in one embodiment, the computer-readable (non-transitory) storage medium included in the kit can provide instructions to determine the presence or expression levels of one or more target molecules in a sample. The computer-readable (non-transitory) storage medium can be in a CD, DVD, and/or USB drive.

In all such embodiments of the aspect, the kit includes the necessary packaging materials and informational material therein to store and use said kits. The informational material can be descriptive, instructional, marketing or other material that relates to the methods described herein and/or the use of an agent(s) described herein for the methods described herein. In one embodiment, the informational material can include instructions to perform a multiplexed detection of target molecules in a sample. In one embodiment, the information material can include instructions to analyze the signal readouts.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In all embodiments of the aspects described herein, the kit will typically be provided with its various elements included in one package, e.g., a fiber-based, e.g., a cardboard, or polymeric, e.g., a styrofoam box. The enclosure can be configured so as to maintain a temperature differential between the interior and the exterior, e.g., it can provide insulating properties to keep the reagents at a preselected temperature for a preselected time. The kit can include one or more containers for the composition containing a compound(s) described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit usage forms of target probes described herein. For example, the kit includes a plurality of syringes, ampules, foil packets, or blister packs, each containing a single unit usage of target probes described herein. The containers of the kits can be air tight, waterproof (e.g., impermeable to changes in moisture or evaporation), and/or light-tight.

Exemplary Uses of the Methods, Systems and Kits Described Herein

The methods, systems and kits described herein can be used in any applications where detection of a plurality of target molecules in a sample is desirable. For example, a sample can be a biological sample, or a sample from an environmental source (e.g., water, soil, food products, and/or ponds). Other samples that can be analyzed with the methods, systems, and kits described herein are discussed in the "Sample" section below.

The inventors have demonstrated that, in one embodiment, an antibody barcoding with photocleavable DNA (ABCD) platform described herein can enable analysis of hundreds of proteins from a single cell or a limited number of cells, e.g., from minimally invasive fine-needle aspirates (FNAs). Accordingly, samples amenable to the methods described herein can comprise less than 500 cells or fewer. In some embodiments, the sample can comprise less than 400 cells, less than 300 cells, less than 200 cells, less than 100 cells, less than 50 cells, less than 25 cells, less than 5 cells or fewer. In some embodiments, the sample can be a single-cell sample. In some embodiments, the sample can comprise cells isolated from a fine-needle aspirate.

Where the sample is a biological sample, in some aspects, the methods, systems and kits described herein can be used in personalized treatment. For example, a biological sample can be collected from an individual subject who is in need of a treatment for a condition. Using the methods, systems and/or kits described herein, an expression profile of target molecules associated with the subject's condition can be generated to identify one or more therapeutic targets for the subject, thereby identifying a treatment regimen for the subject. Accordingly, methods for identifying a treatment regimen for an individual subject are also provided herein. In this aspect, the method comprises: (i) contacting a sample derived from a subject who is in need of a treatment for a condition, with a composition comprising a plurality of target probes that bind to target molecules associated with the condition; (ii) releasing the identification nucleotide sequences from the bound target probes; (iii) detecting signals from the released identification nucleotide sequences, wherein the signals are distinguishable for the identification nucleotide sequences, thereby identifying the corresponding target-binding molecules and determining the presence of one or more target molecules in the sample; and (iv) generating an expression profile of the target molecules detected by the target probes, thereby selecting a treatment regimen for the individual subject based on the expression profile. The methods can be applied to any condition described in the later section. In some embodiments, the condition is cancer. In some embodiments, the signals from the released identification nucleotide sequences are not detected by gel electrophoresis-based methods.

In some aspects, the methods, systems and kits described herein can be used to assess how drug dosing corresponds to cellular pharmacodynamics and thus used in monitoring response of a subject to a treatment for his/her condition. For example, biological sample(s) can be collected from the subject prior to and/or over the course of the treatment. Using the methods, systems and/or kits described herein, expression profiles of target molecules associated with the subject's condition before and/or over the course of the treatment can be generated for comparison to determine any changes in expression levels of the target molecules in the subject, thereby monitoring the treatment response in the subject. Accordingly, another aspect provided herein relates to a method of monitoring a treatment for a condition in a subject. The method comprises: (i) contacting a sample derived from a subject after a treatment for a condition, with a composition comprising a plurality of target probes that bind to target molecules associated with the condition; (ii) releasing the identification nucleotide sequences from the bound target probes; (iii) detecting signals from the released identification nucleotide sequences, wherein the signals are distinguishable for the released identification nucleotide sequences, thereby identifying the corresponding target-binding molecules and determining the presence of one or more target molecules in the sample; (iv) generating an expression profile of the target molecules detected by the target probes; (v) comparing the expression profile with an expression profile generated from a sample derived from the same subject prior to the treatment or after treatment at an earlier time point; and (vi) determining changes in expression levels of the target molecules, thereby monitoring the treatment for the condition in the subject. In some embodiments, the signals from the released identification nucleotide sequences are not detected by gel electrophoresis-based methods.

In some embodiments, the method can further comprise administering an alternative treatment for the condition, when there are no substantial changes in expression levels of the target molecules or the changes in expression levels of the target molecules do not represent a reduction in symptoms associated with the condition.

In some embodiments, the method can further comprise continuing the same treatment for the condition, when the changes in expression levels of the target molecules represent a reduction in symptoms associated with the condition.

In some aspects, the methods, systems and kits described herein can be used in diagnosing a condition in a subject. For example, a biological sample can be collected from a subject who is at risk for a condition. Using the methods, systems and/or kits described herein, an expression profile of target molecules associated with the condition to be diagnosed can be generated for comparison with one or more reference expression profiles (e.g., corresponding to a normal healthy subject and/or a subject having the condition to be diagnosed), thereby determining whether the subject is at risk for the condition. Accordingly, provided here is also a method for diagnosing a condition in a subject. The method comprises: (i) contacting a sample derived from a subject who is at risk for a condition, with a composition comprising a plurality of target probes that bind to target molecules associated with the condition; (ii) releasing the identification nucleotide sequences from the bound target probes; (iii) detecting signals from the released identification nucleotide sequences, wherein the signals are distinguishable for the identification nucleotide sequences, thereby identifying the corresponding target-binding molecules and determining the presence of one or more target molecules in the sample; (iv) generating an expression profile of the target molecules detected by the target probes, (v) comparing the expression profile to at least one reference expression profile, thereby determining whether the subject is at risk for the condition. In some embodiments, the signals from the released identification nucleotide sequences are not detected by gel electrophoresis-based methods.

In some embodiments, a reference expression profile is associated with the condition. In some embodiments, a reference expression profile is associated with a normal healthy subject.

In some embodiments, the methods described herein can be used to determine intratumoral heterogeneity, which can be used as a biomarker for diagnosis and/or prognosis.

Conditions (e.g., Diseases or Disorders) Amenable to Diagnosis, Prognosis/Monitoring, and/or Treatment Using Methods, Systems, Kits, or Various Aspects Described Herein Different embodiments of the methods, systems and/or kits described herein can be used for diagnosis and/or treatment of a disease or disorder in a subject, e.g., a condition afflicting a certain tissue in a subject. For example, the disease or disorder in a subject can be associated with breast, pancreas, blood, prostate, colon, lung, skin, brain, ovary, kidney, oral cavity, throat, cerebrospinal fluid, liver, or other tissues, and any combination thereof.

In some embodiments, the condition (e.g., disease or disorder) amenable to diagnosis and/or treatment using any aspects described herein can include a breast disease or disorder. Exemplary breast disease or disorder includes breast cancer.

In some embodiments, the condition (e.g., disease or disorder) amenable to diagnosis and/or treatment using any aspects described herein can include a pancreatic disease or disorder. Nonlimiting examples of pancreatic diseases or disorders include acute pancreatitis, chronic pancreatitis, hereditary pancreatitis, pancreatic cancer (e.g., endocrine or exocrine tumors), etc., and any combinations thereof.

In some embodiments, the condition (e.g., disease or disorder) amenable to diagnosis and/or treatment using any aspects described herein can include a blood disease or disorder. Examples of blood disease or disorder include, but are not limited to, platelet disorders, von Willebrand diseases, deep vein thrombosis, pulmonary embolism, sickle cell anemia, thalassemia, anemia, aplastic anemia, fanconi anemia, hemochromatosis, hemolytic anemia, hemophilia, idiopathic thrombocytopenic purpura, iron deficiency anemia, pernicious anemia, polycythemia vera, thrombocythemia and thrombocytosis, thrombocytopenia, and any combinations thereof.

In some embodiments, the condition (e.g., disease or disorder) amenable to diagnosis and/or treatment using any aspects described herein can include a prostate disease or disorder. Non-limiting examples of a prostate disease or disorder can include prostatis, prostatic hyperplasia, prostate cancer, and any combinations thereof.

In some embodiments, the condition (e.g., disease or disorder) amenable to diagnosis and/or treatment using any aspects described herein can include a colon disease or disorder. Exemplary colon diseases or disorders can include, but are not limited to, colorectal cancer, colonic polyps, ulcerative colitis, diverticulitis, and any combinations thereof.

In some embodiments, the condition (e.g., disease or disorder) amenable to diagnosis and/or treatment using any aspects described herein can include a lung disease or disorder. Examples of lung diseases or disorders can include, but are not limited to, asthma, chronic obstructive pulmonary disease, infections, e.g., influenza, pneumonia and tuberculosis, and lung cancer.

In some embodiments, the condition (e.g., disease or disorder) amenable to diagnosis and/or treatment using any aspects described herein can include a skin disease or disorder, or a skin condition. An exemplary skin disease or disorder can include skin cancer.

In some embodiments, the condition (e.g., disease or disorder) amenable to diagnosis and/or treatment using any aspects described herein can include a brain or mental disease or disorder (or neural disease or disorder). Examples of brain diseases or disorders (or neural disease or disorder) can include, but are not limited to, brain infections (e.g., meningitis, encephalitis, brain abscess), brain tumor, glioblastoma, stroke, ischemic stroke, multiple sclerosis (MS), vasculitis, and neurodegenerative disorders (e.g., Parkinson's disease, Huntington's disease, Pick's disease, amyotrophic lateral sclerosis (ALS), dementia, and Alzheimer's disease), Timothy syndrome, Rett syndrome, Fragile X, autism, schizophrenia, spinal muscular atrophy, frontotemporal dementia, any combinations thereof.

In some embodiments, the condition (e.g., disease or disorder) amenable to diagnosis and/or treatment using any aspects described herein can include a liver disease or disorder. Examples of liver diseases or disorders can include, but are not limited to, hepatitis, cirrhosis, liver cancer, biliary cirrhosis, fatty liver, nonalcoholic steatohepatitis (NASH), fibrosis, primary sclerosing cholangitis, Budd-Chiari syndrome, hemochromatosis, transthyretin-related hereditary amyloidosis, Gilbert's syndrome, and any combinations thereof.

In other embodiments, the condition (e.g., disease or disorder) amenable to diagnosis and/or treatment using any aspects described herein can include cancer. A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include, but are not limited to carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the methods and systems described herein can be used for determining in a subject a given stage of cancer, e.g., based on the expression profiling generated using the methods described herein. The stage of a cancer generally describes the extent the cancer has progressed and/or spread. The stage usually takes into account the size of a tumor, how deeply the tumor has penetrated, whether the tumor has invaded adjacent organs, how many lymph nodes the tumor has metastasized to (if any), and whether the tumor has spread to distant organs. Staging of cancer is generally used to assess prognosis of cancer as a predictor of survival, and cancer treatment is primarily determined by staging.

Sample

In accordance with various embodiments described herein, a sample, including any fluid or specimen (processed or unprocessed) or other biological sample, can be subjected to the methods of various aspects described herein.

In some embodiments, the sample can include a biological fluid obtained from a subject. Exemplary biological fluids obtained from a subject can include, but are not limited to, blood (including whole blood, plasma, cord blood and serum), lactation products (e.g., milk), amniotic fluids (e.g., a sample collected during amniocentesis), sputum, saliva, urine, peritoneal fluid, pleural fluid, semen, cerebrospinal fluid, bronchial aspirate, perspiration, mucus, liquefied feces or stool samples, synovial fluid, lymphatic fluid, tears, tracheal aspirate, and fractions thereof. In some embodiments, a biological fluid can include a homogenate of a tissue specimen (e.g., biopsy) from a subject. In one embodiment, a test sample can comprises a suspension obtained from homogenization of a solid sample obtained from a solid organ or a fragment thereof. In some embodiments, a sample can be obtained from a mucosal swab. In some embodiments, a sample can be obtained from a tissue biopsy (e.g. but not limited to skin biopsy). In some embodiments, a sample can be a fine needle aspirate.

In some embodiments, a sample can be obtained from a subject who has or is suspected of having a disease or disorder. In some embodiments, the sample can be obtained from a subject who has or is suspected of having cancer, or who is suspected of having a risk of developing cancer.

In some embodiments, a sample can be obtained from a subject who is being treated for a disease or disorder. In other embodiments, the sample can be obtained from a subject whose previously-treated disease or disorder is in remission. In other embodiments, the test sample can be obtained from a subject who has a recurrence of a previously-treated disease or disorder. For example, in the case of cancer such as breast cancer, a test sample can be obtained from a subject who is undergoing a cancer treatment, or whose cancer was treated and is in remission, or who has cancer recurrence.

As used herein, a "subject" can mean a human or an animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, and avian species, e.g., chicken, emu, ostrich. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. The term "patient" and "subject" does not denote a particular age. Thus, any mammalian subjects from adult to newborn subjects, as well as fetuses, are intended to be covered.

In one embodiment, the subject or patient is a mammal. The mammal can be a human, non-human primate, mouse, rat, dog, cat, horse, or cow, but are not limited to these examples. In one embodiment, the subject is a human being. In another embodiment, the subject can be a domesticated animal and/or pet.

In some embodiments, a sample that can be analyzed by the methods, systems and kits described herein can be obtained from an environmental source. Examples of an environmental source include, but are not limited to, water, soil, food products, ponds, reservoir, and any combinations thereof.

Linkers

As used herein, the term "linker" generally refers to a molecular entity that can directly or indirectly connect at two parts of a composition. For example, in some embodiments with respect to a reporter probe, the linker directly or indirectly connects a first target probe-specific region to a detectable label described herein. In some embodiments with respect to a capture probe, the linker directly or indirectly connects a second target probe-specific region to an affinity tag described herein. In some embodiments with respect to a target probe, the linker directly or indirectly connects an identification nucleotide sequence to a target-binding molecule. In some embodiments with respect to a control probe, the linker directly or indirectly connects an identification control sequence to a control-binding molecule.

In some embodiments, a linker can comprise a peptide or nucleic acid linker. The peptide or nucleic acid linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp), or nucleic acid sequences encoding the amino acids thereof can also be included in a linker sequence. In alternative embodiments, polar amino acids or nucleic acid sequence thereof can be added to modulate the flexibility of a linker. One of skill in the art can control flexibility of a linker by varying the types and numbers of residues in the linker. See, e.g., Perham, 30 Biochem. 8501 (1991); Wriggers et al., 80 Biopolymers 736 (2005).

In alternative embodiments, a linker can comprise a chemical linker of any length. In some embodiments, chemical linkers can comprise a direct bond or an atom such as oxygen or sulfur, a unit such as NH, C(O), C(O)NH, SO, $SO_2$, $SO_2NH$, or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, $C(O)N(R^1)_2$, C(O), cleavable linker, substituted or unsubstituted aryl, substituted or unsubstituted heteroaryl, substituted or unsubstituted heterocyclic; where $R^1$ is hydrogen, acyl, aliphatic or substituted aliphatic. In some embodiments, the chemical linker can be a polymer chain (branched or linear).

In some embodiments, the chemical linker can comprise a stable or labile (e.g., cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/adamantly host guest interaction) and the like.

As used herein, the term "conjugation agent" means an organic moiety that connects two parts of a compound. Without limitations, any conjugation chemistry known in the art for conjugating two molecules or different parts of a composition together can be used for coupling two parts of a compound. Exemplary coupling molecules and/or functional groups for coupling two parts of a compound include, but are not limited to, a polyethylene glycol (PEG, NH2-PEGX—COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, hydrolyzable conjugation agent, and any combinations thereof.

In some embodiments, the linker includes a coupling molecule pair. The terms "coupling molecule pair" and "coupling pair" as used interchangeably herein refer to the first and second molecules that specifically bind to each other. One member of the coupling pair is conjugated to a first entity while the second member is conjugated to a second entity, which is desired to be connected to the first entity. By way of example only, the first entity can be a detectable label of a reporter probe described herein, and the second entity can be a first target probe-specific region of the reporter probe. Thus, the detectable label can be coupled to the first target probe-specific region via a coupling molecule pair. As another example, a solid substrate surface can comprise a first member of the coupling pair, while an affinity tag of a capture probe described here can comprise a second member of the coupling pair. As used herein, the phrase "first and second molecules that specifically bind to each other" refers to binding of the first member of the coupling pair to the second member of the coupling pair with greater affinity and specificity than to other molecules.

Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, a first entity is biotinylated (i.e., the first entity comprise a biotin molecule) and a second entity desired to be connected to the first entity can comprise an avidin or streptavidin. Many commercial kits are also available for biotinylating molecules, such as proteins. For example, an aminooxy-biotin (AOB) can be used to covalently attach biotin to a molecule with an aldehyde or ketone group.

Still another example of using coupling pair conjugation is double-stranded nucleic acid conjugation. In this approach, a first entity can comprise a first strand of the double-stranded nucleic acid and a second entity desired to be connected to the first entity can comprise a second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

In some embodiments, a linker can be a physical substrate, e.g., microparticles or magnetic particles.

The linkers can be of any shape. In some embodiments, the linkers can be linear. In some embodiments, the linkers can be folded. In some embodiments, the linkers can be branched. In other embodiments, the linker adopts the shape of the physical substrate.

In some embodiments, the linker can comprise a cleavable linker described herein.

Embodiments of Various Aspects Described Herein can be Defined in any of the Following Numbered Paragraphs:
1. A method for detecting a plurality of target molecules in a sample comprising:
    a. contacting a sample with a composition comprising a plurality of target probes, wherein each target probe in the plurality comprises:
        i. a target-binding molecule that specifically binds to a distinct target molecule in the sample;
        ii. an identification nucleotide sequence that identifies the target-binding molecule; and
        iii. a cleavable linker between the target-binding molecule and the identification nucleotide sequence;
    b. separating unbound target probes from a plurality of complexes in the sample, each complex having a target molecule and a single target probe bound thereto, wherein the complex does not have a second target probe binding to a different region of the target molecule;
    c. releasing the identification nucleotide sequences from the plurality of complexes;
    d. detecting signals from the released identification nucleotide sequences based on a non-gel electrophoresis method, wherein the signals are distinguishable for the identification nucleotide sequences, thereby identifying the corresponding target-binding molecules and detecting a plurality of different target molecules in the sample.
2. The method of paragraph 1, wherein the non-gel electrophoresis method comprises sequencing, quantitative polymerase chain reaction (PCR), multiplexed (PCR), mass cytometry, fluorophore-inactivated multiplexed immunofluorescence, hybridization-based methods, fluorescence hybridization-based methods, or any combinations thereof.
3. The method of paragraph 1 or 2, further comprising, prior to the detecting step (d), coupling the released identification nucleotide sequences from the releasing step (c) to a detection composition comprising a plurality of reporter probes, wherein each reporter probe in the plurality comprises: a first target probe-specific region that is capable of binding a first portion of the identification nucleotide sequence; and a detectable label that identifies the reporter probe.
4. The method of paragraph 3, wherein the detecting comprises detecting signals from the respective detectable labels of the reporter probes that are coupled to the released identification nucleotide sequences, wherein the signals are distinguishable for the respective reporter probes and bound the identification nucleotide sequences, thereby identifying the corresponding target-binding molecules and detecting a plurality of target molecules in the sample.
5. The method of paragraph 3 or 4, wherein the detection composition further comprises a plurality of capture probes, wherein each capture probe comprises (i) a second target probe-specific region that is capable of binding a second portion of the identification nucleotide sequence; and (ii) an affinity tag.
6. The method of paragraph 5, wherein the affinity tag of the capture probe permits immobilization of the released identification nucleotide sequences onto a solid substrate, upon coupling to the detection composition.
7. The method of any of paragraphs 3-6, wherein the detectable label of the reporter probes comprises one or more labeling molecules that create a unique signal for each reporter probe.

8. The method of paragraph 7, wherein the unique signal is an optical signal.
9. The method of paragraph 8, wherein the optical signal comprises a sequence of light-emitting signals.
10. The method of any of paragraphs 7-9, wherein the one or more labeling molecules are selected from the group consisting of a fluorochrome moiety, a fluorescent moiety, a dye moiety, a chemiluminescent moiety, and any combinations thereof.
11. The method of any of paragraphs 1-10, wherein the detecting step (d) comprises no amplification of the released identification nucleotide sequences.
12. The method of any of paragraphs 3-11, wherein the detecting step (d) comprises no amplification of the first target probe-specific region, or the second target probe-specific region.
13. The method of any of paragraphs 1-12, wherein the identification nucleotide sequences are selected such that they do not cross-react with a human genome.
14. The method of paragraph 13, wherein the identification nucleotide sequences are derived from a potato genome.
15. The method of any of paragraphs 1-14, wherein the identification nucleotide sequences have a length of about 30-100 nucleotides.
16. The method of any of paragraphs 1-15, wherein the identification nucleotide sequences have a length of about 70 nucleotides.
17. The method of paragraph 16, wherein the identification nucleotide sequences have a sequence selected from Table 2 (SEQ ID NO: 1 to SEQ ID NO: 110).
18. The method of any of paragraphs 1-17, wherein the cleavable linker is a cleavable, non-hybridizable linker.
19. The method of paragraph 18, wherein the cleavable, non-hybridizable linker is sensitive to an enzyme, pH, temperature, light, shear stress, sonication, a chemical agent (e.g., dithiothreitol), or any combination thereof.
20. The method of paragraph 18 or 19, wherein the cleavable, non-hybridizable linkers are selected from the group consisting of hydrolyzable linkers, redox cleavable linkers, phosphate-based cleavable linkers, acid cleavable linkers, ester-based cleavable linkers, peptide-based cleavable linkers, photocleavable linkers, and any combinations thereof.
21. The method of any of paragraphs 18-20, wherein the cleavable, non-hybridizable linker comprises a disulfide bond, a tetrazine-trans-cyclooctene group, a sulfhydryl group, a nitrobenzyl group, a nitoindoline group, a bromo hydroxycoumarin group, a bromo hydroxyquinoline group, a hydroxyphenacyl group, a dimethozybenzoin group, or any combinations thereof.
22. The method of any of paragraphs 18-21, wherein the cleavable, non-hybridizable linker comprises a photocleavable linker.
23. The method of paragraph 22, wherein the photocleavable linker is selected from the group consisting of molecules (i)-(xiv) and any combinations thereof, wherein the chemical structures of the molecules (i)-(xiv) are shown as follows:

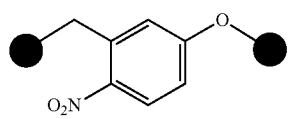

(i)

-continued

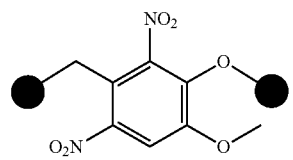

(ii)

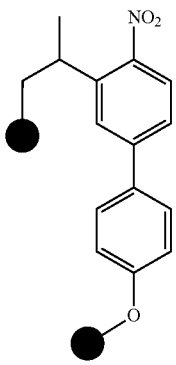

(iii)

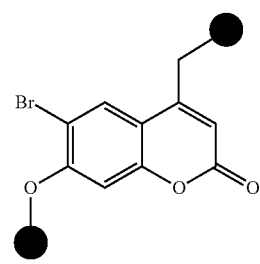

(iv)

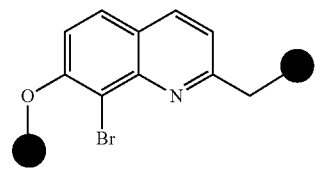

(v)

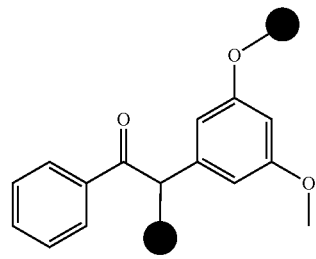

(vi)

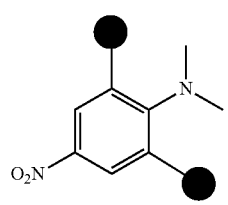

(vii)

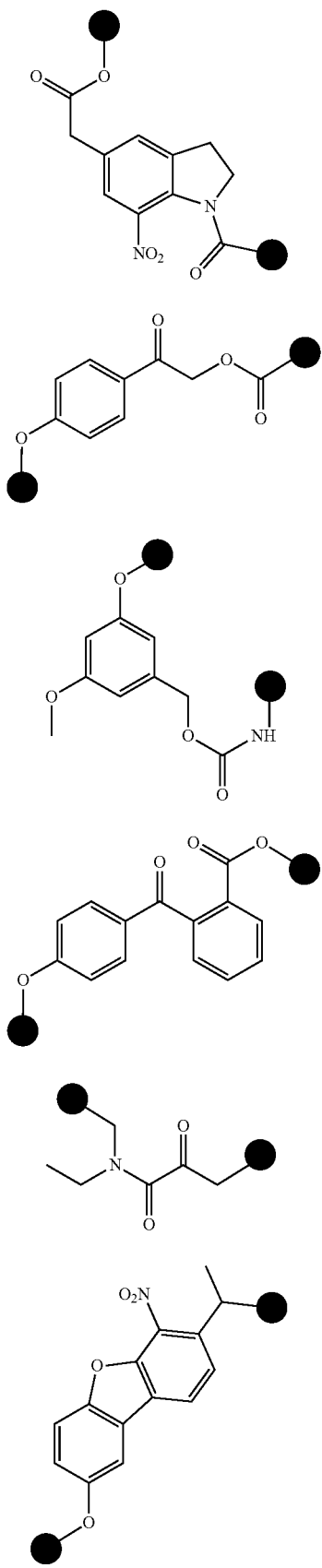
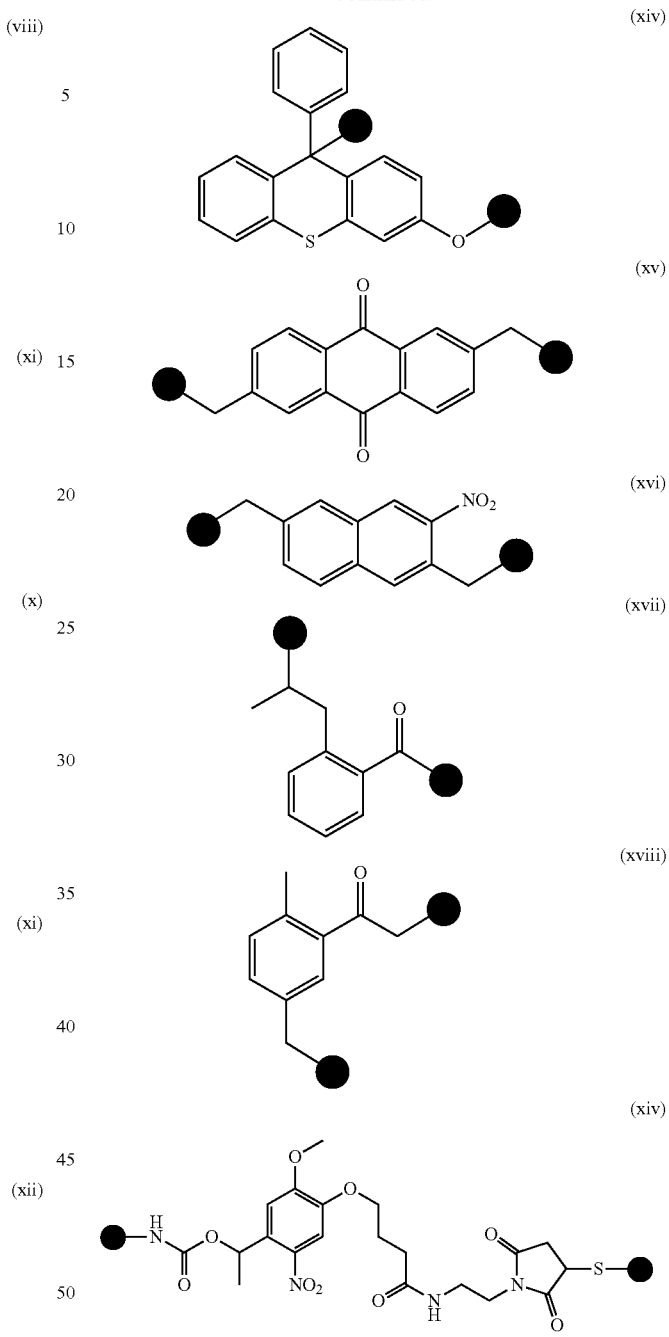

wherein each of the black dots in each molecule represents a connecting or coupling point that connects, directly or indirectly, to the target-binding molecule or the identification nucleotide sequence.

24. The method of paragraph 22, wherein the photocleavable linker comprises the molecule (xiv).

25. The method of any of paragraphs 22-24, wherein the releasing of the identification nucleotide sequences from the bound target probes comprises exposing the bound target probes to ultraviolet light.

26. The method of any of paragraphs 1-25, wherein the sample comprises less than 500 cells.

27. The method of any of paragraphs 1-26, wherein the sample is a single-cell sample.

28. The method of any of paragraphs 1-27, wherein the sample comprises cells isolated from a fine-needle aspirate.
29. The method of any of paragraphs 1-28, further comprising, prior to the contacting, separating target cells from interfering cells in the sample.
30. The method of paragraph 29, wherein the separating comprises labeling the interfering cells or target cells with magnetic particles and separating them from the sample by magnetic separation.
31. The method of paragraph 30, wherein the magnetic separation is performed in a microfluidic device.
32. The method of any of paragraphs 29-31, wherein the target cells comprise rare cells.
33. The method of paragraph 32, wherein the rare cells are selected from the group consisting of circulating tumor cells, fetal cells, stem cells, immune cells, clonal cells, and any combination thereof.
34. The method of any of paragraphs 29-33, wherein the target cells comprise tumor cells from a liquid biopsy (e.g., peritoneal, pleural, cerebrospinal fluid, and/or blood), a mucosal swap, a skin biopsy, a stool sample, or any combinations thereof.
35. The method of any of paragraphs 1-34, wherein the target molecules comprise proteins, peptides, metabolites, lipids, carbohydrates, toxins, growth factors, hormones, cytokines, cells, and any combinations thereof.
36. The method of any of paragraphs 1-35, further comprising permeabilizing the target cells in the sample.
37. The method of any of paragraphs 1-36, wherein the composition further comprises a plurality of control probes, wherein each control probe in the plurality comprises:
   i. a control-binding molecule that specifically binds to one control molecule in the sample;
   ii. an identification control sequence that identifies the control-binding molecule; and
   iii. a cleavable linker between the control-binding molecule and the identification control sequence.
38. The method of paragraph 37, wherein the control-binding molecule binds to a control protein.
39. The method of paragraph 38, wherein the control protein is selected from the group consisting of housekeeping proteins, control IgG isotypes, mutant non-functional or non-binding proteins, and any combinations thereof.
40. The method of any of paragraphs 1-39, further comprising thresholding the signals.
41. The method of paragraph 40, wherein the signals are thresholded on the basis of nonspecific binding.
42. The method of paragraph 41, wherein the threshold is greater than that of the signals from the non-specific binding.
43. The method of any of paragraphs 40-42, wherein the threshold is determined by using standard deviation and measurement error from at least one control protein.
44. The method of any of paragraphs 1-43, further comprising quantifying the signals by normalizing the signals associated with the target probes by the signals associated with the control probes.
45. The method of any of paragraphs 1-44, further comprising extracting a nucleic acid molecule from the same sample for nucleic acid analysis.
46. The method of paragraph 45, further comprising subjecting the nucleic acid molecule to a nucleic acid analysis.
47. The method of paragraph 46, wherein the nucleic acid analysis comprises sequencing, quantitative polymerase chain reaction (PCR), multiplexed PCR, DNA sequencing, RNA sequencing, de novo sequencing, next-generation sequencing such as massively parallel signature sequencing (MPSS), polony sequencing, pyrosequencing, Illumina (Solexa) sequencing, SOLiD sequencing, ion semiconductor sequencing, DNA nanoball sequencing, Heliscope single molecule sequencing, single molecule real time (SMRT) sequencing, nanopore DNA sequencing, sequencing by hybridization, sequencing with mass spectrometry, microfluidic Sanger sequencing, microscopy-based sequencing techniques, RNA polymerase (RNAP) sequencing, or any combinations thereof.
48. The method of any of paragraphs 45-47, wherein the target molecules to be detected in the sample comprise proteins, thereby detecting proteins and nucleic acid molecules from the same sample.
49. A kit for multiplexed detection of a plurality of different target molecules from a sample comprising:
   a. a plurality of target probes, wherein each target probe in the plurality comprises:
      i. a target-binding molecule that specifically binds to a distinct target molecule in the sample;
      ii. an identification nucleotide sequence that identifies the target-binding molecule; and
      iii. a cleavable, non-hybridizable linker between the target-binding molecule and the identification nucleotide sequence;
   b. a plurality of reporter probes, wherein each reporter probe comprises:
      i. a first target probe-specific region that is capable of binding a first portion of the identification nucleotide sequence; and
      ii. a detectable label that identifies the reporter probe.
50. The kit of paragraph 49, further comprising a plurality of capture probes, wherein each capture probe comprises (i) a second target probe-specific region that is capable of binding a second portion of the identification nucleotide sequence; and (ii) an affinity tag.
51. The kit of paragraph 49 or 50, wherein the detectable label of the reporter probes comprises one or more labeling molecules that create a unique signal for each reporter probe.
52. The kit of paragraph 51, wherein the unique signal is an optical signal.
53. The kit of paragraph 52, wherein the optical signal comprises a sequence of light-emitting signals.
54. The kit of any of paragraphs 51-53, wherein the one or more labeling molecules are selected from the group consisting of a fluorochrome moiety, a fluorescent moiety, a dye moiety, a chemiluminescent moiety, and any combinations thereof.
55. The kit of any of paragraphs 49-54, wherein the target-binding molecule comprises proteins, peptides, metabolites, lipids, carbohydrates, toxins, growth factors, hormones, cytokines, cells, and any combination thereof.
56. The kit of any of paragraphs 49-55, wherein the cleavable, non-hybridizable linker is sensitive to an enzyme, pH, temperature, light, shear stress, sonication, a chemical agent (e.g., dithiothreitol), or any combination thereof.
57. The kit of any of paragraphs 49-56, wherein the cleavable, non-hybridizable linkers are selected from the group consisting of hydrolyzable linkers, redox cleavable linkers, phosphate-based cleavable linkers, acid cleavable linkers, ester-based cleavable linkers, peptide-based cleavable linkers, photocleavable linkers, and any combinations thereof.

58. The kit of any of paragraphs 49-57, wherein the cleavable, non-hybridizable linker comprises a disulfide bond, a tetrazine-trans-cyclooctene group, a sulfhydryl group, a nitrobenzyl group, a nitoindoline group, a bromo hydroxycoumarin group, a bromo hydroxyquinoline group, a hydroxyphenacyl group, a dimethozybenzoin group, or any combinations thereof.

59. The kit of any of paragraphs 49-58, wherein the cleavable, non-hybridizable linker comprises a photocleavable linker.

60. The kit of paragraph 59, wherein the photocleavable linker is selected from the group consisting of molecules (i)-(xiv) and any combinations thereof, wherein the chemical structures of the molecules (i)-(xiv) are shown as follows:

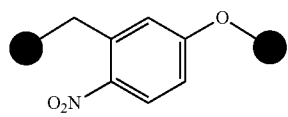
(i)

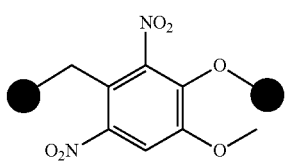
(ii)

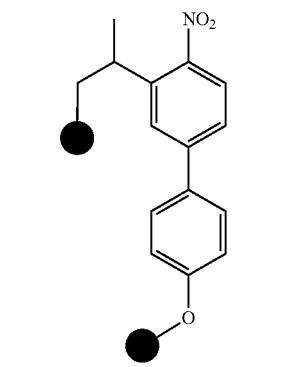
(iii)

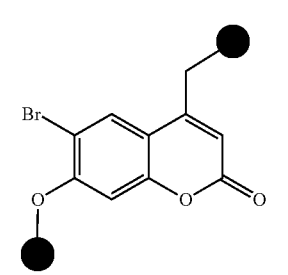
(iv)

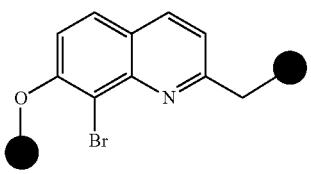
(v)

-continued

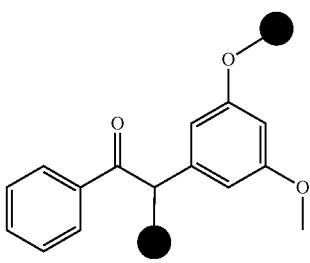
(vi)

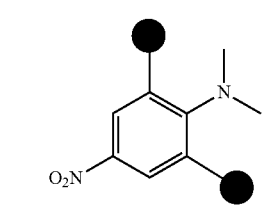
(vii)

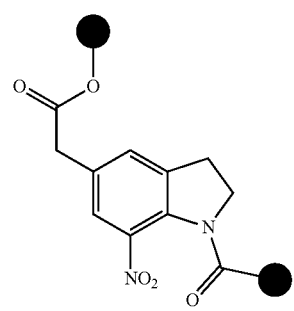
(viii)

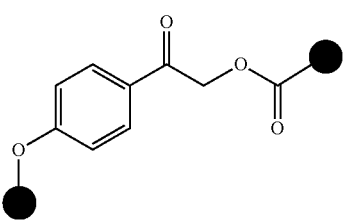
(xi)

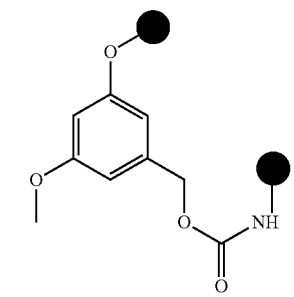
(x)

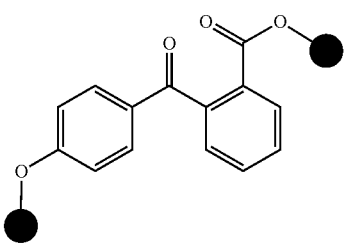
(xi)

-continued (xii)

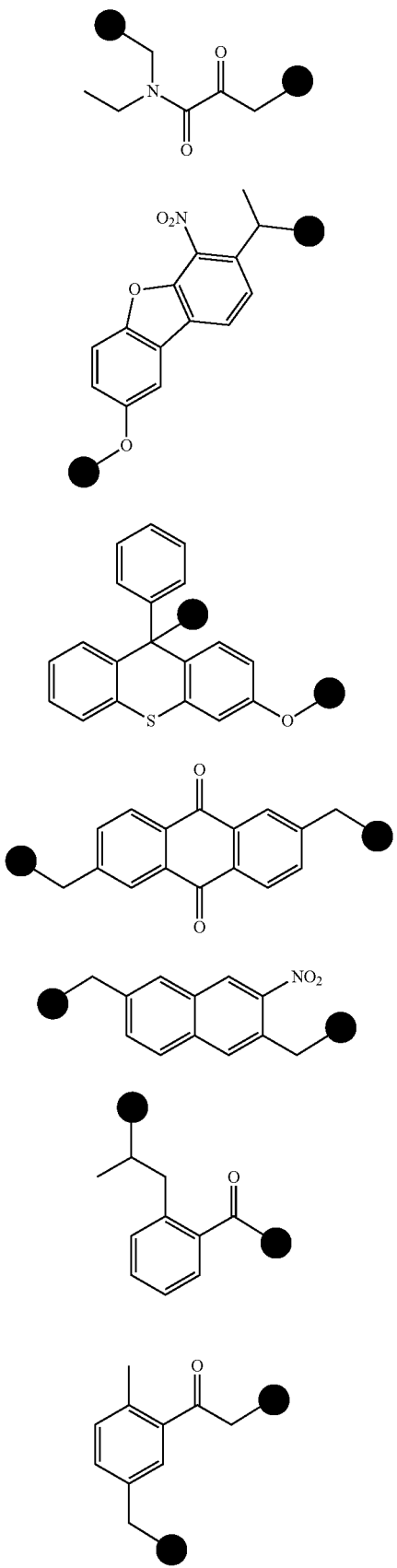

(xiii)

(xiv)

(xv)

(xvi)

(xvii)

(xviii)

-continued (xiv)

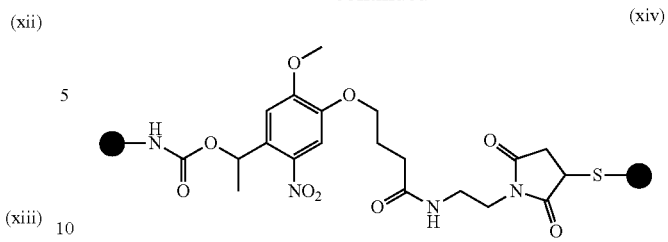

wherein each of the black dots in each molecule represents a connecting or coupling point that connects, directly or indirectly, to the target-binding molecule or the identification nucleotide sequence.

61. The kit of paragraph 59, wherein the photocleavable linker comprises the molecule (xiv).

62. The kit of any of paragraphs 49-61, further comprising a plurality of control probes, wherein each control probe in the plurality comprises:
   i. a control-binding molecule that specifically binds to one control molecule in the sample;
   ii. an identification control sequence that identifies the control-binding molecule; and
   iii. a cleavable linker between the control-binding molecule and the identification control sequence.

63. The kit of paragraph 62, wherein the control-binding molecule binds to a control protein.

64. The kit of paragraph 63, wherein the control protein is selected from the group consisting of housekeeping proteins, control IgG isotypes, mutant non-functional or non-binding proteins, and any combinations thereof.

65. The kit of any of paragraphs 49-64, further comprising a reagent selected from the group consisting of a hybridization reagent, a purification reagent, an immobilization reagent, an imaging agent, a cell permeabilization agent, a blocking agent, a cleaving agent for the cleavable linker, and any combinations thereof.

66. The kit of any of paragraphs 49-65, further comprising a device, wherein the device comprises a surface for immobilization of the capture probes upon coupling to the identification nucleotide sequences.

Some Selected Definitions

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" with respect to numerical values means within 5%.

As used herein, the term "comprising" or "comprise(s)" is used in reference to compositions, methods, and respective component(s) thereof, that are essential to the invention, yet open to the inclusion of unspecified elements, whether essential or not.

As used herein, the term "consisting essentially of" or "consist(s) essentially of" refers to those elements required for a given embodiment. The term permits the presence of additional elements that do not materially affect the basic and novel or functional characteristic(s) of that embodiment of the invention.

As used herein, the term "consisting of" or "consist(s) of" refers to compositions, methods, and respective components thereof as described herein, which are exclusive of any element not recited in that description of the embodiment.

The term "multiplexed detection" refers to detection of a plurality of target molecules from a single sample in a single assay. In some embodiments, multiplexed detection refers to simultaneous measurements of at least 2, at least 3, at least 4, at least 5, at least 10, at least 20, at least 30, at least 40, at least 50, at least 60, at least 70, at least 80, at least 90, at least 100, at least 150, at least 200, at least 250, at least 300, at least 350, at least 400, at least 450, at least 500 or more different target molecules from a single sample.

As used herein, the term "fixed cell or tissue sample" refers to a sample obtained from a cell or tissue which has been previously fixed in a cell- or tissue-fixing solution and optionally afterwards embedded in a solid substrate. Various cell- or tissue-fixing solutions are known in the art, including, but not limited to aldehydes (e.g., but not limited to formaldehyde, formalin), alcohols (e.g., but not limited to, ethanol, methanol, and/or acetone), oxidizing agents (e.g., but not limited to, osmium tetroxide, potassium dichromate, chromic acid, and/or potassium permanganate), picrates, mercurial (e.g., but not limited to, B-5 and/or Zenker's fixative), Hepes-glutamic acid buffer-mediated Organic solvent Protection Effect (HOPE) fixative. In some embodiments, a fixed cell or tissue sample also encompasses a frozen cell or tissue sample.

As used herein, the term "alien or foreign DNA barcode" refers to a DNA sequence used as a barcode or tag for identification of a target molecule in a sample of an organism, wherein the DNA sequence is an alien or foreign sequence relative to the genomes of the organism from which the sample is derived or obtained. As used herein, the term "alien or foreign" refers to a nucleotide sequence that shows no or little homology against an organism (from which a sample is derived or obtained) and/or other major organisms, e.g., in the NCBI Reference Sequence (RefSeq) database. In some embodiments, a nucleotide sequence is alien or foreign when it shares a homology (sequence identity) with that of the organism by no more than 50% or less, including, e.g., no more than 40%, no more than 30%, no more than 20%, no more than 10% or less. In some embodiments, the identification nucleotide sequences described herein are alien or foreign DNA barcodes.

The term "antibody" as used herein refers to a full length antibody or immunoglobulin, IgG, IgM, IgA, IgD or IgE molecules, or a protein portion thereof that comprises only a portion of an intact antibody, generally including an antigen binding site of the intact antibody and thus retaining the ability to bind a target, such as an epitope or antigen. Examples of portions of antibodies or epitope-binding proteins encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C terminus of the CH1 domain; (v) the Fv fragment having the VL and VH domains of a single arm of an antibody; (vi) the dAb fragment (Ward et al., 341 Nature 544 (1989)) which consists of a VH domain or a VL domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) "linear antibodies" comprising a pair of tandem Fd segments (VH-CH1-VH-CH1) which, together with complementary light chain polypeptides, form a pair of antigen binding regions (Zapata et al., 8 Protein Eng. 1057 (1995); and U.S. Pat. No. 5,641,870).

"Antibodies" include antigen-binding portions of antibodies such as epitope- or antigen-binding peptides, paratopes, functional CDRs; recombinant antibodies; chimeric antibodies; tribodies; midibodies; or antigen-binding derivatives, analogs, variants, portions, or fragments thereof.

The term "aptamer" refers to a nucleic acid molecule that is capable of binding to a target molecule, such as a polypeptide. For example, an aptamer of the invention can specifically bind to a target molecule, or to a molecule in a signaling pathway that modulates the expression and/or activity of a target molecule. The generation and therapeutic use of aptamers are well established in the art. See, e.g., U.S. Pat. No. 5,475,096.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

EXAMPLES

Example 1. Optimization for Methods for Multiplex Detection of Target Molecules from a Sample Evaluation of different cleavable linkers: In various embodiments described herein, target-binding molecules can be conjugated to identification nucleotide sequences via any cleavable linker(s) known in the art. In this Example, three alternative methods of conjugating target molecules (e.g., antibodies) to identification nucleotide sequences (e.g., DNA) via a cleavable linker were evaluated using exemplary procedures detailed below.

In the first method, target-binding molecules (e.g., antibodies) were modified with (E)-Cyclooct-4-enyl 2,5-dioxopyrro-lidin-1-yl carbonate (trans-cyclooctene N-hydroxysuccinimidyl ester; TCO-NHS) and synthesized as previously reported in Ref. 26. If present, sodium azide was removed using a 2 ml Zeba desalting column (7 K MWCO). The reaction was performed using 1000 molar equivalents of TCO-NHS in PBS containing 10% (v/v) DMF and 10 mM sodium bicarbonate for 4 h at RT. At the same time, a photocleavable Tz-NHS was reacted with an amine group on the 5' end of the 70mer DNA strand (15 molar excess) for 4 h at RT. After the reactions concluded, the target-binding molecule-TCO (e.g., Ab-TCO) conjugate was purified using a Zeba column (7000 MWCO), and the DNA-Tz conjugate was purified using a 3 K MWCO Amicon filter followed by three washes with PBS. Next, the target-binding molecule-TCO (e.g., Ab-TCO) and Tz-DNA were combined via click chemistry (26) for two hours at RT. The final target probe (e.g., antibody-DNA conjugate) was purified by size separation using Amicon 100 K MWCO filters followed by washes with PBS.

Figure 2B:
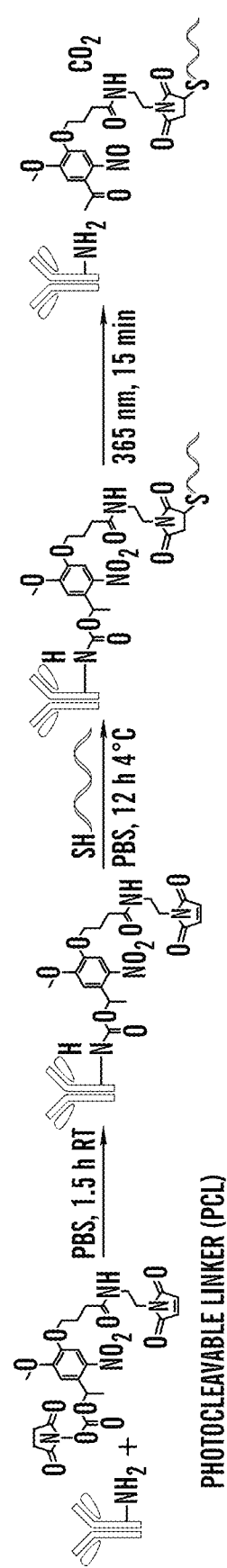

In the second method, the photocleavable bifunctional linker (FIG. 2) reacted (10 molar excess) with the amine group on the 5' end of the 70mer single-stranded DNA (IDT) for 4 h at RT. Three hours after the DNA reaction began, the target-binding molecules (e.g., antibody) was reacted with 2-iminothiolane (Traut's reagent, 10 molar excess, Thermo Scientific) to convert amine groups to sulfydryl (—SH) groups in PBS with 2 mM EDTA for 1 h at RT. When the reactions concluded, the thiolated target-binding molecules (e.g., antibody) was separated from excess Traut's Reagent using a Zeba desalting column (7000 MWCO) that had been equilibrated with PBS containing 2 mM EDTA. The excess photocleavable (PC) bifunctional linker was purified from the DNA with a 3 K MWCO Amcion filter. Then the target-binding molecule-SH (e.g., antibody-SH) and the DNA-PC-linker (~15 molar excess) were reacted overnight at 4° C. The final target probe (e.g., antibody-DNA conjugate) was purified by size separation using Amicon 100 K MWCO filters followed by washes with PBS.

In the third method, an amine to sulfhydryl linker, sulfo-succinimidyl 6-[3'(2-pyridyldithio)-propionamido] hexanoate (sulfo-LC-SPDP, Thermo Scientific), was reacted with a target-binding molecule (e.g., antibody) in PBS-EDTA at 50 molar excess and aged for 1 h at RT. At the end of the reaction, excess sulfo-LC-SPDP was removed using a Zeba desalting column (7000 MWCO). The thiolyated DNA was reduced with DTT and purified via a NAP-5 column, as previously described in the DNA-antibody conjugation in the "Exemplary materials and methods" section below. Once excess sulfo-LC-SPDP was purified using a Zeba column, the target-binding molecule (e.g., antibody) was reacted with the reduced thiolyated DNA (~15 molar excess) overnight at 4° C. The final target probe (e.g., antibody-DNA conjugate) was purified by size separation using Amicon 100 K MWCO filters followed by washes with PBS.

The three UV-cleavable target-binding molecule-DNA (e.g., Ab-DNA) linker methods were compared by first labeling A431 cells with EGFR and EPCAM DNA conjugates and then determining which method resulted in the highest signal to noise ratio (SNR), e.g., via Nanostring. The conjugation of target molecules (e.g., antibodies) with the bifunctional photocleavable linker described in FIG. 2A gave the highest SNR. This target probe (e.g., antibody-conjugate) was then compared to the target probe (e.g., antibody-DNA conjugate containing the DTT cleavable disulfide bond. SKOV3 cells ($5 \times 10^5$ cells) were labeled with Herceptin-DNA conjugates (1 μg). After 30 minutes the cells were spun down at 400×g for 3 minutes, and the excess Herceptin was removed with two SB+washes. The Herceptin-DNA conjugate with the disulfide linker was then cleaved by adding DTT (50 mM) for 15 minutes at 37° C. At the same time, the Herceptin-DNA conjugate with the photocleavable linker was exposed to UV light (wavelength) for 15 minutes. After the 15-minute cleavage step, the cells were spun down at 400×g for 5 minutes, and the supernatant was removed. The DNA in the supernatant was measured using the single-stranded Qubit assay to determine the amount of DNA cleaved from the antibody. The UV photocleavable linker had 2.4-fold more DNA than the disulfide linker.

Figure 3:
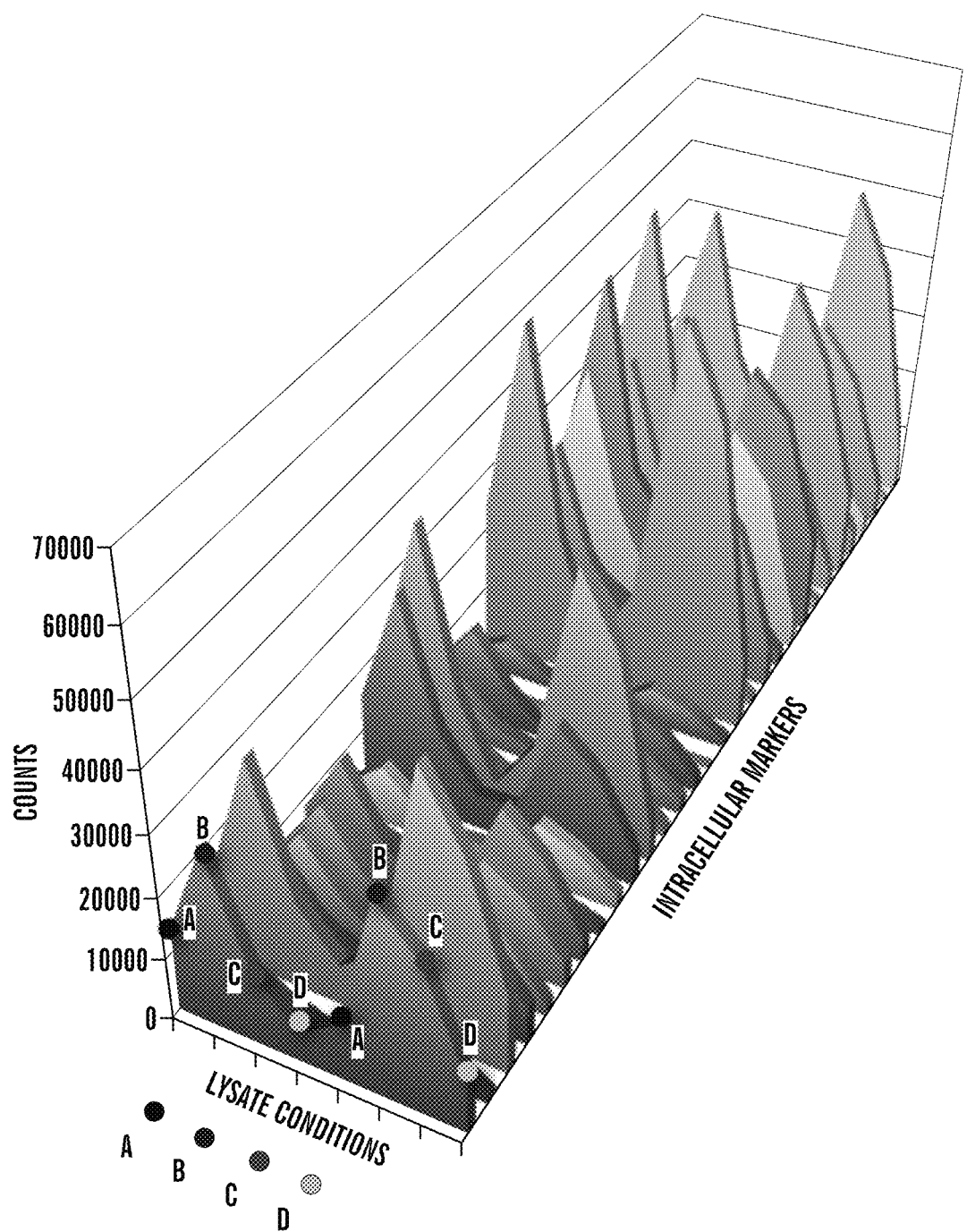
FIG. 3 shows experimental data directed to optimization of lysis and blocking methods. (Methods A to D) Four different lysis and blocking methods were used to recover DNA from labeled cells. Lysate conditions included: (Method A) Proteinase K+PKD lysis buffer; (Method B) Proteinase K+ATL lysis buffer; (Method C) ATL lysis buffer alone; and (Method D) UV cleavage alone (no cell lysis).

Optimization of lysis conditions: Four different lysis conditions were evaluated to determine which was the most efficient (FIG. 3): (A) Proteinase K with buffer PKD (Qiagen) and UV; (B) Proteinase K with buffer ATL (Qiagen) and UV; (C) ATL buffer with UV; and (D) UV. Based on the tested methods, method (B) showed a 20% increase in signal over methods (A) and (C).

Example 2. Development and Validation of Methods for Multiplex Detection of Target Molecules from a Sample In this Example, an antibody barcoding with photocleavable DNA (ABCD) platform was designed to perform multiplexed protein measurements and system-wide profiling on small amounts of clinical sample material (e.g., ~100 cells). The method was designed to preserve genetic material and to enable specific isolation of rare single cells. This approach interrogates single cells by tagging antibodies of interest with short (~70-mer) DNA "barcodes"—with each antibody having a unique sequence-using a stable photocleavable linker. Photocleavable linkers known in the art (e.g., Ref. 9) can be used herein. After antibody binding to the cells, the photocleavable linker releases the unique DNA barcode, which can then be detected by various means. In some embodiments, different DNA barcodes can be identified based on size using gel electrophoresis. However, this method had limited multiplexing (8 to 12 markers) and was only semiquantitative (9). Other quantitative methods, such as sequencing and quantitative polymerase chain reaction (qPCR), are reliable and can be used to detect the released DNA barcodes, but may introduce bias during amplification steps, require prolonged processing time, or are not cost-effective. Multiplexed qPCR only measures a maximum of five markers at a time. Thus, a fluorescence hybridization technology, which have been traditionally used for multiplexed quantitation (16,384 barcodes) of femtomolar amounts of DNA and RNA (10, 11), was selected to detect the released DNA barcodes. While the fluorescence hybridization technology has been used to quantify DNA and RNA, it had not been previously extended to measure proteins within cells or clinical samples. This Example and subsequent Examples show application and validation of the ABCD platform in cell lines and human clinical specimens, as well as evaluating drug treatment response and inter- and intrapatient heterogeneity in lung cancer.

Cells were first harvested from fine-needle aspirates (FNAs) from a given patient (FIG. 1A). To better isolate cancer cells from their heterogeneous cellular milieu, aspirates were labeled with antibodies directed against established markers (for example, CD45 to deplete tumor-infiltrating leukocytes from the sample). The antibody was tagged with magnetic nanoparticles and passed through a microfluidic device containing a self-assembled magnetic layer to deplete tagged cells [12]. The purified cancer cell population was retrieved from the device and stained with a mixture comprising a plurality of one or more embodiments of target probes as described herein. In this Example, the purified cancer cell population were stained with a mixture of target probes each containing an antibody and a unique barcode attached via a photocleavable linker (referred to as "antibody conjugate" or "antibody-DNA conjugate" herein) (FIG. 1B and FIG. 2). Example antibodies for use in the antibody conjugates are listed in Table 1 below. In this Example, more than 90 antibodies in the cocktail were chosen and used to demonstrate that bulk labeling yielded similar results to single antibody labeling. The 90 antibody-DNA conjugates were specially designed to tag an alien DNA sequence that would not cross-react with the human genome. Target markers were selected to cover hallmark pathways in cancer (e.g., apoptosis, epigenetic, and DNA damage), cancer diagnostic markers known in the art, e.g., those commonly used in the clinic, and housekeeping and control proteins. Before labeling, antibody-DNA conjugates were isolated via immunoglobulin G (IgG)-specific pull-down and pooled together into a cocktail. After cell blocking, permeabilization and labeling, and washing, the DNA was released from the cells of interest with both proteolytic cleavage and photocleavage to increase yield and, by extension, sensitivity (FIG. 1C).

TABLE 1

List of example antibodies.

| Antibody | Species | Catalog | Vendor |
| --- | --- | --- | --- |
| GAPDH (14C10) | Rabbit | 2118BF | Cell Signaling |
| β-Tubulin (9F3) | Rabbit | 2128BF | Cell Signaling |
| Ku80 (C48E7) | Rabbit | 2180BF | Cell Signaling |
| Phospho-Chk2 (Thr68) (C13C1) | Rabbit | 2197BF | Cell Signaling |
| S6 ribosomal protein (54D2) | Mouse | 2317BF | Cell Signaling |
| Phospho-Chk1 (Ser345) (133D3) | Rabbit | 2348BF | Cell Signaling |
| VE-cadherin (D87F2) | Rabbit | 2500BF | Cell Signaling |
| p53 (7F5) | Rabbit | 2527BF | Cell Signaling |
| Phospho-53BP1 (Ser1778) | Rabbit | 2675BF | Cell Signaling |
| Phospho-(Ser/Thr) ATM/ATR Substrate | Rabbit | 2851BF | Cell Signaling |
| Phospho-4E-BP1 (Thr37/46) (236B4) | Rabbit | 2855BF | Cell Signaling |
| Bim (C34C5) | Rabbit | 2933BF | Cell Signaling |
| Cyclin D3 (DCS22 | Mouse | 2936BF | Cell Signaling |
| Cyclin D1 (92G2) | Rabbit | 2978BF | Cell Signaling |
| mTOR (7C10) | Rabbit | 2983BF | Cell Signaling |
| Phospho-cyclin D1 (Thr286) (D29B3) | Rabbit | 3300BF | Cell Signaling |
| Phospho-histone H3 (Ser10) (D2C8) | Rabbit | 3377BF | Cell Signaling |
| ALK (D5F3) | Rabbit | 3633BF | Cell Signaling |
| Phospho-EGF Receptor (Tyr1068) (D7A5) | Rabbit | 3777BF | Cell Signaling |
| Phospho-Akt (Ser473) (D9E) | Rabbit | 4060BF | Cell Signaling |
| CDCP1 Antibody | Rabbit | 4115BF | Cell Signaling |
| Cyclin E1 (HE12) | Mouse | 4129BF | Cell Signaling |
| Phospho-cyclin E1 (Thr62) | Rabbit | 4136BF | Cell Signaling |
| Phospho-p44/42 MAPK (Erk1/2) (Thr202/Tyr204) (D13.14.4E) | Rabbit | 4370BF | Cell Signaling |
| Keratin 7 (D1E4) | Rabbit | 4465BF | Cell Signaling |
| Histone H3 (D1H2) | Rabbit | 4499BF | Cell Signaling |
| Phospho-p38 MAPK (Thr180/Tyr182) (D3F9) | Rabbit | 4511BF | Cell Signaling |
| Phospho-SEK1/MKK4 (Ser257) (C36C11) | Rabbit | 4514BF | Cell Signaling |
| Pan-keratin (C11 | Mouse | 4545BF | Cell Signaling |
| Keratin 8/18 (C51) | Mouse | 4546BF | Cell Signaling |
| Keratin 18 (DC10) | Mouse | 4548BF | Cell Signaling |
| Akt (pan) (C67E7) | Rabbit | 4691BF | Cell Signaling |
| p44/42 MAPK (Erk1/2) (137F5 | Rabbit | 4695BF | Cell Signaling |
| COX IV (3E11 | Rabbit | 4850BF | Cell Signaling |
| Phospho-S6 ribosomal protein (Ser235/236) | Rabbit | 4858BF | Cell Signaling |
| 53BP1 | Rabbit | 4937BF | Cell Signaling |
| β-Actin (13E5) | Rabbit | 4970BF | Cell Signaling |
| Akt2 (L79B2) | Mouse | 5239BF | Cell Signaling |
| Phospho-mTOR (Ser2448) (D9C2) | Rabbit | 5536BF | Cell Signaling |
| Cleaved PARP (Asp214) (D64E10) | Rabbit | 5625BF | Cell Signaling |
| Vimentin (D21H3) | Rabbit | 5741BF | Cell Signaling |
| Cleaved caspase-9 (Asp330) (D2D4) | Rabbit | 7237BF | Cell Signaling |
| Met (D1C2) | Rabbit | 8198BF | Cell Signaling |
| FGF receptor 4 (D3B12) | Rabbit | 8562BF | Cell Signaling |
| Axl (C89E7) | Rabbit | 8661BF | Cell Signaling |
| p38 MAPK (D13E1) | Rabbit | 8690BF | Cell Signaling |
| BRCA1 (D54A8) | Rabbit | 9025BF | Cell Signaling |
| Phospho-Stat3 (Tyr705) (D3A7) | Rabbit | 9145BF | Cell Signaling |
| Cleaved caspase-7 (Asp198) | Rabbit | 9491BF | Cell Signaling |
| Cleaved caspase-8 (Asp391) (18C8) | Rabbit | 9496BF | Cell Signaling |
| Cleaved caspase-9 (Asp315) | Rabbit | 9505BF | Cell Signaling |
| PARP (46D11) | Rabbit | 9532BF | Cell Signaling |
| 4E-BP1 (53H11) | Rabbit | 9644BF | Cell Signaling |
| Cleaved caspase-3 (Asp175) | Rabbit | 9661BF | Cell Signaling |
| Phospho-histone H2A.X (Ser139) (20E3) | Rabbit | 9718BF | Cell Signaling |
| FGF receptor 1 (D8E4) | Rabbit | 9740BF | Cell Signaling |
| Caspase-8 (1C12) | Mouse | 9746BF | Cell Signaling |
| Caspase-9 | Rabbit | 9502 BF | Cell Signaling |
| Phospho-β-Catenin (Ser675) (D2F1) | Rabbit | 4176BF | Cell Signaling |

TABLE 1-continued

List of example antibodies.

| Antibody | Species | Catalog | Vendor |
|---|---|---|---|
| Phospho-GSK-3β (Ser9) (D85E12) | Rabbit | 5558BF | Cell Signaling |
| Dimethyl-Histone H3 (Lys9) (D85B4) | Rabbit | 4658BF | Cell Signaling |
| Dimethyl-Histone H3 (Lys4) (C64G9) | Rabbit | 9725BF | Cell Signaling |
| Dimethyl-Histone H3 (Lys36) (C75H12) | Rabbit | 2901BF | Cell Signaling |
| Dimethyl-Histone H3 (Lys27) | Rabbit | 9755BF | Cell Signaling |
| Dimethyl-Histone H3 (Lys79) | Rabbit | 9757BF | Cell Signaling |
| Acetyl-histone H3 (Lys9) (C5B11) | Rabbit | 9649BF | Cell Signaling |
| Acetyl-histone H3 (Lys14) | Rabbit | 4318BF | Cell Signaling |
| Acetyl-histone H3 (Lys27) | Rabbit | 4353BF | Cell Signaling |
| Acetyl-histone H3 (Lys56) | Rabbit | 4243BF | Cell Signaling |
| Acetyl-histone H3 (Lys18) | Rabbit | 9675BF | Cell Signaling |
| LC3A (D50G8) | Rabbit | 4599BF | Cell Signaling |
| LC3B (D11) | Rabbit | 3868BF | Cell Signaling |
| p21wafl/cip1 | Rabbit | 2947BF | Cell Signaling |
| Beclin-1 (D40C5) | Rabbit | 3495BF | Cell Signaling |
| β-Catenin (6B3) | Rabbit | 9582BF | Cell Signaling |
| Slug (C19G7) | Rabbit | 9585BF | Cell Signaling |
| Snail (C15D3) | Rabbit | 3897BF | Cell Signaling |
| TCF8/ZEB1 (D80D3) | Rabbit | 3396BF | Cell Signaling |
| c-Myc (D84C12) | Rabbit | 5605BF | Cell Signaling |
| Met (D1C2) | Rabbit | 8198BF | Cell Signaling |
| Phospho-Src family (Tyr416) | Rabbit | 6943BF | Cell Signaling |
| Phospho-Jak2 (Tyr1007) | Rabbit | 4406BF | Cell Signaling |
| Phospho-Jak3 (Tyr980/981) | Rabbit | 5031BF | Cell Signaling |
| Phospho-PLCγ1 (Tyr783) | Rabbit | 2821BF | Cell Signaling |
| Bcl-2 (D55G8) | Rabbit | 4223BF | Cell Signaling |
| Bcl-xL (54H6) rabbit mAb #2764 | Rabbit | 2764BF | Cell Signaling |
| Control mouse IgG1 | Mouse | 400102 | Biolegend |
| Control mouse IgG2a | Mouse | 400202 | Biolegend |
| Control mouse IgG2b | Mouse | 401202 | Biolegend |
| Control rabbit | Rabbit | 550875 | BD Bioscience |
| Control rat IgG2b | Rat | 553986 | BD Bioscience |
| Her2 | Human/Mouse | Herceptin | Genentech |
| EGFR | Human/Mouse | Cetuximab | Bristol-Meyers |
| EpCAM | Mouse | MAB9601 | R&D |
| MUC1 | Mouse | M01102909 | Fitzgerald |
| MUC16 | Mouse | ab1107 | abcam |
| EpHA2 | Mouse | MAB3035 | R&D |
| FOLR1 | Mouse | MAB5646 | R&D |
| FSHR | Mouse | GTX71451 | Genetex |
| TSPAN8 | Mouse | MAB4734 | R&D |
| Claudin-3 | Mouse | MAB4620 | R&D |
| Transferin | Mouse | MAB2474 | R&D |
| CD44s | Mouse | BBA10 | R&D |
| CD44 | Mouse | 103002 | Biolegend |
| E-Cadherin | Mouse | 324102 | Biolegend |
| CEA | | 10-C10C | Fitzgerald |
| B7-H3 | | MAB1027 | R&D |
| EMMPRIN | Mouse | MAB972 | R&D |
| CD45 | Mouse | 304002 | Biolegend |
| Calretinin | Mouse | sc-135853 | Santa Cruz biotechnology |
| Ki67 | Mouse | 556003 | BD Bioscience |
| Control mouse IgG | Mouse | 5414BF | Cell Signaling |
| Control rabbit IgG | Rabbit | 3900BF | Cell Signaling |

The antibody-DNA conjugates were first evaluated in MDA-MB-231 (human breast cancer) cells. Cells were blocked to prevent nonspecific DNA or antibody labeling and then "stained" with the pooled cocktail following techniques akin to standard flow cytometry staining known in the art. Next, DNA was released with a light pulse, hybridized to fluorescent barcodes, and imaged on a cartridge via a charge-coupled imaging device (CCD) (NanoString Technologies).

Several DNA conjugation using various cleavable linkers and corresponding release methods were evaluated and optimized (FIGS. 2 and 3) Among the tested cleavable linkers, the photo-cleavable linker was selected for its superior performance (FIG. 2). Probe quantification translated into proteomic sample profiling (FIG. 1C) by normalizing according to DNA per antibody and housekeeping proteins (FIG. 4). On average, there were about three to five DNA fragments per antibody; markers were thresholded on the basis of nonspecific binding of IgG controls.

Repeated analyses showed consistent results across different batches of cells analyzed on different days and over time (FIG. 5). In subsequent studies, antibodies that did not fall above 1.2-fold control IgG threshold were not included [for example, dimethyl-histone H3 (Lys$^4$)]. Excluding these outliers, the median SE across all antibodies was 6%. A profile of the human MDA-MB-231 line was derived from about 50 cells and showed, for example, high expression of keratin 7 and epidermal growth factor receptor (EGFR), two diagnostic markers commonly used in pathology laboratories to identify cancer subtypes. Epigenetic and phosphoproteomic markers have lower expression because these naturally occur at lower abundance in cells relative to extracellular markers. Intracellular markers such as phospho-Src (pSrc) and phospho-glycogen synthase kinase 3β (pGSK3β) could also be detected, e.g., using the optimized permeabilization method (FIGS. 6A-6B).

Additional benchmarking experiments were performed to demonstrate assay consistency and reproducibility. Conjugated antibodies behaved similarly to native, unmodified antibodies as evidenced by head-to-head comparison on flow cytometry (FIG. 7A). Similar results were found when testing intracellular antibodies such as p53 and phospho-S6 ribosomal protein (pS6RP) with dot blots and immunoblotting (FIG. 7B). Antibody-DNA conjugates generated equal or stronger signals compared to native antibodies on dot blots. Furthermore, the DNA-modified antibodies showed similar expression patterns across cell lysates when compared to native antibody. To assess reproducibility, two DNA-modified antibody clones specific to the same target [e.g., epithelial cell adhesion molecule (EpCAM)] were shown to give nearly identical expression levels ($R^2=0.99$) across multiple cell lines and clinical samples (FIG. 8A). Antibody staining was evaluated using both a cocktail of 60+ antibodies and as single agents; expression levels from both methods, as measured by an antibody barcoding with photocleavable DNA (ABCD) platform as described herein, showed high, linear correlation ($R^2=0.93$; FIG. 8B). Protein marker changes measured with the ABCD platform linearly correlated to expression changes measured by independent immunofluorescence studies in taxol-treated HT1080 fibrosarcoma cells (FIG. 8C). Flow cytometry measurements across eight cell lines and six different markers showed linear correlations ($R^2=0.92$ to $0.99$) (FIG. 9).

Example 3. Single-cell Sensitivity of One Embodiment of the Methods for Multiplex Detection of Target Molecules from a Sample (Antibody Barcoding with Photocleavable DNA (ABCD) Platform)

The sensitivity of the ABCD platform was assessed by detecting across varying cell numbers (50, 15, 10 or 5 cells) from a bulk sample of 500,000 cells, in multiple repeats, by serial dilution (FIG. 10A). The correlations between bulk and diluted DNA counts were linear, with correlation coefficients >0.9 (FIG. 10B). Additional experiments were performed to validate the ABCD platform in single human A431 cells. FIG. 10C displays the expression levels of 90 analyzed proteins for four randomly chosen single cells and in bulk samples. Consistent with previous reports (13), there were some intercellular heterogeneity, but generally, single-cell profiles matched their respective bulk profiles with correlations as high as 0.96 and as low as 0.63. Multinucleated cells were excluded; cells were otherwise selected at random.

To demonstrate biological variation at the single-cell level, untreated single human A431 cells were compared to cells treated with gefitinib-a selective tyrosine kinase inhibitor of the EGFR. Unsupervised clustering of single cells showed unique patterns for treated and untreated groups (FIG. 11A). A431 cell lines overexpress EGFR and are highly sensitive to gefitinib [median inhibitory concentration ($IC_{50}$)=100 nM], as shown by widespread pathway inhibition in gefitinib-treated A431 cells. A threshold was applied at the single-cell level to ensure that marker expression levels were detectable above all six IgG controls for all cell lines. The majority of the panel was still detectable, although some markers such as phospho-EGFR fell below threshold levels in some cells, and thus were not included for hierarchical clustering. Nevertheless, pairwise comparisons between the two cohorts showed significant changes in key markers (FIG. 11B) such as pS6RP, Ku80, and phospho-histone H3 (pH3). These changes in the markers were also consistent with previous reports (14, 15). Unlike most signaling inhibition studies, the untreated cell line was not prestimulated with EGF before treatment. Hence, the assay conditions mimicked natural signaling variability to better approximate patient samples.

Example 4. Measuring Inter- and Intratumoral Heterogeneity in Clinical Samples Using the ABCD Platform To demonstrate the clinical capabilities of ABCD and explore single-cell heterogeneity, FNAs were obtained from patients with lung adenocarcinoma. Single-pass FNA samples were initially processed using antibody-mediated magnetic selection to isolate EpCAM-positive cells. Single cells for subsequent analyses were harvested via micromanipulation, whereas other sample debris was removed. In one representative patient, protein marker expression in 11 single cells (EpCAM+/DAPI+/CD45-) correlated with bulk measurement (about 100 remaining cells from FNAs) (FIG. 12A). Yet overall, correlation between patient cells and bulk FNAs was lower and varied compared to single cells from cell lines and their respective bulk in FIGS. 10A-10C. The highest correlation with the bulk measurement was 0.79 (cell culture showed R=0.96), whereas the lowest value was 0.43 (FIG. 12B).

Interpatient heterogeneity in bulk samples was next determined from six patients with biopsy-proven lung adenocarcinoma (FIG. 13). Although these cancers harbored identical histopathology, proteomic profiling revealed clear differences, even in this small cohort. Marker panels were chosen to evaluate protein heterogeneity across a broad range of functional protein networks (16) relevant for therapy assessment. FIG. 13 shows visual similarity among patients 1, 2, and 5 (Spearman $R_{1,2}=0.94$, $R_{1,5}=0.96$, $R_{2,5}=0.95$). This partially concurred with genotyping because both patients 1 and 2 had EGFR T790M mutations, whereas patient 5 had a KRAS mutation (KRAS 35G>T). This indicates that different genotypes may still yield similar proteomic phenotypes. Patients 3, 4, and 6 harbored distinct proteomic profiles and differing mutations (FIG. 13). Patient 3 had an exon 20 EGFR mutation, whereas patient 4 had an EGFR L858R mutation and an additional BRAF mutation. Patient 6 was noted to have an EML4-ALK translocation.

Protein clustering also showed possible personalized targets (FIG. 13). For example, patient 4 (EGFR/BRAF mutant) had high phospho-extracellular signal-regulated kinase 1/2 (pERK1/2) and pS6RP, as expected for a patient with an EGFR L588R mutation; however, this patient also showed a high level of the DNA repair/damage markers poly(adenosine diphosphate-ribose) polymerase (PARP), Ku80, and phospho-histone H2A.X (pH2A.X) expression, indicating that PARP inhibitors or DNA-damaging agents (for example, cisplatin) could be effective for this patient. Thus, such information determined by methods for detecting a plurality of target molecules as described herein (e.g., ABCD platform) can be used to complement pharmacogenomics.

Figure 15B:
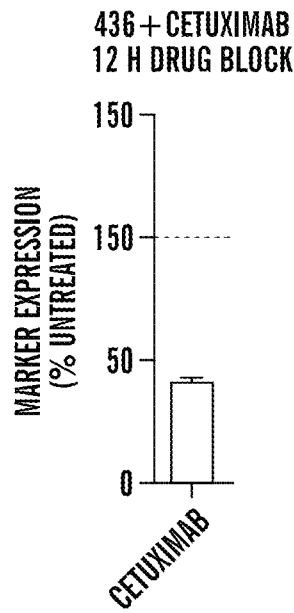
Figure 15C:
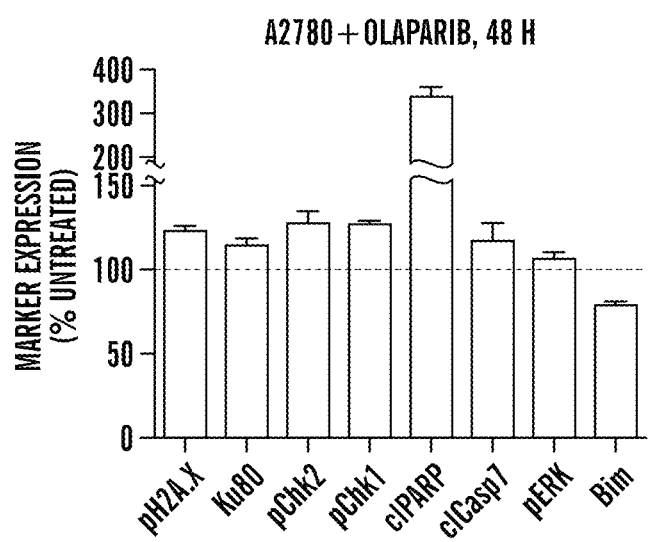
Figure 15D:
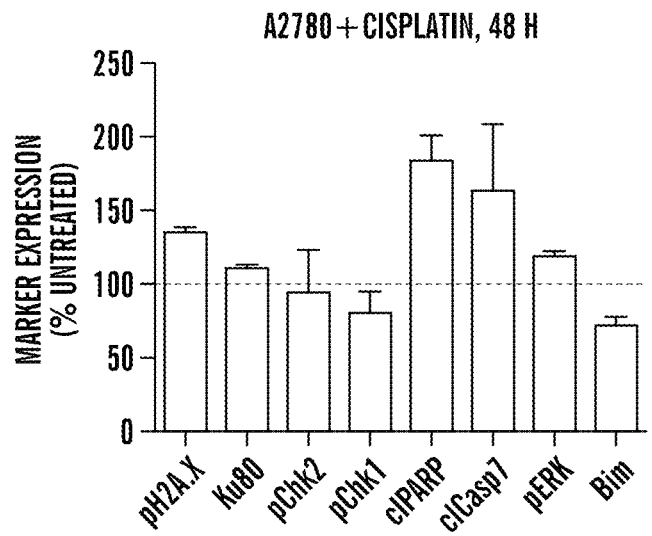
Figure 15E:
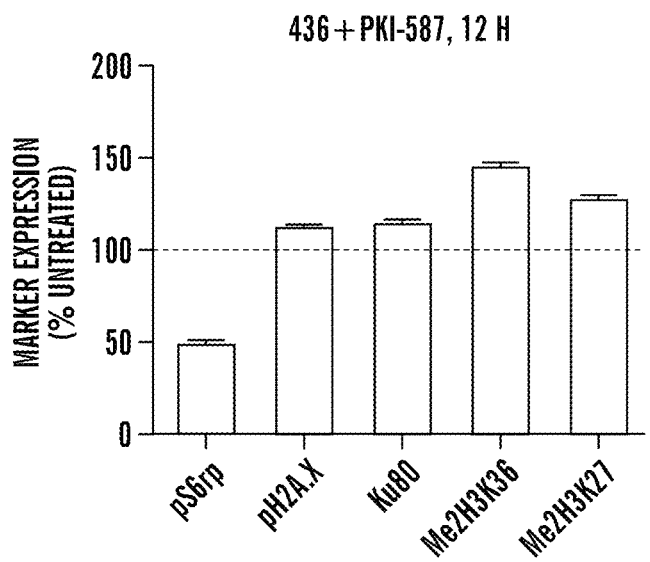

Example 5. In Vitro Discrimination of Pathway Analyses during Treatment Using ABCD Platform Having established feasibility of inter- and intrapatient analyses in clinical samples, it was next sought to explore the feasibility of monitoring cancer treatment over time. To this end, it was first sought to determine if known pathway responses to different drug treatments could be discriminated. FIG. 14A shows the validation that triple-negative breast cancer cells (MDA-MB-436) treated with kinase inhibitors (gefitinib and PKI-587), antibody drugs (cetuximab), and DNA-damaging drugs (olaparib and cisplatin) showed profiles that clustered according to drug mechanism of action. As a control study, cell lines treated with cetuximab resulted in expected drug inhibition (FIG. 15B). Expected protein inhibition in drug-sensitive human cancer cell lines using optimized drug doses and incubation times was demonstrated using the ABCD platform. Notable examples include pS6RP for targeted treatments, and pH2A.X, pATM/ATR (phospho-ataxia telangiectasia mutated/ATM- and Rad3-related) substrate, and cleaved PARP for DNA-damaging agents. Unexpected results, such as epigenetic histone modifications after treatment with a phosphatidylinositol 3-kinase inhibitor (PI3Ki) was also found (FIG. 15E). For additional in vitro validation of treatment, HT1080 fibrosarcoma cell lines were treated with four different doses of taxol. Several panel markers displayed dose-response changes to taxol treatment, including pERK and phospho-cyclin D.

Proteomic profiling of olaparib and cisplatin treatments was performed for four human cancer cell lines, showing varying drug sensitivities as measured by viability assays (FIGS. 14A-14B and FIG. 15A). The degree of change in protein profiles was quantified by calculating the number of markers that were significantly different from the untreated condition using pairwise t test [false discovery rate (FDR)=0.1]. This profiling indicated that global pharmacodynamic changes correlated with treatment sensitivity: As $IC_{50}$ values decreased, the number of protein markers with significant changes increased (FIG. 14B). For resistant cell lines (for example, OVCA429), no significant changes were detected. Expected changes in DNA damage and apoptosis markers, such as degradation of Bim and up-regulation of pERK (FIGS. 15C-15D) were also detected, indicating previous studies of DNA damage response to cisplatin treatment (17).

Figures 16A, 16B:
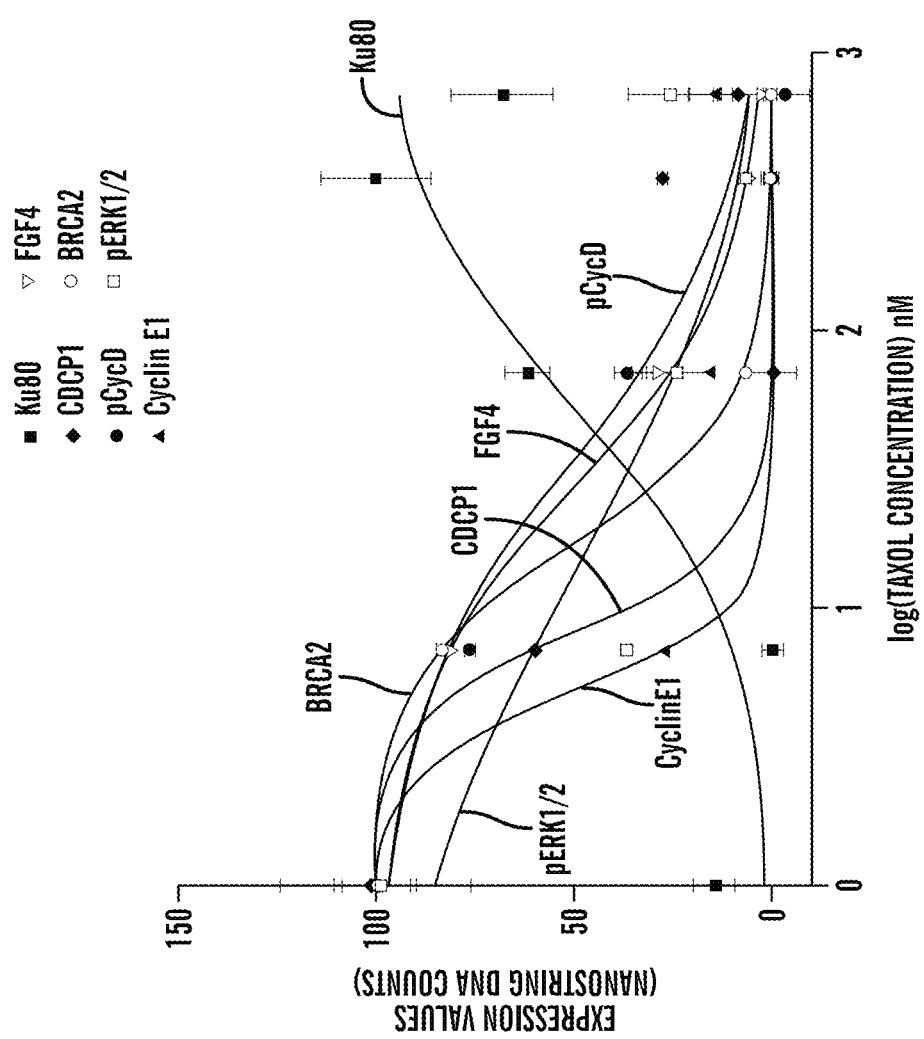

To evaluate the assay's ability to measure even small marker changes, HT1080 human fibrosarcoma cells were treated with taxol at five different doses. Marker changes at high doses were compared to marker changes quantified by an independent immunofluorescence screen (FIG. 16A). Several protein markers showed dose-response curves, including CDCP1, phospho-cyclin D, cyclin E1, fibroblast growth factor 4 (FGF4), BRCA2, and pERK1/2. These in vitro studies established that the marker panel could indeed measure pathway changes in response to varying drug mechanisms; furthermore, these changes could be detected in a sensitive, dose-dependent manner. Additionally, pairwise t tests between the dosed and untreated cells showed an increase in significant marker changes at the highest dose (700 nM taxol) compared to the lower 70 nM dose (FIGS. 16B and 16C).

Example 6. Monitoring PI3Ki Treatment Response in Cancer Patients

In some embodiments, it is desirable to translate these pathway analyses to patient samples, e.g., to analyze serial biopsies in early-phase clinical trials with the goal to better assess drug efficacy and dosage. However, such invasive procedures can introduce risk of morbidity and high costs. The ability to analyze small numbers of cells from alternative sources (for example, FNAs) becomes paramount when responsive tumors shrink after treatment, making repeat biopsies difficult. As proof of concept, scant cell analyses were performed in four patients before and after PI3Ki treatment during phase 1 dose escalation trials (FIG. 17A). Pretreatment samples were collected the day before the first drug dose; post treatment samples were collected at the end of the second treatment cycle. Collection and processing occurred over the course of a year to correlate profiles to patient response. All four patients had metastatic cancers of various subtypes and were selected on the basis of genetic PI3K mutations that could predispose their tumors to pathway inhibition using PI3Ki treatment. In all, two patients responded and two progressed. Data analysis was performed in a blinded manner. Unsupervised clustering separated out two groups of responders versus non-responders (FIG. 17A). Among the two responders, one patient showed larger fold changes across the marker panel. Subsequent unblinding revealed that this patient received a higher dose of the drug during phase 1 dose escalation than did the other responding patient. Additional patient samples can be used to measure ABCD platform's clinical impact during drug dosing pathway studies.

In some embodiments, the screen performed by the ABCD platform could help predict clinical outcome or identify promising markers of treatment response. To demonstrate this, five drug-naïve patients, all with various PI3K mutations, who eventually received small-molecule PI3Ki treatment were profiled. Patients were categorized as non-responders or responders (FIG. 17B) and a marker-ranking algorithm was used to determine top differential markers. The top marker, di-methylation of histone H3 at Lys79 (H3K79me2), clustered with several markers: pS6RP (a known downstream target of PI3K and an emerging key biomarker of treatment response) (14), pH2A.X, and PARP. According to canonical pathway signaling, selecting epigenetic or DNA damage markers as readouts of PI3K treatment response would not be an intuitive decision. DNA damage and epigenetic marker changes were also identified by in vitro profiling of a PI3Ki (FIGS. 15C-15E). This cluster covered diverse proteins across various pathways: epigenetic changes, DNA damage, and growth and survival pathways [PI3K and mitogen-activated protein kinase (MAPK)], indicating the potential value of system-wide profiling for developing better companion diagnostics during treatment.

Discussion Based on Examples 1-6

In some embodiments, presented herein is an amplification-free method capable of sensing hundreds of proteins in human cells by using one or more embodiments of target probes described herein (e.g., DNA-barcoded antibodies) coupled with highly sensitive optical readouts. Cell labeling, washing, and analysis can be completed within hours, making same-day protein analysis possible. The method measures more markers on limited material than immunohistochemistry and preserves genetic material from samples, which is not possible with traditional tools like multiplexed cytometry (18). The protein coverage and/or methods described herein can be extended to include additional protein targets and/or other target molecules through conjugation of target molecules to identification nucleotide sequences (e.g., antibody-DNA conjugations), resulting in a scalable, multiplexed target molecule (e.g., protein) screening platform.

In general, the method can provide analyses of protein expression levels for both single and bulk cell populations. The in vitro studies as shown in the Examples showed that single cells from cell lines showed higher correlation to bulk measurements than those isolated from patient tumors. In FNAs, the single cells also showed higher correlations with each other than with the bulk population. This could be, for example, because an averaged bulk measurement is less likely to correlate strongly with a single clonal phenotype.

The findings presented herein showed that the methods described herein can be used to detect extracellular proteins (e.g., but not limited to, CD44, EGFR), intracellular/cytosolic proteins (e.g., but not limited to, p-S6RP), and/or intracellular/nuclear proteins (e.g., 53BP1) in a sample.

The findings presented herein also showed that current cell culture models are an insufficient estimate of proteomic heterogeneity in clinical samples. The methods for detecting a plurality of target molecules from a sample described herein (e.g., ABCD platform tool) are therefore useful for its ability to study rare single cells in clinical samples, such as circulating tumor cells, stem cells, and immune cell populations. As shown herein, even scarce proteins, such as 53BP1 and pH2A.X, could be detected at the single-cell level. Large-scale protein mapping of isolated, rare cells and clonal populations could shed insight into cancer heterogeneity, drug resistance, and the clinical utility of circulating tumor cells. Intratumoral heterogeneity may itself be a biomarker of poor clinical outcome (19). Thus, the methods described herein (e.g., ABCD platform) can be used to determine intratumoral heterogeneity, which can be used as a biomarker for diagnosis and/or prognosis. Establishing causal and reactive correlations between diseases and altered biomarkers could also radically improve physicians' abilities to diagnose and treat patients (20, 21). In some embodiments, the methods described herein (e.g., ABCD platform) can be used to determine causal and reactive correlations between diseases and altered biomarkers in order to improve physicians' abilities to diagnose and/or treat patients.

The inventors have demonstrated the ABCD method's ease of use, reproducibility, compatibility with clinical applications, such as profiling of FNA cancer samples, and its translational potential to monitor cancer treatment as demonstrated in four patients. The findings showed that broader profiling can improve understanding about potentially useful companion diagnostic biomarkers and help explore how drug dosing corresponds to cellular pharmacodynamics. Smarter protein marker selection, as demonstrated by the ABCD platform, could markedly reduce drug development costs, narrow patient cohorts, and improve clinical trial design.

The methods described herein (e.g., ABCD platform) could complement other art-recognized single-cell proteomic techniques, such as mass cytometry and fluorophore-inactivated multiplexed immunofluorescence (8, 22). One of the advantages of the methods described herein (e.g., ABCD platform) is that both genetic material and protein barcodes can be concurrently extracted from a single sample, thus paving the way for more biologically relevant analyses of protein-DNA-RNA interrelationships. Such integrative measurements could explain "missing pieces" in genomics associated with various diseases or disorders, e.g., cancer genomics. For example, in the Examples presented herein, not all patients with PIK3CA DNA mutations responded to a given PI3Ki; this is consistent with clinical experience (23, 24). However, proteomic biomarkers revealed differential changes between responding and nonresponding cohorts. The Examples indicate that protein profiling will help complement genotyping to shape therapeutic advances for cancer and other diseases.

The Examples presented herein demonstrated proof of principle that the technology described herein can work in clinical samples with a wide range of applications, including rare cell profiling and companion diagnostics within cancer clinical trials.

In some embodiments, the technology described herein (e.g., ABCD platform) can be modified to suit the needs of various applications. For example, the methods described herein (e.g., ABCD platform) can be adapted to work with both whole cells and/or cell lysates, and DNA can be quantified with other readouts (for example, sequencing) to perform simultaneous measurement of RNA, DNA, epigenetic, and protein expression. In some embodiments, the methods described herein (e.g., ABCD platform) can include a module to rapidly isolate and measure entire populations of single cells. For example, additional components and wells can be added to microfluidic devices such as the one described in the Examples to increase the throughput of single-cell analysis.

Single-cell studies can be validated with a higher-throughput device. For example, larger numbers of cells can be used to compare population differences and spreads between the methods described herein and other gold standards (for example, flow cytometry). In some embodiments, the methods described herein (e.g., ABCD platform) can be used to identify novel companion diagnostic markers or specific pathway markers for diagnosis of a disease or disorder (e.g., cancer subtypes) and/or monitoring patients' response therapeutics.

The methods described herein (e.g., ABCD platform) can enable larger-scale studies to yield mechanistic insights into existing and/or novel therapeutic strategies. Moreover, the methods described herein (e.g., ABCD platform) can also be used for rare, single-cell (for example, but not limited to circulating tumor cells) profiling to derive further understanding of their biological and clinical relevance. Because genetic material from samples is preserved, the methods described herein (e.g., ABCD platform) can be adapted to study proteins that interact with genetic regulatory elements such as microRNAs. The methods described herein (e.g., ABCD platform) can be used for various applications in research laboratories, academic hospitals, and pharmaceutical companies to help propel drug trials and biological investigation.

Exemplary Materials and Methods for Examples 1-6

Study Design. In order to determine if protein networks (as opposed to single biomarkers) will reveal clinical or biological insights into how a disease or condition (e.g., cancers) evolves and responds to drugs, a multiplexed platform for detecting protein expression, e.g., in clinical samples and in cell lines, was developed. The Examples herein demonstrate the use of the methods described herein (e.g., ABCD platform) in understanding treatment response in cancer Clinical studies were performed on limited cohorts of patients for proof of principle. The number of patients was selected based on a 1-year enrollment cycle (March 2012 to March 2013). All protein measurements were included as long as their signals were above a pre-determined threshold. In one embodiment, the threshold was ~1.2-fold higher than that of its corresponding nonspecific IgG isotype. This threshold was set to be over three times the median SE from the antibody cohorts pooled. Only antibodies that were validated (via flow cytometry measurements on cell lines) were included. All in vitro studies were performed in replicates (n=3, unless otherwise specified). After optimization, studies with the final protocol were repeated multiple times on different days to ensure consistency and reproducibility. All experiments on clinical studies were performed blinded during experimental procedures and raw data analysis.

Cell lines. Validation experiments were performed in the following cell lines, which were purchased from the American Type Culture Collection (ATCC): SKOV3, ES-2, OVCA429, UCI-107, UCI-101, TOV-112D, TOV-21G, A2780, MDA-MB-231, MDA-MB-436, A431, and HT1080. Cells were passaged in Dulbecco's modified Eagle's medium (Cellgro) or RPMI (Cellgro) as recommended by ATCC. cell lines were derived from ovarian surface epithelium (OSE) brushings cultured in 1:1 Medium 199/MCDB 105 (Sigma-Aldrich) with gentamicin (25 mg/ml) and 15% heat-inactivated serum. TIOSE6 cell lines were obtained by transfecting hTERT into NOSE cells maintained in 1:1 Medium 199/MCDB 105 with gentamicin (25 mg/ml), 15% heat-inactivated serum, and G418 (500 mg/ml) (25). After trypsinization, cells were immediately fixed with 1× Lyse/Fix buffer (BD Bioscience) for 10 min at 37° C. and then washed twice with SB+[phosphate-buffered saline (PBS) with 2% bovine serum albumin (BSA)]. The cells were aliquoted into tubes (~1×10$^6$ cells/ml) and stored at −20° C. until labeling. Biological replicates were seeded in different wells and collected separately. Cultured cells were processed and stored under the exact same conditions as clinical samples. A total of 276 samples were prepared and analyzed independently via the barcoding method.

Clinical samples. The study was approved by the Institutional Review Board at the Dana-Farber/Harvard Cancer Center, and informed consent was obtained from all subjects (n=10). Fourteen minimally invasive procedures were performed on the 10 enrolled patients. Six patients had primary lung adenocarcinomas. The four patients undergoing PI3Ki treatment with repeated biopsies had carcinomas of varying origins in the abdomen, all with underlying PI3K mutations. All pretreatment biopsies were collected in the week before the first cycle of treatment. All post treatment biopsies were collected after a cycle was completed, typically after several weeks to months. Image-guided FNAs with a 22-gauge needle were obtained before routine core biopsies. Correct needle location was confirmed by computed tomography imaging and real-time readout by cytopathology. FNA samples were processed immediately by centrifugation and removal of excess PBS. If there were visual clumps present before the fixation step, collagenase (Sigma-Aldrich) was added at 0.2 mg/ml. Cells were fixed with Lyse/Fix buffer (BD Biosciences) for 10 min at 37° C. and washed twice with PBS with 2% BSA. All centrifugations were performed at 300 g for 5 min. Clinical samples were stored at −20° C. A total of 24 samples were prepared and analyzed independently via the barcoding method.

Drug treatments of cell lines. To test the effect of drug treatment on protein expression levels, the cell lines were treated with a number of different chemotherapeutic or molecularly targeted drugs. A431 cell lines were dosed with gefitinib (Selleck Chemicals) in medium with 1% dimethyl sulfoxide (DMSO) for 12 hours at a concentration of 10 µM. The triple-negative human breast cancer MDA-MB-436 cell line was dosed with the PARP inhibitor olaparib (10 µM in 0.1% DMSO in medium), cisplatin (10 µM, 1% Hanks' balanced salt solution in medium), the PI3K/mTOR inhibitor PKI-587 (100 nM, 0.1% DMSO/medium), and the EGFR inhibitors cetuximab (75 µg/ml in medium) and gefitinib (10 µM in 0.1% DMSO/medium). All molecularly targeted agents (PKI-587, cetuximab, and gefitinib) were applied for 12 hours. DNA-damaging agents olaparib and cisplatin were applied to cells for 3 days. Changes in protein expression levels were compared to medium controls under identical conditions but without drug treatment.

Flow cytometry. Flow cytometry was used to validate protein expression levels in bulk samples. Fixed cells stored at −20° C. were thawed and then permeabilized with a saponin-based buffer, PW+(1× Perm/Wash Phosflow Buffer, BD Biosciences, with 2% BSA). About 200,000 cells per tube were incubated with primary antibodies for 1 hour at either 1 mg/ml or the appropriate dilution as recommended by Cell Signaling for flow cytometry applications. An example list of primary antibodies is shown in Table 1 above. After one wash with PW+, the appropriate secondary antibodies targeting mouse, human, or rabbit IgG were applied. The specific secondary antibodies used were anti-rabbit IgG (H+L) F(ab')$_2$ Fragment Alexa Fluor 647 Conjugate (Cell Signaling #4414), anti-mouse IgG (H+L) F(ab')$_2$ Fragment Alexa Fluor 647 (Cell Signaling #4410), and anti-human FITC (Abcam ab98623). Expression levels for each protein were then calculated by normalizing the geometric mean from each antibody with the appropriate control IgG. These values were then correlated to the expression values derived from the DNA barcoding technique.

Synthesis of photocleavable DNA-antibody bifunctional linker. The photocleavable linker was synthesized as previously described in Ref. 9. For example, compound 1 (FIG. 2B, ~0.100 g, 0.334 mmol) was dispersed in 5 ml of dry dichloromethane (DCM) in a round bottom flask under argon atmosphere. The flask was cooled to 0° C. by placing it on an ice bath. 2-(1H-Benzotriazole-1-yl)-1,1,3,3-tetramethyluronium hexafluorophosphate (HBTU) (0.139 g, 0.368 mmol) and triethylamine (TEA) (109 0.835 mmol) were added to the solution. The reaction mixture was stirred at 0° C. for 5 min, and N-(2-aminoethyl)maleimide trifluoroacetate salt (0.093 mg, 0.368 mmol) was subsequently added. After stirring at 0° C. for 15 min, the reaction mixture was allowed to equilibrate to room temperature while being stirred for 18 h. After the reaction mixture was diluted with DCM (45 ml), the organic phase was washed with water and saturated NaCl solution, then dried over sodium sulfate. The organic layer was concentrated under reduced pressure and charged to a SiO$_2$ column (eluent: 100% DCM to 3% methanol in DCM, v/v) for purification. The yield of compound 2 was approximately 60%. $^1$H NMR (400 MHz, CD$_3$OD): 7.58 (s, 1H), 7.37 (s, 1H), 6.77 (s, 2H), 5.44 (q, $^4$J=6 Hz, 1H), 4.03 (t, $^3$J=6.4 Hz, 2H), 3.94 (s, 3H), 3.61 (t, 3J=5.6 Hz, 2H), 3.35 (t, 2H, overlapping with the solvent residual peak), 2.32 (t, $^3$J=7.2 Hz, 2H), 2.05 (m, $^3$H), 1.46 (d, $^2$J=6.4 Hz, 3H). MS (electrospray ionization mass spectrometry: ESI-MS) calculated: 421.15, found: 466.18 {M+HCOO}$^-$.

Compound 2 (0.010 g, 0.024 mmol) was dissolved in anhydrous dimethylformamide (DMF) (1 ml). N,N'-Disuccinimidyl carbonate (DSC; 0.018 mg, 0.071 mmol) and TEA (12.5 0.096 mmol) were successively added to the solution. The reaction mixture was stirred at RT for 18 h. The reaction mixture was directly loaded onto a C18 reverse phase column for purification (eluent: 5% acetonitrile in water to 95% acetonitrile in water, v/v). The yield of the photocleavable bifunctional linker product was approximately 70%. $^1$H NMR (400 MHz, CDCl$_3$): 7.63 (s, 1H), 7.05 (s, 1H), 6.67 (s, 2H), 6.48 (q, $^4$J=6.4 Hz, 1H), 6.03 (br, 1H), 4.08 (t, $^3$J=5.8 Hz, 2H), 4.02 (s, 3H), 3.68 (m, 2H), 3.45 (m, 2H), 2.79 (s, 4H), 2.36 (t, 3J=7 Hz, 2H), 2.15 (m, 3H), 1.75 (d, $^2$J=6.4 Hz, 3H). ESI-MS calculated: 562.15, found: 607.22 {M+HCOO}$^-$.

DNA-antibody conjugations. Antibodies (e.g., listed in Table 1) were conjugated to specially designed alien DNA sequences derived from the potato genome (exemplary sequences shown in Table 2).

TABLE 2

List of example 70 mer alien sequences used for barcoding a target-binding molecule

| Target sequence | $T_m$ capture probe (° C.) | $T_m$ reporter probe (° C.) |
|---|---|---|
| GCTAAGTTTGGAATTAAGAAAGGAGTTGCTGGAGGTCCTTTCCAGCATAAG AACCAGCCATATTGCTTAA (SEQ ID NO: 1) | 79 | 79 |
| TGCCTTCTGAAAGAGACGTTATTGTTGAAGCAAGAGATAGCTTAGTAACAA ATGCTATAGCTCAGGCAGG (SEQ ID NO: 2) | 80 | 78 |
| CCTGATCATGCTTTGTCAGCAGACCCAGAAGAATTCATCACAATCACTGGA AGATTGAGCTTAGGAAAGT (SEQ ID NO: 3) | 82 | 78 |
| GAGCGGATGTTATTGAGAAGCACTTTACCTTAGATTTCTAAAGCTCTCTTCC TCCTCTCTTCTCCGCTCA (SEQ ID NO: 4) | 78 | 82 |
| ATCGGCTGTGCGATTGCTATTGATGTGTTAAGAAATTTGGTTTGTGATTGGC AAATCTCTCCTCCAACTC (SEQ ID NO: 5) | 80 | 81 |
| ATTTGGATGAAGTCGGCTTTATGGTGACACAAATCATGATGAGCTGAGGTT CTGACAGCAAATACGCTCA (SEQ ID NO: 6) | 79 | 82 |
| ATAGAACCATTTGCTGATGAGGTGACAACAGATCGTTGCACTTATGCTATC CCGTTAGACTATCTGCTAT (SEQ ID NO: 7) | 80 | 78 |
| ACTACCATGTACTGCGCGAGACTAGCCTATCATTGGATTGCAGCGATGACT ATATCTGAGCACCTGTGAC (SEQ ID NO: 8) | 82 | 81 |
| ATATGAGACGACTAGCACGCCATAGCGTTACATACGTGTCGATCCGAGAAC ATCACTCTAATGACGAGTG (SEQ ID NO: 9) | 80 | 81 |
| CATCATCGACAGTTCGCAGCCCTATAACATGATACTAGATAACGATGCTCC ATGTTAGTGAATGCGAGTC (SEQ ID NO: 10) | 80 | 79 |
| ACTCACACATAGTACTGACACGTAAGATAGGATGCTATATGGTCATTGGTC ACCCGAGTTACGATCAAAT (SEQ ID NO: 11) | 79 | 79 |
| CAGATAGACTCACCTCGATATACAGGGAGCCACGACTTAGGACTATGGATA AGTCATCTAAAGCGTCCGA (SEQ ID NO: 12) | 82 | 78 |
| CACTGTCTATACATGGACGACACTTTGCACATCATTACCAAAGAGCGCAAC GTATCTAGGATTGAGCAGT (SEQ ID NO: 13) | 80 | 81 |
| AGACTAATTGATCGGACCGATGACAGTTCACAGAGGGATACACTGTTGAGC CGACCCTATTAGCTGATAT (SEQ ID NO: 14) | 80 | 80 |
| TGATCCACACTGACGAATCATGTACTCACTCGATCGCCACTTCACACAAGA ACACAAATTTGGAGTATTG (SEQ ID NO: 15) | 80 | 79 |
| CTCGAGAATCACACACAGTCGTCTAAGACACGACAAGTGCAACAGCAATC CACATCTTAGATGAGATTAG (SEQ ID NO: 16) | 81 | 78 |
| CGATTACAAGGCGTGGTCAGATATTAGACTCCAGGGGATTTAATGCCAGTC CAAGCTCTCTTCCACATTC (SEQ ID NO: 17) | 81 | 81 |
| ATCTGCATGAACGGGAAAGGAGTTCGATGAGACTTTCAAACCAACATAATG TCTCTCCAACCTCAGGAAG (SEQ ID NO: 18) | 82 | 80 |
| ATAGTCTTTAGAGCCTCAGAATAGGCTGTGACGCGGAAGATAACTCATAAG TGCCTCCCTCGGTAATTTG (SEQ ID NO: 19) | 82 | 79 |
| GCCAGGTATGCCGTGAACGAGTTCTTCATTAACTGTTATGTCTCGGGAGTCT GATATTGGTACTTCTCCC (SEQ ID NO: 20) | 82 | 80 |
| TTAGCACCGATATCAATACTGATGATGTCACCGTCGAGCTCGTGTTGAACC CTTCAAGTAACAACCTGAC (SEQ ID NO: 21) | 79 | 82 |
| ACTTGTTCGACTGACAGTTTAACGCCTGACATGAACGGCTTGCTTATAATGA CTGGCAGGGTTATGAATG (SEQ ID NO: 22) | 81 | 81 |
| AAACTGACCGTACCGTTAGAAGAGAGTTCCGCTTCTCTCATGATGTGCGCA TCTCCCACATTATTTGACC (SEQ ID NO: 23) | 82 | 81 |
| TGATGACAGTGACAATTGACCGAATTGCCTGATCATTACCTTACAGTGCGC AGATTGGGATAATCGATTT (SEQ ID NO: 24) | 81 | 79 |

TABLE 2-continued

List of example 70 mer alien sequences used for barcoding a target-binding molecule

| Target sequence | $T_m$ capture probe (° C.) | $T_m$ reporter probe (° C.) |
|---|---|---|
| TAGGCGTTGAGGCTTTGTTTCTTTGCCTCTATTGTAAGACTCATTCTGACGG CCTCTAGTCGTTGATATG (SEQ ID NO: 25) | 81 | 80 |
| AAGGACATTCTTTCGAATGCAAGTTCAAGGCACATTTTCTATATCAGCCAC CATGGGAGTGACATTTCTT (SEQ ID NO: 26) | 80 | 79 |
| CAATAGCTCCAGTAGTAATTGTTGTCGCTCCGCTGAGCAGTTAATCCTTATG TCAACAACCTCAGCATAG (SEQ ID NO: 27) | 82 | 78 |
| TTCACCAAGCTGAACAGGGTTGCGCTGAATAAATTTTACAGGATACTATGG ACAGGTTCAGAATCCTCGA (SEQ ID NO: 28) | 82 | 79 |
| GGAATGAATCCATTGCATTTCCATGAGAATGCAGACTTAATCGGACGTATC GACTTTGGGTCCACGATAT (SEQ ID NO: 29) | 79 | 80 |
| GAGGTCTTGTTTCATCTAAACCGAGCAGGATGATAAGCCATAATTCGTAAC CCGAGGGTATAATTCGTTA (SEQ ID NO: 30) | 79 | 79 |
| GTCCTTCTGCTTATGACATTCCGTGCATTCCGTAGCTACGTCAAGCGTTACA TAGTGACGGAACTGTTAG (SEQ ID NO: 31) | 82 | 80 |
| TCTGTACCTTGGCACTCCATCTGGTAAGTCACTTATAGTTGTATGGTTTCAG ATGAGGGAACGTGTAGGA (SEQ ID NO: 32) | 81 | 80 |
| AATTTCTGAGATTGTTGGTAGAGGGAGAAATGGGAAGGACATGTTTCAACA ATCACCGGATTAAAGCCTT (SEQ ID NO: 33) | 79 | 80 |
| TGTGGAAGGACTGTGATAAACCAATAGGGTGTCAAGATCTGTAAGTATGGG ATTAGGGATGTTCTGCCAG (SEQ ID NO: 34) | 80 | 80 |
| GCCGTCGGACATAACCACTTGGATATATACGTAGTTCATCAACCTTAACTC CCTCTGGGTTCATTGGGAG (SEQ ID NO: 35) | 80 | 82 |
| GCTATTGCAGCAAAGAGAACAGACGCTTTAACTGGTATCGAGCGCTTAGAT GGCTATATGGTCTACTAGA (SEQ ID NO: 36) | 81 | 78 |
| GAAATCAGATCAGTTCTACATTCGGTGGGAGCCCTCTATATGATTAGATCCT GCAGCCGTACTTCCGTCA (SEQ ID NO: 37) | 82 | 80 |
| GGTGGCTTGATTTAACTGAATCAGGCCCTAACCATTTGTATTGTGTCTACAC TGGTCCGTTCTTAGACGC (SEQ ID NO: 38) | 82 | 81 |
| GTTGTTTACCTTGTAGATCGACTTCACATCAGCGGCAGAAGGCCCTCAACG TAAATCTGCTCCACATTTA (SEQ ID NO: 39) | 80 | 81 |
| TGTTGACATCCGCAACAATGTACCTTATATCGGCATATGGATCTCTTGATCG AGCGAACCTCCCTTTAAC (SEQ ID NO: 40) | 81 | 80 |
| AAGGTGATTCACTAACCAGCTCTTACTCCTCGTTCGGTAGCAAATGAAATG CCGGATGCTGTTGAAGTAG (SEQ ID NO: 41) | 80 | 81 |
| CGCATAACTCGAACCACAGTTACTATCAGTCGACATCCCACCAGAGAAATT GAAGGATATTGTTGAAGCA (SEQ ID NO: 42) | 80 | 79 |
| GAATCTTGGAAGGTTTCCAGTTAAATAGGGCGTGCGAAGATTCCAGGCAGA TTTCTCAGGAATTCAGTCA (SEQ ID NO: 43) | 81 | 80 |
| CTGCTAATGCTGATGGCCCACCTTCTCTATTTGTCGCCATTATATGCGTTGA GGTTAGTTCAAGCAATAC (SEQ ID NO: 44) | 82 | 78 |
| GAACAGCTTTCCTTGCTCCCTCTAAATCACCATTTCCATTAGATGAAACCGA CTTCATTCCAGACTCAAT (SEQ ID NO: 45) | 80 | 78 |
| AATGCATTTGCCAATGTAGCCATTGTATAACCAGATACACTAGTCCAATGT CTCAACCAGGGATACCACA (SEQ ID NO: 46) | 79 | 81 |
| CTCAGAGCTTCAAATCTATCCTCTGGAATCTCTGTATAAGCCCTCGAATACA ACTTGAGGTATCCCGCAT (SEQ ID NO: 47) | 79 | 81 |
| CTCTTCTGCCCTACATCACTATCGACTATAGCAACATATCTTTCTCGGGTAA AGATTAGGCGTCCGATAT (SEQ ID NO: 48) | 79 | 78 |

TABLE 2-continued

List of example 70 mer alien sequences used for barcoding a target-binding molecule

| Target sequence | $T_m$ capture probe (° C.) | $T_m$ reporter probe (° C.) |
|---|---|---|
| GTAACCGTAGTCGCGCAAACCGTTATATTACGGATATGATCCAAGTTATAT ACATTAGGACGCGGTTGCT (SEQ ID NO: 49) | 81 | 79 |
| ATGGTTAGTAAACAGCTTTGATTTCTACATCCGCCTAGCAAACCCATAGTTC TGCAGTAGATTCACAGCG (SEQ ID NO: 50) | 79 | 81 |
| TTCAGTTATAATGTGTCCAGCAGAAGCAGGAATTGAATTACCCAAGTTGCA AGTGGAAGATTTGGAGTTA (SEQ ID NO: 51) | 79 | 78 |
| TTGCAGAAGCATTCCCAATATGGGTTTCAAGAGTTTAAAGAATGTGGAACA TTCATGGGAACTGGTGAAG (SEQ ID NO: 52) | 80 | 79 |
| GCAACAACCTCATCTATACTGTGAATAGTCCCTCCGCTGTCTATATTGGAAC TGCTGCAATGGTTGCTCT (SEQ ID NO: 53) | 80 | 82 |
| CCGCAGATTATCGTTTACGATGCATCCATGGTCTCCGACCCATTGAGAGAG CCAATGGAATTAAGAACTT (SEQ ID NO: 54) | 82 | 80 |
| CACCATTCAGCCTGATATTGCGTTTGGTGTTGATGTGGCAACTGCATACTGA ATAACTCCCTGAAATAGC (SEQ ID NO: 55) | 81 | 80 |
| CGTTACATACTCAGCCATAGGCTTCGATAACAGCATTATTGGAACCTCTGG GACATTAACAGAGACAACA (SEQ ID NO: 56) | 81 | 79 |
| AGCGTACTAGGCATCTATTGGCTGAACTACCATGTAATTAGTGGTGTTCCA GCCTCTAAGATGATGTGGT (SEQ ID NO: 57) | 81 | 80 |
| GATAGGATGCGACTGCGTATCATATAGGCTGCACATTAGCTGTTGCTTCAA ATGCCAATCTTACCTCAAC (SEQ ID NO: 58) | 82 | 79 |
| AATGTATGAGCGGACACTATGCTAAGAGAGACTCCATCAATCCCTCTATGC AAGATAACAACATCTGGCT (SEQ ID NO: 59) | 80 | 79 |
| TGCACATCATAGTGCGACGTTGATCCAGATAGACTATAAGACGGCTTGGCA TTTACCCTAGTCACTATCT (SEQ ID NO: 60) | 81 | 80 |
| AATGTGTCAGCGGCCTAACTGTAATTGATCCACACCTTAGTTCGGGAGCTA CCGATCTAATCAACCGTTT (SEQ ID NO: 61) | 82 | 80 |
| AGACTCCAGGTCGATCATTGGATAACCAACCAGTCGGTTATCCATGACGAG TGAATAATCTTACCGCAGG (SEQ ID NO: 62) | 82 | 80 |
| TTTAGATCCTAAGAATGCGAAATGCCGATTCCCGCATATTTCGTAAGCTCGT TCGGGACTTTGTATCGGC (SEQ ID NO: 63) | 82 | 81 |
| GAGTGATAGGATCACTCTAAGATCGGCCACTATACGACGCTGAGGTTTATA TGAACGGCCGCAATTATGA (SEQ ID NO: 64) | 79 | 81 |
| TCTTGACCAACACCATGTCCGACATACTCCCTAACATGGGTACGGCGACTA CTGAATCGTTCTTTGAGAG (SEQ ID NO: 65) | 82 | 82 |
| TGTGTAAATGAAAGCATCTGACTCAACAGGCATCAGTAACGATAATGAGTA CAACGCCCAATGGTCATAG (SEQ ID NO: 66) | 80 | 79 |
| GCTTCAACGATTTCAATATACCCATTCGTCAGAGGAAGTAGTAGATCCCGC CGTCTTAGTCGGATTGAAA (SEQ ID NO: 67) | 79 | 81 |
| TGTGGTTCCGGTTGCGTATAGATCATGATTCTTTACCCACCTCTTGCTGTAA TGACCACAATCAACGTAG (SEQ ID NO: 68) | 79 | 82 |
| GTATCGGCGAACACGAAATCCTCTACTCTTGACAAACTCCCATTCCTACCTC TCCAAAGTTAGAGGGAGAT (SEQ ID NO: 69) | 81 | 80 |
| TTGCATTACAATGGCCGATCAAGATAAGGACATTCATAATGGAGCTATAGA ATACAACACCAACGTCGCA (SEQ ID NO: 70) | 79 | 79 |
| TAATTCTTCCTTGATTCCGTGATTGGATGTCCCTCAGGAGTAGTAGTGTGGA TGTTGTTGTTAGACACTT (SEQ ID NO: 71) | 79 | 78 |
| TGGAGGGTCGTAACCGCTATAGATGTGATTCACTCCAACAACTTCCCTATCT TTAATCCTCTCACTCCAC (SEQ ID NO: 72) | 81 | 78 |

TABLE 2-continued

List of example 70 mer alien sequences used for barcoding a target-binding molecule

| Target sequence | T$_m$ capture probe (° C.) | T$_m$ reporter probe (° C.) |
|---|---|---|
| TGAATAAATTCGTTGGCGCTGTAGAGATCGGAGTTCCGGATTCGTACTACT CGTTTACGGGATTTACAGA (SEQ ID NO: 73) | 80 | 80 |
| GCTAAAGGAGACTCCGGTTTAAACGTCATCGCAATCTTTGATGGGCAAGCG AGCACATAGATATGCGTTA (SEQ ID NO: 74) | 81 | 82 |
| AATATTCTCCGGCATGAATGGCGTGGGAATGAATCCGGCTTTGTGTTTATTG TACATAGACGTTGTCCCG (SEQ ID NO: 75) | 82 | 81 |
| GAGAACGAGCGGAGCAAGATAGCCTTTAACTGAATCGTCGTCTTATTCCCA GTACACATCATTCCAAATG (SEQ ID NO: 76) | 81 | 79 |
| ATATTCTGTACTCAGTGCCTATCCACCTAATAGGGACCTCAGCGACCTGTCC GTTACATTAATGAAACAT (SEQ ID NO: 77) | 78 | 81 |
| CATTCCGTAGAATTACTACACCGCGGGATCATTATAACGTCGAAGAGCTTC AGAGGTAAGTGAAACAAGG (SEQ ID NO: 78) | 79 | 81 |
| CCCGAAGGCATAATCAACATCCATTGTACATCCCTTGTTATAGCTCCAGGG CCAGAGATTAAAGGAATAG (SEQ ID NO: 79) | 81 | 79 |
| CTAGGATGTAACTTGCGTTAGTTGCAGATTCGCTATATTGCTTAAGCTCTGA GCTCCATGTCCAGTAATT (SEQ ID NO: 80) | 79 | 79 |
| TTCTCGCAGTTGTAAACTTATAGTGTCGCGCCTAGAAATTCATAGCCACAA ATTCTCTTTGGGCAGAGAT (SEQ ID NO: 81) | 81 | 78 |
| TATAGTTACCAAGTACTATGGGTTGGTGGAAGCCGAACGTCTGTCCAAATG GAGCTATAGTTAAGAGGGA (SEQ ID NO: 82) | 80 | 80 |
| AGACGCACACCGATAGAGGAGAGATCTTACATACCTGCTAAGGTTGTTAAT GGCATTGCAGATAGCTTAG (SEQ ID NO: 83) | 81 | 79 |
| CCAGAAAGGTACAGGGCCAATTAACACGTAATCGGCCTCCAACTCTGCCAT CTTTAAGCATTCTAAAGCT (SEQ ID NO: 84) | 82 | 80 |
| AATTCTCCGTCATGTGGTCGTCTGATGCCTAACTTTATCTGCTATCAATGTA GAGGATCGTGCATTACCG (SEQ ID NO: 85) | 82 | 79 |
| CGCGGGCTAAGTAGTAGGGTTCTAATGCTACTTTAAATACGCTCACAATCC AGGCTATATCGCTGTAGCT (SEQ ID NO: 86) | 80 | 81 |
| TAATCACTGTATTTGTTAATCATGGCTAGGCGGGTCCAATAGGGAAACTGA TACTAACGTAGGAGCACGC (SEQ ID NO: 87) | 79 | 81 |
| GTATTCTGGAGAACCTCGTGGCAATGGCAATTCTCCACGAGTGCTAAGATC TGAGCCGTTTACCAAAGAG (SEQ ID NO: 88) | 82 | 81 |
| ATAACCTGGTCTCCGGTTGATCGTTTACCTGAAACATGAGATTAGCAACGA CCCAAACATGCCACTTCAC (SEQ ID NO: 89) | 81 | 82 |
| CACAACATGCAGCAGGCAAGTAGGGTTTCTGATTATAAGCATCCAGCAATA AAGCCTCCTTCAAACCAAC (SEQ ID NO: 90) | 81 | 81 |
| CCCTAACCATGTTCTACGAGCGGTCACAGATTATATTCAACTACAAGTGTA AATGTACGAGCGCCGAGAT (SEQ ID NO: 91) | 80 | 80 |
| GAAAGGCATTTGACGGGAGCATTGACGAAGACATACGGTAATTTGTCGTCG CACGGACAATTAGTGAGTT (SEQ ID NO: 92) | 82 | 81 |
| TAATACTGGGTCACAAGATTAGATTCCAGCTGTGACGGCGATGAAGTCCGC GAGGATATGTTTCTATATC (SEQ ID NO: 93) | 78 | 81 |
| GGTTCATTGTCTCATCGTACGGCTAATGTAGATACGAGGTAGCCGAGTATG ACACACCACAGCAGTTAAT (SEQ ID NO: 94) | 78 | 82 |
| TTATGGATTCCGATGATCCTCCGCGTGGTACAAATGTTACCTTGATGCAATA GTCTCTGTATGCGATCGG (SEQ ID NO: 95) | 82 | 80 |
| AGCGGTACTAATATGCTATGAGCGAGTTCCCTAACGAGAGATAACGACCCT CTGTCGTAAGCACTTAAGG (SEQ ID NO: 96) | 80 | 81 |

TABLE 2-continued

List of example 70 mer alien sequences used for barcoding a target-binding molecule

| Target sequence | $T_m$ capture probe (° C.) | $T_m$ reporter probe (° C.) |
|---|---|---|
| GAGGCATCTCTGCTAACTATATGCTGAACAGCTTTTCCACGATATAGGTAC ATTGGACGCTTACAGGATA (SEQ ID NO: 97) | 80 | 79 |
| TTTCGGCCCAACTTATATGCTCTCCGAATCTTGGAGCAGTCATCGTAACCTG ATAGCAATCTACGTCAAG (SEQ ID NO: 98) | 82 | 80 |
| ACTGCAGTGAGGGCAACCAATACAAATTAAATCTGCCTCCTATTGGGATAC CTCCCGTCCATTAAGTTAG (SEQ ID NO: 99) | 79 | 80 |
| TTGGAGAAACAACCATACAGGTGTCTTTAACTACCTGGAACTCTACCAATT GGAGCTTTCTTAGCTGTCT (SEQ ID NO: 100) | 78 | 80 |
| GCTATCAACTTCCCTATCCAAACCGTTGGATGAATTGAAAGCATAGATGTT CCTTGGAGAGGTTTCCCAG (SEQ ID NO: 101) | 80 | 81 |
| TGAGGAGTAAGTATACGACGCCTGCACTAGTCACTTGCTGGCTTTGAGCCA ATAGATGTGTTAATGGCTA (SEQ ID NO: 102) | 82 | 81 |
| CACAGCCAATCTCTTAGGACAGTACATGGTTAGTAACGTCTGTGGAAGTCA TGAGCACACGATCTGTAAG (SEQ ID NO: 103) | 79 | 82 |
| TGAGTATCTACAGGTGTTCTCATGGGATCGTAGTTGGTCTGTCCAACATGAC GTTATAGGCATAACTCCA (SEQ ID NO: 104) | 79 | 81 |
| TACCTTAAACTGCGCTGGTAACTTGGATCGTGTAGTCATTGGGAGCAAACC ATCTGTCTTTCGTATGGAG (SEQ ID NO: 105) | 81 | 81 |
| GTTAGGTTCAGCCTCATTCCCTAAGAATCCAACTCATAACTCAATCATGCGC GTCCAGCAAAGACAAATG (SEQ ID NO: 106) | 80 | 81 |
| ACTGTCTAATACAACCGGATTCTAAGACCACATGGTCTTAGACGCGCGTGC AATTCTGAACTATATGATT (SEQ ID NO: 107) | 79 | 79 |
| TGGCTATTGCCGCAGTAGATCAAAGATTGAGAGAGATATAGATTACTCCAT GATACACCCAAGCCTCGAC (SEQ ID NO: 108) | 81 | 79 |
| GCAACAAGTGATGCTGACGCAGTTGTTATAGATGGCCTTTGGCTCACGCTA ATTGAGTTACTGTAGGAAA (SEQ ID NO: 109) | 81 | 80 |
| GCTATCTCACCAGCTCCTCACCATGACATTTACTCTCCACATTTATCTGCGA CCTGTTTCGTAAACGATG (SEQ ID NO: 110) | 81 | 80 |

The 70-mer sequence length was selected for optimal hybridization with the NanoString capture and reporter probes. Other sizes were evaluated as well. Shortening sequence length tended to improve signal but reduce hybridization capability. For example, although 50-mer sequences gave relatively higher signals when compared to controls, 30-mer sequences did not reliably hybridize. Thus, 70-mer sequences were selected for reliable hybridization. However, sequences that are longer or shorter than 70 nucleotides can also be used in the methods described herein.

Antibodies (e.g., listed in Table 1) can be purchased from commercial sources, and were initially purified from BSA and/or other contaminants with either a Zeba spin column or centrifugal filter. Antibodies were then incubated with photocleavable bifunctional linker in PBS (containing 5% N,N'-dimethylformamide and 10% 0.1 M NaHCO$_3$) at room temperature for 1.5 hours. Afterward, excess reagents were removed from maleimide-activated antibodies with a Zeba spin column [7000 molecular weight cutoff (MWCO), eluent: PBS].

Thiol-modified DNA oligos (from Integrated DNA Technologies) were reduced with dithiothreitol (DTT; 100 mM) in PBS (1 mM EDTA, pH 8.0) for 2 hours at room temperature. The reduced DNA oligos were then purified with NAP-5 column (GE Healthcare), with deionized water as the eluent. The fractions containing DTT (determined with the microBCA assay) were discarded. The remaining reduced DNA fractions were pooled and concentrated with a 3000 MWCO Amicon filter (Millipore).

The maleimide-activated antibodies were incubated with the reduced DNA oligos in PBS solution. In a typical conjugation process, 15-fold molar excess of DNA oligos was incubated with maleimide-activated antibodies. The conjugation reaction was allowed to proceed for 12 hours at 4° C. DNA barcode-antibody conjugates were purified with a Millipore 100K MWCO centrifugal filter followed by three washes with PBS. After the antibodies were mixed, a final purification of excess DNA was conducted with protein A/G-coated magnetic beads (Pierce/Thermo Scientific). The commercial protocol from Thermo for magnetic separation was only slightly modified to use a tris-buffered saline (TBS)/0.1% Tween wash buffer and a Gentle Ag/Ab Elution Buffer (Thermo Scientific). Three elutions were performed for 20 min each. Solvent antibody was exchanged into pure TBS with a Zeba desalting column (7000 MWCO).

Antibody characterization. Antibodies were aliquoted and stored at concentrations of 0.25 mg/ml in PBS with BSA (0.15 mg/ml) at −20° C., with adequate usage for at least twelve experimental runs (the number of runs on each NanoString cartridge) to avoid freeze-thaw cycles. Various other storage methods were tested, including glycerol or 4° C. storage, but aliquoting and freezing showed the most consistent, high-fidelity storage for up to 9 months. Antibody concentrations were determined via microBCA assay (Thermo Scientific). DNA concentrations were also independently determined using the Qubit ssDNA kit (Invitrogen) to quantify the relative number of DNA per antibody. To achieve relative DNA/Ab measurements with higher sensitivity across the cohort of antibodies, in some embodiments, the NanoString platform was used to add antibody cocktails under two conditions: (1) "Control": antibodies were added in their native forms with DNA still attached, and (2) "Released DNA": antibodies were treated with proteinase K and photocleaved. Under the control condition, the DNA was still attached to the antibody and thus could not simultaneously bind to the NanoString assay's reporter and capture probe. The difference in DNA readings between these two measurements thus revealed the relative number of DNA per antibody. This difference was divided by the isotype control measurement to account for possible inherent experimental error in protein concentration and/or antibody isolation (see FIG. 6 for relative number of DNA:Ab ratio). Antibodies were rigorously tested and validated prior to use. Of 110 antibodies, 88 were selected for the final panel and all had been previously validated from specific vendors (primarily Cell Signaling Technologies, BioLegend; Table 1). Antibodies that did not work with DNA conjugates did not work in their native state either and were excluded; DNA conjugated antibodies worked as well as the parent antibody (FIGS. 7A-7B).

Antibody staining and DNA collection for protein profiling. Prior to cell staining, antibodies were pooled into a cocktail with TBS, 0.1% Tween, and 0.2 mg/ml cysteine (to avoid DNA cross-reaction with other antibodies). Tubes were coated with serum blocking buffer overnight to prevent samples from non-specifically binding to tube walls. Cells were then incubated for a minimum of one hour with a blocking buffer at 37° C.: 10% v/v Rabbit serum (Jackson Immuno Research Labs, 011-000-120), 2% BSA, 1 mg/ml SS salmon sperm DNA (Sigma Aldrich, D7656), 0.2 mg/ml cysteine (Sigma Aldrich), 20× Perm (BD Bioscience) or 0.1% Tween 20 (Sigma Aldrich)—all in PBS to minimize non-specific antibody or DNA binding. The antibody cocktail was then added to the fixed and permeabilized cells and incubated for one hour at RT with intermittent mixing.

After incubation, the cells were washed with PW+ with 0.05 mg/ml of DS sheared salmon sperm DNA (Life Technology, AM9680). Either two 15-ml washes in 15-ml tubes or four 1.5-ml washes in 1.7-ml microcentrifuge tubes were performed. Blocking and wash steps were desired for achieving low background even with femtomolar detection. All washes were performed on ice. Labeled cells could then be counted and selected for lysis/proteinase K/photocleavage to release the DNA. Lysis buffer was used on 10 μl of cells (with up to 50,000 cells), 34.2 μl of ATL lysis buffer (Qiagen) and 5.8 μl of Proteinase K (Qiagen). This reaction proceeded at 56° C. for a minimum of 30 min. Photocleavage was then performed using long UV wavelength light (model) for 15 min. This resulted in a cell-lysis mix with released DNA. Samples were spun down at 14,000×g for 10 min. Supernatant was collected, and serial dilutions were performed in nuclease-free water (Invitrogen, AM9937) to collect DNA equivalent to 50-100 cells to avoid saturating the read-out cartridge (Nanostring). This amount resulted in cartridge binding densities within the linear range of quantitation. Binding densities in the lower range (0.05-0.2) were still linear and gave consistent protein profiles comparable to those in the higher range (1.5-2.5). At lower binding densities (for example single cells), the majority of markers could be measured, with the exception of low expression markers with weaker antibodies (pJAK2, pChk2).

Immunofluorescence. Immunofluorescence provided an independent measure and validated marker changes from paclitaxel (Taxol) treatment (FIGS. 16A-16B). HT1080 cells were seeded at 4,000 cells per well in 96 well plates (Grenier), which were compatible with high resolution plates, and grown for 24h in DMEM media before either being treated with Paclitaxel at 100 nM or kept in control media. After 24 h, cells were fixed for 15 min at RT, then gently washed on a rocker with PBS/0.1% Tween for 5 min, repeated 3 times. All subsequent washes were also performed with this buffer, time duration, and repetition protocol.

Cells were then permeabilized with ice cold 90% methanol for 20 min. After washing, cells were blocked for 1 h at room temperature with blocking buffer (Odyssey). Primary antibodies (all from Cell Signaling; see Table 1) were then added in blocking buffer at prescribed dilutions, sealed, covered in foil and incubated overnight. The next day, after washing, anti-rabbit-FITC secondary antibodies, 1:500 Hoechst and 1:200 whole-cell stain blue (Cellomics) were added (all primary antibodies were rabbit IgGs) at 2 mg/ml and incubated for 2 h. Final wash steps were performed in PBS only, and the cells were subsequently imaged at 20× using an Olympus microscope (BX63) with a Delta Vision chamber and software. All images were taken in biological triplicate. Fluorescence intensity for each cell was determined using CellProfiler, which used Hoechst and whole-cell stain to delineate cell boundaries and size constraints to discount debris. Additional in-house MATLAB (Mathworks) code was then used to calculate marker signals for each condition and calculate the changes between treated and untreated cells.

Immunoblotting and dot blotting. OVCAR3, SKOV3, CAOV3, A2780, and OVCAR429 cell lines were plated in 6-well dishes and grown for 72 h prior to lysis for Western blot analysis. Cells were washed twice with ice-cold PBS, scraped into 200 μl per dish of radio immunoprecipitation assay buffer (RIPA buffer) (Cell Signaling Technology), containing HALT protease and phosphatase inhibitor cocktail (Pierce), and transferred to 2 ml microcentrifuge tubes. Lysates was passed through a 23-g syringe 5 times, and then incubated 5 min on ice with vortexing every min. Lysates were centrifuged 15 min at 14,000×g (4° C.). Supernatant was transferred to a new microcentrifuge tube and total protein was measured using the BCA assay. Equal total protein was prepared, boiled, and loaded on a Novex NuPAGE 4-12% Bis-Tris gel and then transferred to nitrocellulose.

Membranes were blocked for 1 h at room temperature in SuperBlock T20 (TBS) buffer (Pierce) and then washed briefly in tris-buffered saline (TBS) with 0.1% Tween-20 (TBST). Membranes were then incubated overnight at 4° C. with rocking in p53 (1:1000, Cell Signaling), DNA-conjugated p53 (1:1000), pS6RP (1:1000, Cell Signaling), or DNA-conjugated pS6RP (1:1000) primary antibodies diluted in TBST with 10% SuperBlock. Membranes were washed three times, 5 min each in TBST and then incubated 1 h at room temperature in goat a-rabbit HRP conjugated secondary antibody diluted 1:1000 in TBST with 10% SuperBlock. Following washing, signal was detected using SuperSignal West Pico chemiluminescent substrate (Pierce).

For the Ki67 antibodies, 1ug cell lysates (prior to denaturing) from above were loaded onto nitrocellulose a Bio-Dot microfiltration apparatus (Bio-Rad). Blots were then processed as above, using a Ki67 or DNA-conjugated Ki67 antibody (1:1000, BD Biosciences) and an α-mouse HRP conjugated secondary antibody diluted as above. Dot blots were detected as above.

Single-cell isolation and processing. After antibody staining, single cells were picked with a micromanipulator. Cells were stained with Hoechst 3342 (Molecular Probes), added to an open 10-cm dish, and imaged with a TE2000 microscope (Nikon). Single cells were placed directly into a PCR tube. Five microliters of lysis buffer/proteinase K was added (4.5 µl of ATL buffer and 0.5 µl of proteinase K). Lysis/enzymatic cleavage proceeded for 30 min at 56° C. before photocleavage for 15 min. Reporter and capture probes (NanoString Technologies) were then directly added to this tube according to the manufacturer's recommendations.

Data analysis: calculating proteomic expression profiles. Protein expression profiles were extracted from raw data as follows. First, raw DNA counts were normalized via the mean of the internal NanoString positive controls, which account for hybridization efficiency. These counts were then converted to antibody expression values using the relative DNA/antibody counts. Next, average background signal from control IgG was subtracted. Last, housekeeping genes were used for normalization that accounted for cell number variations. Signals were normalized via a house-keeping protein, e.g., β-tubulin. For the taxol treatments, signals were normalized via the geometric mean of histone H3, GAPDH, and actin rather than tubulin, because tubulin is a primary target of taxol. Data were transformed into log 2 scale as denoted in captions.

Data analysis: clustering. Heat maps and clustergrams were plotted using MATLAB with a matrix input of marker expression values that were calculated as detailed above. All shown clustergrams were performed as a weighted linkage and were clustered using correlation values as a distance metric. Some clustergrams were normalized by row, as specified in captions, to highlight marker differences among different patients. If a marker was not detectable in one of the patients, it was removed from the matrix or heat map and is not displayed.

Statistical analysis. Raw data from NanoString DNA counts were normalized by first using the nSolver analysis software to account for hybridization differences on the cartridge. Only positive controls A to D on the NanoString software were used in normalization. DNA counts were within the linear range of detection and met all other criteria for inclusion as determined by the nSolver software (maximum fields of view, image quality, etc.). After determining an expression value by taking into account nonspecific IgG binding and housekeeping genes (cell count), data were log 2-transformed.

Correlation between single-cell analysis and bulk measurement was calculated in GraphPad Prism. Spearman r values were calculated without assuming a normal, consistent distribution. Two-sided P values were calculated, where significant markers were identified by comparing two groups (for example, treated versus untreated) in Prism and performing pairwise t tests with an FDR of 0.2 for multiple test correction error. Significant marker changes and their P values between gefitinib-treated and untreated A431 single cells are shown in Table 3 below. For heat maps, if any samples had markers below threshold, the entire marker row was removed (no imputed data values were used). To identify differentiating markers between responders and nonresponders, a multiclass sequential forward selection-ranking algorithm was used. The patients were classified as responders or nonresponders based on known data. Class separability was measured by the Bhattacharya distance.

TABLE 3

Significant markers between A431 single cells with or without gefitinib treatment. Six markers out of 49 markers showed significant difference between gefitinib-treated vs. untreated A431 single cells and the average expression values as calculated via Nanostring profiling for each cohort. Marker significance was determined by pairwise t-testing and corrected for multiple testing errors by using a false discovery rate of 0.2.

| Proteins | P | Untreated | Treated |
| --- | --- | --- | --- |
| Phospho-S6RP | 0.0067212 | 1171.3 | 58.4 |
| Phospho-histone H3 | 0.0091305 | 4920.6 | 982.0 |
| Ku80 | 0.0098001 | 770.2 | 120.6 |
| FGFR4 | 0.0106319 | 914.9 | 114.1 |
| CD56 | 0.0117795 | 1906.5 | 334.4 |
| Dimethyl-histone H3 (Lys36) | 0.0119939 | 695.7 | 86.9 |

REFERENCES

1. M. Basik, A. Aguilar-Mahecha, C. Rousseau, Z. Diaz, S. Tejpar, A. Spatz, C. M. Greenwood, G. Batist, Biopsies: Next-generation biospecimens for tailoring therapy. Nat. Rev. Clin. Oncol. 10, 437-450 (2013).
2. B. Vogelstein, N. Papadopoulos, V. E. Velculescu, S. Zhou, L. A. Diaz Jr., K. W. Kinzler, Cancer genome landscapes. Science 339, 1546-1558 (2013).
3. J. G. Paez, P. A. Janne, J. C. Lee, S. Tracy, H. Greulich, S. Gabriel, P. Herman, F. J. Kaye, N. Lindeman, T. J. Boggon, K. Naoki, H. Sasaki, V. Fujii, M. J. Eck, W. R. Sellers, B. E. Johnson, M. Meyerson, EGFR mutations in lung cancer: Correlation with clinical response to gefitinib therapy. Science 304, 1497-1500 (2004).
4. M. Soda, V. L. Choi, M. Enomoto, S. Takada, V. Vamashita, S. Ishikawa, S. Fujiwara, H. Watanabe, K. Kurashina, H. Hatanaka, M. Bando, S. Ohno, V. Ishikawa, H. Aburatani, T. Niki, V. Sohara, V. Sugiyama, H. Mano, Identification of the transforming EML4-ALK fusion gene in non-small-cell lung cancer. Nature 448, 561-566 (2007).
5. M. B. Vaffe, The scientific drunk and the lamppost: Massive sequencing efforts in cancer discovery and treatment. Sci. Signal. 6, pe13 (2013).
6. E. D. Hsi, A practical approach for evaluating new antibodies in the clinical immunohistochemistry laboratory. Arch. Pathol. Lab. Med. 125, 289-294 (2001).
7. E. J. Lanni, S. S. Rubakhin, J. V. Sweedler, Mass spectrometry imaging and profiling of single cells. J. Proteomics 75, 5036-5051 (2012).
8. S. C. Bendall, E. F. Simonds, P. Qiu, A. D. Amir el, P. O. Krutzik, R. Finck, R. V. Bruggner, R. Melamed, A. Trejo, O. I. Ornatsky, R. S. Balderas, S. K. Plevritis, K. Sachs, D. Pe'er, S. D. Tanner, G. P. Nolan, Single-cell mass cytometry of differential immune and drug responses across a human hematopoietic continuum. Science 332, 687-696 (2011).
9. S. S. Agasti, M. Liong, V. M. Peterson, H. Lee, R. Weissleder, Photocleavable DNA barcode-antibody conjugates allow sensitive and multiplexed protein analysis in single cells. J. Am. Chem. Soc. 134, 18499-18502 (2012).
10. P. Fortina, S. Surrey, Digital mRNA profiling. Nat. Biotechnol. 26, 293-294 (2008).

11. G. K. Geiss, R. E. Bumgarner, B. Birditt, T. Dahl, N. Dowidar, D. L. Dunaway, H. P. Fell, S. Ferree, R. D. George, T. Grogan, J. J. James, M. Maysuria, J. D. Mitton, P. Oliveri, J. L. Osborn, T. Peng, A. L. Ratcliffe, P. J. Webster, E. H. Davidson, L. Hood, K. Dimitrov, Direct multiplexed measurement of gene expression with color-coded probe pairs. Nat. Biotechnol. 26, 317-325 (2008).
12. J. Chung, D. Issadore, A. Ullal, K. Lee, R. Weissleder, H. Lee, Rare cell isolation and profiling on a hybrid magnetic/size-sorting chip. Biomicrofluidics 7, 054107 (2013).
13. S. L. Spencer, S. Gaudet, J. G. Albeck, J. M. Burke, P. K. Sorger, Non-genetic origins of cell-to-cell variability in TRAIL-induced apoptosis. Nature 459, 428-432 (2009).
14. J. N. Andersen, S. Sathyanarayanan, A. Di Bacco, A. Chi, T. Zhang, A. H. Chen, B. Dolinski, M. Kraus, B. Roberts, W. Arthur, R. A. Klinghoffer, D. Gargano, L. Li, I. Feldman, B. Lynch, J. Rush, R. C. Hendrickson, P. Blume-Jensen, C. P. Paweletz, Pathway-based identification of biomarkers for targeted therapeutics: Personalized oncology with PI3K pathway inhibitors. Sci. Transl. Med. 2, 43ra55 (2010).
15. S. Shintani, C. Li, M. Mihara, N. Terakado, J. Vano, K. Nakashiro, H. Hamakawa, Enhancement of tumor radioresponse by combined treatment with gefitinib (Iressa, ZD1839), an epidermal growth factor receptor tyrosine kinase inhibitor, is accompanied by inhibition of DNA damage repair and cell growth in oral cancer. Int. J. Cancer 107, 1030-1037 (2003).
16. D. Hanahan, R. A. Weinberg, Hallmarks of cancer: The next generation. Cell 144, 646-674 (2011).
17. J. Wang, J. V. Zhou, G. S. Wu, Bim protein degradation contributes to cisplatin resistance. J. Biol. Chem. 286, 22384-22392 (2011).
18. C. Benoist, N. Hacohen, Immunology. Flow cytometry, amped up. Science 332, 677-678 (2011).
19. N. McGranahan, R. A. Burrell, D. Endesfelder, M. R. Novelli, C. Swanton, Cancer chromosomal instability: Therapeutic and diagnostic challenges. EMBO Rep. 13, 528-538 (2012).
20. J. Bousquet, J. M. Anto, P. J. Sterk, I. M. Adcock, K. F. Chung, J. Roca, A. Agusti, C. Brightling, A. Cambon-Thomsen, A. Cesario, S. Abdelhak, S. E. Antonarakis, A. Avignon, A. Ballabio, E. Baraldi, A. Baranov, T. Bieber, J. Bockaert, S. Brahmachari, C. Brambilla, J. Bringer, M. Dauzat, I. Ernberg, L. Fabbri, P. Froguel, D. Galas, T. Gojobori, P. Hunter, C. Jorgensen, F. Kauffmann, P. Kourilsky, M. L. Kowalski, D. Lancet, C. L. Pen, J. Mallet, B. Mayosi, J. Mercier, A. Metspalu, J. H. Nadeau, G. Ninot, D. Noble, M. Öztürk, S. Palkonen, C. Préfaut, K. Rabe, E. Renard, R. G. Roberts, B. Samolinski, H. J. Schunemann, H. U. Simon, M. B. Soares, G. Superti-Furga, J. Tegner, S. Verjovski-Almeida, P. Wellstead, O. Wolkenhauer, E. Wouters, R. Balling, A. J. Brookes, D. Charron, C. Pison, Z. Chen, L. Hood, C. Auffray, Systems medicine and integrated care to combat chronic noncommunicable diseases. Genome Med. 3, 43 (2011).
21. E. E. Schadt, Molecular networks as sensors and drivers of common human diseases. Nature 461, 218-223 (2009).
22. M. J. Gerdes, C. J. Sevinsky, A. Sood, S. Adak, M. O. Bello, A. Bordwell, A. Can, A. Corwin, S. Dinn, R. J. Filkins, D. Hollman, V. Kamath, S. Kaanumalle, K. Kenny, M. Larsen, M. Lazare, Q. Li, C. Lowes, C. C. McCulloch, E. McDonough, M. C. Montalto, Z. Pang, J. Rittscher, A. Santamaria-Pang, B. D. Sarachan, M. L. Seel, A. Seppo, K. Shaikh, Y. Sui, J. Zhang, F. Ginty, Highly multiplexed single-cell analysis of formalin-fixed, paraffin-embedded cancer tissue. Proc. Natl. Acad. Sci. U.S.A. 110, 11982-11987 (2013).
23. F. Janku, J. J. Wheler, S. N. Westin, S. L. Moulder, A. Naing, A. M. Tsimberidou, S. Fu, G. S. Falchook, D. S. Hong, I. Garrido-Laguna, R. Luthra, J. J. Lee, K. H. Lu, R. Kurzrock, PI3K/AKT/mTOR inhibitors in patients with breast and gynecologic malignancies harboring PIK3CA mutations. J. Clin. Oncol. 30, 777-782 (2012).
24. M. Elkabets, S. Vora, D. Juric, N. Morse, M. Mino-Kenudson, T. Muranen, J. Tao, A. B. Campos, J. Rodon, Y. H. Ibrahim, V. Serra, V. Rodrik-Outmezguine, S. Hazra, S. Singh, P. Kim, C. Quadt, M. Liu, A. Huang, N. Rosen, J. A. Engelman, M. Scaltriti, J. Baselga, mTORC1 inhibition is required for sensitivity to PI3K p110a inhibitors in PIK3CA-mutant breast cancer. Sci. Transl. Med. 5, 196ra99 (2013).
25. K. K. Zorn, A. A. Jazaeri, C. S. Awtrey, G. J. Gardner, S. C. Mok, J. Boyd, M. J. Birrer, Choice of normal ovarian control influences determination of differentially expressed genes in ovarian cancer expression profiling studies. Clin. Cancer Res. 9, 4811-4818 (2003).
26. N. K. Devaraj, R. Upadhyay, J. B. Haun, S. A. Hilderbrand, R. Weissleder, Fast and sensitive pretargeted labeling of cancer cells through a tetrazine/trans-cyclooctene cycloaddition. Angew. Chem. Int. Ed. Engl. 48, 7013-7016 (2009).

What is claimed is:

1. A method for detecting a plurality of target molecules in a sample comprising:
   a. contacting a sample with a composition comprising a plurality of target probes, wherein each target probe in the plurality comprises:
      i. a target-binding molecule that specifically binds to a distinct target molecule in the sample;
      ii. an identification nucleotide sequence that identifies the target-binding molecule; and
      iii. a cleavable linker between the target-binding molecule and the identification nucleotide sequence;
   b. separating unbound target probes from a plurality of complexes in the sample, each complex having a target molecule and a single target probe bound thereto, wherein the complex does not have a second target probe binding to a different region of the target molecule;
   c. releasing the identification nucleotide sequences from the plurality of complexes;
   d. coupling the released identification nucleotide sequences from the releasing step (c) to a detection composition comprising a plurality of reporter probes, wherein each reporter probe in the plurality comprises a detectable label that identifies the reporter probe, wherein the label creates a unique distinguishable signal for each reporter probe; and
   e. detecting signals from the released identification nucleotide sequences based on a non-gel electrophoresis method, wherein the signals are distinguishable for the identification nucleotide sequences, thereby identifying the corresponding target-binding molecules and detecting a plurality of different target molecules in the sample.

2. The method of claim 1, wherein the composition further comprises a plurality of control probes, wherein each control probe in the plurality comprises a control-binding molecule that specifically binds to one control molecule in the sample; an identification control sequence that identifies the control-binding molecule; and a cleavable linker between the control-binding molecule and the identification control sequence, and wherein the method, further comprises quantifying the signals by normalizing the signals associated with the target probes by the signals associated with the control probes.

3. The method of claim 1, wherein the detecting step (e) comprises no amplification of the released identification nucleotide sequences.

4. The method of claim 1, wherein the target-binding molecule is an antibody.

5. The method of claim 1, wherein the target-binding molecule is a nucleic acid.

6. The method of claim 1, wherein the cleavable linker is a cleavable non-hybridizable linker.

7. The method of claim 6, wherein the cleavable, non-hybridizable linker is sensitive to an enzyme, pH, temperature, light, shear stress, sonication, a chemical agent, or any combination thereof.

8. The method of claim 6, wherein the cleavable, non-hybridizable linker comprises a photocleavable linker.

9. The method of claim 1, wherein the releasing of the identification nucleotide sequences from the bound target probes comprises exposing the bound target probes to ultraviolet light.

10. The method of claim 1, wherein the detection composition further comprises a plurality of capture probes, wherein each capture probe comprises an affinity tag.

11. The method of claim 10, wherein the affinity tag of the capture probe permits immobilization of the released identification nucleotide sequences onto a solid substrate, upon coupling to the detection composition.

12. A kit for multiplexed detection of a plurality of different target molecules from a sample comprising:
  a. a plurality of target probes, wherein each target probe in the plurality comprises:
    i. a target-binding molecule that specifically binds to a distinct target molecule in the sample;
    ii. an identification nucleotide sequence that identifies the target-binding molecule; and
    iii. a cleavable, non-hybridizable linker between the target-binding molecule and the identification nucleotide sequence;
  b. a plurality of reporter probes, wherein each reporter probe comprises:
    i. a first target probe-specific region that is capable of binding a first portion of the identification nucleotide sequence; and
    ii. a detectable label that identifies the reporter probe; and
  c. a plurality of capture probes, wherein each capture comprises:
    i. a second target probe-specific region that is capable of binding a second portion of the identification nucleotide sequence; and
    ii. an affinity tag for immobilization of the identification nucleotide sequence to a solid substrate surface.

13. The kit of claim 12, wherein the target-binding molecule is an antibody.

14. The kit of claim 12, wherein the target-binding molecule is a nucleic acid.

* * * * *

SEQUENCE LISTING

<160> NUMBER OF SEQ ID NOS: 110

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gctaagtttg gaattaagaa aggagttgct ggaggtcctt tccagcataa gaaccagcca    60
tattgcttaa                                                          70

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgccttctga aagagacgtt attgttgaag caagagatag cttagtaaca aatgctatag      60
ctcaggcagg                                                             70

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctgatcatg ctttgtcagc agacccagaa gaattcatca caatcactgg aagattgagc      60
ttaggaaagt                                                             70

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gagcggatgt tattgagaag cactttacct tagatttcta aagctctctt cctcctctct      60
tctccgctca                                                             70

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcggctgtg cgattgctat tgatgtgtta agaaatttgg tttgtgattg gcaaatctct      60
cctccaactc                                                             70

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atttggatga agtcggcttt atggtgacac aaatcatgat gagctgaggt tctgacagca      60
aatacgctca                                                             70

<210> SEQ ID NO 7
<211> LENGTH: 70
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 7
atagaaccat tgctgatga ggtgacaaca gatcgttgca cttatgctat cccgttagac    60
tatctgctat                                                          70

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actaccatgt actgcgcgag actagcctat cattggattg cagcgatgac tatatctgag    60
cacctgtgac                                                           70

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atatgagacg actagcacgc catagcgtta catacgtgtc gatccgagaa catcactcta    60
atgacgagtg                                                           70

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
catcatcgac agttcgcagc cctataacat gatactagat aacgatgctc catgttagtg    60
aatgcgagtc                                                           70

<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actcacacat agtactgaca cgtaagatag gatgctatat ggtcattggt cacccgagtt    60
acgatcaaat                                                           70

<210> SEQ ID NO 12
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 12
cagatagact cacctcgata tacagggagc cacgacttag gactatggat aagtcatcta    60
aagcgtccga                                                          70

<210> SEQ ID NO 13
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cactgtctat acatggacga cactttgcac atcattacca aagagcgcaa cgtatctagg    60
attgagcagt                                                          70

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agactaattg atcggaccga tgacagttca cagagggata cactgttgag ccgaccctat    60
tagctgatat                                                          70

<210> SEQ ID NO 15
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgatccacac tgacgaatca tgtactcact cgatcgccac ttcacacaag aacacaaatt    60
tggagtattg                                                          70

<210> SEQ ID NO 16
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctcgagaatc acacacagtc gtctaagaca cgacaagtgc aacagcaatc cacatcttag    60
atgagattag                                                          70

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgattacaag gcgtggtcag atattagact ccaggggatt taatgccagt ccaagctctc    60
ttccacattc                                                              70

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atctgcatga acgggaaagg agttcgatga gactttcaaa ccaacataat gtctctccaa       60
cctcaggaag                                                              70

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atagtcttta gagcctcaga ataggctgtg acgcggaaga taactcataa gtgcctccct       60
cggtaatttg                                                              70

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gccaggtatg ccgtgaacga gttcttcatt aactgttatg tctcgggagt ctgatattgg       60
tacttctccc                                                              70

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttagcaccga tatcaatact gatgatgtca ccgtcgagct cgtgttgaac ccttcaagta       60
acaacctgac                                                              70

<210> SEQ ID NO 22
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
acttgttcga ctgacagttt aacgcctgac atgaacggct tgcttataat gactggcagg       60
gttatgaatg                                                              70

<210> SEQ ID NO 23
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaactgaccg taccgttaga agagagttcc gcttctctca tgatgtgcgc atctcccaca     60
ttatttgacc                                                           70

<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgatgacagt gacaattgac cgaattgcct gatcattacc ttacagtgcg cagattggga     60
taatcgattt                                                           70

<210> SEQ ID NO 25
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
taggcgttga ggctttgttt ctttgcctct attgtaagac tcattctgac ggcctctagt     60
cgttgatatg                                                           70

<210> SEQ ID NO 26
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaggacattc tttcgaatgc aagttcaagg cacattttct atatcagcca ccatgggagt     60
gacatttctt                                                           70

<210> SEQ ID NO 27
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caatagctcc agtagtaatt gttgtcgctc cgctgagcag ttaatcctta tgtcaacaac     60
ctcagcatag                                                           70

<210> SEQ ID NO 28
<211> LENGTH: 70
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 28
ttcaccaagc tgaacagggt tgcgctgaat aaattttaca ggatactatg gacaggttca    60
gaatcctcga                                                          70

<210> SEQ ID NO 29
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggaatgaatc cattgcattt ccatgagaat gcagacttaa tcggacgtat cgactttggg    60
tccacgatat                                                          70

<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gaggtcttgt ttcatctaaa ccgagcagga tgataagcca taattcgtaa cccgagggta    60
taattcgtta                                                          70

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtccttctgc ttatgacatt ccgtgcattc cgtagctacg tcaagcgtta catagtgacg    60
gaactgttag                                                          70

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tctgtacctt ggcactccat ctggtaagtc acttatagtt gtatggtttc agatgaggga    60
acgtgtagga                                                          70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 33
aatttctgag attgttggta gagggagaaa tgggaaggac atgtttcaac aatcaccgga    60
ttaaagcctt                                                          70

<210> SEQ ID NO 34
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgtggaagga ctgtgataaa ccaatagggt gtcaagatct gtaagtatgg gattagggat    60
gttctgccag                                                          70

<210> SEQ ID NO 35
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gccgtcggac ataaccactt ggatatatac gtagttcatc aaccttaact ccctctgggt    60
tcattgggag                                                          70

<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gctattgcag caaagagaac agacgcttta actggtatcg agcgcttaga tggctatatg    60
gtctactaga                                                          70

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaaatcagat cagttctaca ttcggtggga gccctctata tgattagatc ctgcagccgt    60
acttccgtca                                                          70

<210> SEQ ID NO 38
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggtggcttga tttaactgaa tcaggcccta accatttgta ttgtgtctac actggtccgt    60

```
tcttagacgc                                                            70
```

<210> SEQ ID NO 39
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
gttgtttacc ttgtagatcg acttcacatc agcggcagaa ggccctcaac gtaaatctgc     60
tccacattta                                                            70
```

<210> SEQ ID NO 40
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
tgttgacatc cgcaacaatg taccttatat cggcatatgg atctcttgat cgagcgaacc     60 tcccttttaac                                                           70
```

<210> SEQ ID NO 41
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
aaggtgattc actaaccagc tcttactcct cgttcggtag caaatgaaat gccggatgct     60
gttgaagtag                                                            70
```

<210> SEQ ID NO 42
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
cgcataactc gaaccacagt tactatcagt cgacatccca ccagagaaat tgaaggatat     60
tgttgaagca                                                            70
```

<210> SEQ ID NO 43
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gaatcttgga aggtttccag ttaaataggg cgtgcgaaga ttccaggcag atttctcagg     60
aattcagtca                                                            70
```

<210> SEQ ID NO 44

```
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgctaatgc tgatggccca ccttctctat ttgtcgccat tatatgcgtt gaggttagtt    60
caagcaatac                                                          70

<210> SEQ ID NO 45
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gaacagcttt ccttgctccc tctaaatcac catttccatt agatgaaacc gacttcattc    60
cagactcaat                                                          70

<210> SEQ ID NO 46
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aatgcatttg ccaatgtagc cattgtataa ccagatacac tagtccaatg tctcaaccag    60
ggataccaca                                                          70

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctcagagctt caaatctatc ctctggaatc tctgtataag ccctcgaata caacttgagg    60
tatcccgcat                                                          70

<210> SEQ ID NO 48
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ctcttctgcc ctacatcact atcgactata gcaacatatc tttctcgggt aaagattagg    60
cgtccgatat                                                          70

<210> SEQ ID NO 49
<211> LENGTH: 70
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 49
gtaaccgtag tcgcgcaaac cgttatatta cggatatgat ccaagttata tacattagga    60
cgcggttgct                                                           70

<210> SEQ ID NO 50
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atggttagta aacagctttg atttctacat ccgcctagca aacccatagt tctgcagtag    60
attcacagcg                                                           70

<210> SEQ ID NO 51
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttcagttata atgtgtccag cagaagcagg aattgaatta cccaagttgc aagtggaaga    60
tttggagtta                                                           70

<210> SEQ ID NO 52
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttgcagaagc attcccaata tgggtttcaa gagtttaaag aatgtggaac attcatggga    60
actggtgaag                                                           70

<210> SEQ ID NO 53
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcaacaacct catctatact gtgaatagtc cctccgctgt ctatattgga actgctgcaa    60
tggttgctct                                                           70

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccgcagatta tcgtttacga tgcatccatg gtctccgacc cattgagaga gccaatggaa    60
ttaagaactt                                                          70

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caccattcag cctgatattg cgtttggtgt tgatgtggca actgcatact gaataactcc    60
ctgaaatagc                                                          70

<210> SEQ ID NO 56
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cgttacatac tcagccatag gcttcgataa cagcattatt ggaacctctg ggacattaac    60
agagacaaca                                                          70

<210> SEQ ID NO 57
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agcgtactag gcatctattg gctgaactac catgtaatta gtggtgttcc agcctctaag    60
atgatgtggt                                                          70

<210> SEQ ID NO 58
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gataggatgc gactgcgtat catataggct gcacattagc tgttgcttca aatgccaatc    60
ttacctcaac                                                          70

<210> SEQ ID NO 59
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aatgtatgag cggacactat gctaagagag actccatcaa tccctctatg caagataaca    60
acatctggct                                                          70

<210> SEQ ID NO 60
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgcacatcat agtgcgacgt tgatccagat agactataag acggcttggc atttaccta      60 gtcactatct                                                            70

<210> SEQ ID NO 61
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aatgtgtcag cggcctaact gtaattgatc cacaccttag ttcgggagct accgatctaa      60
tcaaccgttt                                                            70

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agactccagg tcgatcattg gataaccaac cagtcggtta tccatgacga gtgaataatc      60
ttaccgcagg                                                            70

<210> SEQ ID NO 63
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tttagatcct aagaatgcga aatgccgatt cccgcatatt tcgtaagctc gttcgggact      60
ttgtatcggc                                                            70

<210> SEQ ID NO 64
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gagtgatagg atcactctaa gatcggccac tatacgacgc tgaggtttat atgaacggcc      60
gcaattatga                                                            70

<210> SEQ ID NO 65
<211> LENGTH: 70

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tcttgaccaa caccatgtcc gacatactcc ctaacatggg tacggcgact actgaatcgt    60
tctttgagag                                                           70

<210> SEQ ID NO 66
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgtgtaaatg aaagcatctg actcaacagg catcagtaac gataatgagt acaacgccca    60
atggtcatag                                                           70

<210> SEQ ID NO 67
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcttcaacga tttcaatata cccattcgtc agaggaagta gtagatcccg ccgtcttagt    60
cggattgaaa                                                           70

<210> SEQ ID NO 68
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgtggttccg gttgcgtata gatcatgatt ctttacccac ctcttgctgt aatgaccaca    60
atcaacgtag                                                           70

<210> SEQ ID NO 69
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gtatcggcga acacgaaatc ctctactctt gacaaactcc cattcctacc tctccaaagt    60
tagaggagat                                                           70

<210> SEQ ID NO 70
<211> LENGTH: 70
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 70
ttgcattaca atggccgatc aagataagga cattcataat ggagctatag aatacaacac    60
caacgtcgca                                                           70

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
taattcttcc ttgattccgt gattggatgt ccctcaggag tagtagtgtg gatgttgttg    60
ttagacactt                                                           70

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tggagggtcg taaccgctat agatgtgatt cactccaaca acttccctat ctttaatcct    60
ctcactccac                                                           70

<210> SEQ ID NO 73
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgaataaatt cgttggcgct gtagagatcg gagttccgga ttcgtactac tcgtttacgg    60
gatttacaga                                                           70

<210> SEQ ID NO 74
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gctaaaggag actccggttt aaacgtcatc gcaatctttg atgggcaagc gagcacatag    60
atatgcgtta                                                           70

<210> SEQ ID NO 75
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aatattctcc ggcatgaatg gcgtgggaat gaatccggct ttgtgtttat tgtacataga    60
cgttgtcccg                                                           70

<210> SEQ ID NO 76
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gagaacgagc ggagcaagat agcctttaac tgaatcgtcg tcttattccc agtacacatc    60
attccaaatg                                                           70

<210> SEQ ID NO 77
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atattctgta ctcagtgcct atccacctaa tagggacctc agcgacctgt ccgttacatt    60
aatgaaacat                                                           70

<210> SEQ ID NO 78
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cattccgtag aattactaca ccgcgggatc attataacgt cgaagagctt cagaggtaag    60
tgaaacaagg                                                           70

<210> SEQ ID NO 79
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cccgaaggca taatcaacat ccattgtaca tcccttgtta tagctccagg gccagagatt    60
aaaggaatag                                                           70

<210> SEQ ID NO 80
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctaggatgta acttgcgtta gttgcagatt cgctatattg cttaagctct gagctccatg    60
tccagtaatt                                                           70

<210> SEQ ID NO 81
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ttctcgcagt tgtaaactta tagtgtcgcg cctagaaatt catagccaca aattctcttt    60
gggcagagat                                                          70

<210> SEQ ID NO 82
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tatagttacc aagtactatg ggttggtgga agccgaacgt ctgtccaaat ggagctatag    60
ttaagaggga                                                          70

<210> SEQ ID NO 83
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agacgcacac cgatagagga gagatcttac atacctgcta aggttgttaa tggcattgca    60
gatagcttag                                                          70

<210> SEQ ID NO 84
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ccagaaaggt acagggccaa ttaacacgta atcggcctcc aactctgcca tctttaagca    60
ttctaaagct                                                          70

<210> SEQ ID NO 85
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aattctccgt catgtggtcg tctgatgcct aactttatct gctatcaatg tagaggatcg    60
tgcattaccg                                                          70

<210> SEQ ID NO 86
<211> LENGTH: 70
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 86
cgcgggctaa gtagtagggt tctaatgcta ctttaaatac gctcacaatc caggctatat    60
cgctgtagct    70

<210> SEQ ID NO 87
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 87
taatcactgt atttgttaat catggctagg cgggtccaat agggaaactg atactaacgt    60
aggagcacgc    70

<210> SEQ ID NO 88
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 88
gtattctgga gaacctcgtg gcaatggcaa ttctccacga gtgctaagat ctgagccgtt    60
taccaaagag    70

<210> SEQ ID NO 89
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 89
ataacctggt ctccggttga tcgtttacct gaaacatgag attagcaacg acccaaacat    60
gccacttcac    70

<210> SEQ ID NO 90
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 90
cacaacatgc agcaggcaag tagggtttct gattataagc atccagcaat aaagcctcct    60
tcaaaccaac    70

<210> SEQ ID NO 91
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 91
ccctaaccat gttctacgag cggtcacaga ttatattcaa ctacaagtgt aaatgtacga        60
gcgccgagat                                                              70

<210> SEQ ID NO 92
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gaaaggcatt tgacgggagc attgacgaag acatacggta atttgtcgtc gcacggacaa        60
ttagtgagtt                                                              70

<210> SEQ ID NO 93
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
taatactggg tcacaagatt agattccagc tgtgacggcg atgaagtccg cgaggatatg        60
tttctatatc                                                              70

<210> SEQ ID NO 94
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ggttcattgt ctcatcgtac ggctaatgta gatacgaggt agccgagtat gacacaccac        60
agcagttaat                                                              70

<210> SEQ ID NO 95
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ttatggattc cgatgatcct ccgcgtggta caaatgttac cttgatgcaa tagtctctgt        60
atgcgatcgg                                                              70

<210> SEQ ID NO 96
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
agcggtacta atatgctatg agcgagttcc ctaacgagag ataacgaccc tctgtcgtaa        60

```
gcacttaagg                                                              70

<210> SEQ ID NO 97
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gaggcatctc tgctaactat atgctgaaca gcttttccac gatataggta cattggacgc       60
ttacaggata                                                              70

<210> SEQ ID NO 98
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tttcggccca acttatatgc tctccgaatc ttggagcagt catcgtaacc tgatagcaat       60
ctacgtcaag                                                              70

<210> SEQ ID NO 99
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
actgcagtga gggcaaccaa tacaaattaa atctgcctcc tattgggata cctcccgtcc       60
attaagttag                                                              70

<210> SEQ ID NO 100
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ttggagaaac aaccatacag gtgtctttaa ctacctggaa ctctaccaat tggagctttc       60
ttagctgtct                                                              70

<210> SEQ ID NO 101
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gctatcaact tccctatcca aaccgttgga tgaattgaaa gcatagatgt tccttggaga       60
ggtttcccag                                                              70
```

<210> SEQ ID NO 102
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
tgaggagtaa gtatacgacg cctgcactag tcacttgctg gctttgagcc aatagatgtg    60
ttaatggcta                                                            70

<210> SEQ ID NO 103
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
cacagccaat ctcttaggac agtacatggt tagtaacgtc tgtggaagtc atgagcacac    60
gatctgtaag                                                            70

<210> SEQ ID NO 104
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
tgagtatcta caggtgttct catgggatcg tagttggtct gtccaacatg acgttatagg    60
cataactcca                                                            70

<210> SEQ ID NO 105
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
taccttaaac tgcgctggta acttggatcg tgtagtcatt gggagcaaac catctgtctt    60
tcgtatggag                                                            70

<210> SEQ ID NO 106
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
gttaggttca gcctcattcc ctaagaatcc aactcataac tcaatcatgc gcgtccagca    60
aagacaaatg                                                            70

<210> SEQ ID NO 107
<211> LENGTH: 70
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 107
actgtctaat acaaccggat tctaagacca catggtctta gacgcgcgtg caattctgaa    60
ctatatgatt                                                           70

<210> SEQ ID NO 108
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tggctattgc cgcagtagat caaagattga gagagatata gattactcca tgatacaccc    60
aagcctcgac                                                           70

<210> SEQ ID NO 109
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gcaacaagtg atgctgacgc agttgttata gatggccttt ggctcacgct aattgagtta    60
ctgtaggaaa                                                           70

<210> SEQ ID NO 110
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctatctcac cagctcctca ccatgacatt tactctccac atttatctgc gacctgtttc    60
gtaaacgatg                                                           70
```